United States Patent
Uhrich et al.

(10) Patent No.: US 10,640,725 B2
(45) Date of Patent: May 5, 2020

(54) THERMOCLEAVABLE FRICTION MODIFIERS AND METHODS THEREOF

(71) Applicants: Rutgers, The State University of New Jersey, New Brunswick, NJ (US); ExxonMobil Research and Engineering Company, Annandale, NJ (US)

(72) Inventors: Kathryn Uhrich, New Brunswick, NJ (US); Jonathan Faig, New Brunswick, NJ (US); Yingyue Zhang, New Brunswick, NJ (US); Shuji Luo, Basking Ridge, NJ (US); Man Kit Ng, Basking Ridge, NJ (US); Alan Schilowitz, Highland Park, NJ (US); Anne Marie Shough, Conroe, TX (US)

(73) Assignees: Rutgers, The State University of New Jersey, New Brunswick, NJ (US); ExxonMobil Research and Engineering Company, Annandale, NJ (US)

(*) Notice: Subject to any disclaimer, the term of this patent is extended or adjusted under 35 U.S.C. 154(b) by 117 days.

(21) Appl. No.: 15/670,891

(22) Filed: Aug. 7, 2017

(65) Prior Publication Data
US 2018/0037840 A1    Feb. 8, 2018

Related U.S. Application Data

(60) Provisional application No. 62/371,580, filed on Aug. 5, 2016.

(51) Int. Cl.
*C10M 169/04* (2006.01)
*C10M 129/42* (2006.01)
(Continued)

(52) U.S. Cl.
CPC .......... *C10M 169/04* (2013.01); *C07C 69/02* (2013.01); *C07C 69/533* (2013.01);
(Continued)

(58) Field of Classification Search
CPC .......... C10M 169/04; C10M 2207/282; C10M 129/42; C10M 129/72; C10M 129/76;
(Continued)

(56) References Cited

U.S. PATENT DOCUMENTS 1,815,022 A    7/1931    Davis
2,015,748 A    10/1935   Frolich
(Continued)

FOREIGN PATENT DOCUMENTS

CA    1094044 A    1/1981
EP    0464546 A1   1/1992
(Continued)

OTHER PUBLICATIONS

Faig, A., Petersen, L.K., Moghe, P.V., Uhrich, K.E., "Impact of Hydrophobic Chain Composition on Amphiphilic Macromolecule Antiatherogenic Bioactivity", Biomacromolecules 2014, 15(9), 3328-37 (Year: 2014).*
(Continued)

*Primary Examiner* — James C Goloboy
(74) *Attorney, Agent, or Firm* — Viksnins Harris Padys Malen LLP

(57) ABSTRACT

Certain embodiments of the invention provide a lubricating oil composition comprising a lubricating oil base stock and a compound of formula (I):
(Continued)

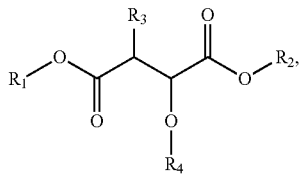

(I)

or a salt thereof, wherein $R_1$, $R_2$, $R_3$ and $R_4$ have any of the values defined in the specification, as well as methods of use thereof.

27 Claims, 14 Drawing Sheets

(51) Int. Cl.
C10M 129/76 (2006.01)
C07C 69/02 (2006.01)
C07C 69/533 (2006.01)
C07C 69/612 (2006.01)
C07C 69/708 (2006.01)
C10M 105/00 (2006.01)
C10M 129/72 (2006.01)
C10M 129/95 (2006.01)

(52) U.S. Cl.
CPC .......... *C07C 69/612* (2013.01); *C07C 69/708* (2013.01); *C10M 129/42* (2013.01); *C10M 129/72* (2013.01); *C10M 129/76* (2013.01); C10M 2203/003 (2013.01); C10M 2207/123 (2013.01); C10M 2207/124 (2013.01); C10M 2207/127 (2013.01); C10M 2207/128 (2013.01); C10M 2207/282 (2013.01); C10M 2207/284 (2013.01); C10M 2207/288 (2013.01); C10N 2230/06 (2013.01); C10N 2230/54 (2013.01); C10N 2240/10 (2013.01)

(58) Field of Classification Search
CPC ...... C10M 2207/123; C10M 2207/124; C10M 2207/127; C10M 2207/128; C10M 2207/284; C10M 2207/288; C07C 69/02; C07C 69/533; C07C 69/612; C07C 69/708; C10N 2230/06; C10N 2230/54; C10N 2240/10

See application file for complete search history.

(56) References Cited

U.S. PATENT DOCUMENTS

| | | |
|---|---|---|
| 2,100,993 A | 11/1937 | Bruson |
| 2,191,498 A | 2/1940 | Reiff |
| 2,387,501 A | 10/1945 | Dietrich |
| 2,655,479 A | 10/1953 | Munday et al. |
| 2,666,746 A | 1/1954 | Munday et al. |
| 2,721,877 A | 10/1955 | Popkin et al. |
| 2,721,878 A | 10/1955 | Popkin |
| 2,817,693 A | 12/1957 | Jacob et al. |
| 3,036,003 A | 5/1962 | Arthur |
| 3,087,936 A | 4/1963 | Le |
| 3,172,892 A | 3/1965 | Le et al. |
| 3,200,107 A | 8/1965 | Le |
| 3,219,666 A | 11/1965 | Le et al. |
| 3,250,715 A | 5/1966 | Wyman |
| 3,254,025 A | 5/1966 | Le |
| 3,272,746 A | 9/1966 | Le et al. |
| 3,275,554 A | 9/1966 | Hendrik |
| 3,316,177 A | 4/1967 | Dorer |
| 3,322,670 A | 5/1967 | Burt et al. |
| 3,329,658 A | 7/1967 | Fields |
| 3,341,542 A | 9/1967 | Le et al. |
| 3,382,291 A | 5/1968 | Brennan |
| 3,413,347 A | 11/1968 | Worrel |
| 3,438,757 A | 4/1969 | Honnen et al. |
| 3,444,170 A | 5/1969 | Norman et al. |
| 3,449,250 A | 6/1969 | Fields |
| 3,454,555 A | 7/1969 | Voort et al. |
| 3,454,607 A | 7/1969 | Suer et al. |
| 3,519,565 A | 7/1970 | Coleman |
| 3,541,012 A | 11/1970 | Stuebe |
| 3,565,804 A | 2/1971 | Honnen et al. |
| 3,595,791 A | 7/1971 | Cohen |
| 3,630,904 A | 12/1971 | Musser et al. |
| 3,632,511 A | 1/1972 | Liao |
| 3,652,616 A | 3/1972 | Watson et al. |
| 3,666,730 A | 5/1972 | Coleman |
| 3,687,849 A | 8/1972 | Abbott |
| 3,697,574 A | 10/1972 | Piasek et al. |
| 3,702,300 A | 11/1972 | Coleman |
| 3,703,536 A | 11/1972 | Piasek et al. |
| 3,704,308 A | 11/1972 | Piasek et al. |
| 3,725,277 A | 4/1973 | Worrel |
| 3,725,480 A | 4/1973 | Traise et al. |
| 3,726,882 A | 4/1973 | Traise et al. |
| 3,742,082 A | 6/1973 | Brennan |
| 3,751,365 A | 8/1973 | Piasek et al. |
| 3,755,433 A | 8/1973 | Miller et al. |
| 3,756,953 A | 9/1973 | Piasek et al. |
| 3,769,363 A | 10/1973 | Brennan |
| 3,787,374 A | 1/1974 | Adams |
| 3,798,165 A | 3/1974 | Piasek et al. |
| 3,803,039 A | 4/1974 | Piasek et al. |
| 3,822,209 A | 7/1974 | Knapp et al. |
| 3,876,720 A | 4/1975 | Heilman et al. |
| 3,948,800 A | 4/1976 | Meinhardt |
| 4,065,598 A | 12/1977 | Takahashi et al. |
| 4,100,082 A | 7/1978 | Clason et al. |
| 4,149,178 A | 4/1979 | Estes |
| 4,218,330 A | 8/1980 | Shubkin |
| 4,234,435 A | 11/1980 | Meinhardt et al. |
| 4,239,930 A | 12/1980 | Allphin et al. |
| 4,367,352 A | 1/1983 | Watts et al. |
| 4,413,156 A | 11/1983 | Watts et al. |
| 4,426,305 A | 1/1984 | Malec |
| 4,434,408 A | 2/1984 | Baba et al. |
| 4,454,059 A | 6/1984 | Pindar et al. |
| 4,594,172 A | 6/1986 | Sie |
| 4,767,551 A | 8/1988 | Hunt et al. |
| 4,798,684 A | 1/1989 | Salomon |
| 4,827,064 A | 5/1989 | Wu |
| 4,827,073 A | 5/1989 | Wu |
| 4,830,787 A * | 5/1989 | Klemann ............... A23D 7/013 426/603 |
| 4,897,178 A | 1/1990 | Best et al. |
| 4,910,355 A | 3/1990 | Shubkin et al. |
| 4,921,594 A | 5/1990 | Miller |
| 4,943,672 A | 7/1990 | Hamner et al. |
| 4,952,739 A | 8/1990 | Chen |
| 4,956,122 A | 9/1990 | Watts et al. |
| 4,975,177 A | 12/1990 | Garwood et al. |
| 5,068,487 A | 11/1991 | Theriot |
| 5,075,269 A | 12/1991 | Degnan et al. |
| 5,084,197 A | 1/1992 | Galic et al. |
| 5,430,105 A | 7/1995 | Redpath et al. |
| 5,705,458 A | 1/1998 | Roby et al. |
| 6,034,039 A | 3/2000 | Gomes et al. |
| 6,080,301 A | 6/2000 | Berlowitz et al. |
| 6,090,989 A | 7/2000 | Trewella et al. |
| 6,165,949 A | 12/2000 | Berlowitz et al. |
| 6,323,164 B1 | 11/2001 | Liesen et al. |
| 6,328,988 B1 | 12/2001 | Uhrich et al. |
| 6,365,146 B1 | 4/2002 | Uhrich et al. |
| 6,497,895 B2 | 12/2002 | Uhrich et al. |
| 7,262,221 B2 | 8/2007 | Uhrich et al. |
| 7,470,802 B2 | 12/2008 | Uhrich et al. |
| 7,704,930 B2 | 4/2010 | Deckman et al. |
| 7,888,298 B2 | 2/2011 | Poirier et al. |

(56) References Cited

U.S. PATENT DOCUMENTS

| | | | |
|---|---|---|---|
| 7,989,408 B2 | 8/2011 | Poirier et al. | |
| 8,048,833 B2 | 11/2011 | Habeeb et al. | |
| 8,192,754 B2 | 6/2012 | Uhrich et al. | |
| 8,846,850 B2 | 9/2014 | Uhrich et al. | |
| 9,206,372 B2 | 12/2015 | Wang et al. | |
| 9,228,147 B2 | 1/2016 | Patil et al. | |
| 9,228,149 B2 | 1/2016 | Haque et al. | |
| 9,434,681 B2 | 9/2016 | Uhrich et al. | |
| 9,630,905 B2 | 4/2017 | Uhrich et al. | |
| 10,138,203 B2 | 11/2018 | Uhrich et al. | |
| 2001/0051747 A1* | 12/2001 | Vries | C07B 57/00 562/401 |
| 2004/0198641 A1 | 10/2004 | Uhrich et al. | |
| 2005/0089504 A1 | 4/2005 | Uhrich et al. | |
| 2006/0183647 A1 | 8/2006 | Kocsis et al. | |
| 2008/0020950 A1 | 1/2008 | Gray et al. | |
| 2008/0057026 A1 | 3/2008 | Uhrich et al. | |
| 2009/0175932 A1 | 7/2009 | Uhrich et al. | |
| 2011/0008396 A1 | 1/2011 | Moghe et al. | |
| 2011/0229416 A1 | 9/2011 | Uhrich et al. | |
| 2012/0022159 A1 | 1/2012 | Uhrich et al. | |
| 2012/0039983 A1 | 2/2012 | Uhrich et al. | |
| 2012/0219598 A1 | 8/2012 | Uhrich et al. | |
| 2012/0225926 A1 | 9/2012 | Uhrich et al. | |
| 2015/0164100 A1* | 6/2015 | Alvarez | A23D 9/00 426/607 |
| 2015/0344805 A1 | 12/2015 | Dance et al. | |
| 2016/0068467 A1 | 3/2016 | Uhrich et al. | |
| 2018/0037840 A1 | 2/2018 | Uhrich et al. | |
| 2019/0119199 A1 | 4/2019 | Uhrich et al. | |
| 2019/0161436 A1 | 5/2019 | Uhrich et al. | |

FOREIGN PATENT DOCUMENTS

| | | | |
|---|---|---|---|
| EP | 0464547 A1 | 1/1992 | |
| JP | 06145341 A | 5/1994 | |
| JP | 08117328 A * | 5/1996 | |
| WO | 1991013133 A2 | 9/1991 | |
| WO | 2000065024 A2 | 11/2000 | |
| WO | 2001005873 A1 | 1/2001 | |
| WO | 2003005959 A2 | 1/2003 | |
| WO | 2003047518 A2 | 6/2003 | |
| WO | 2003103594 A2 | 12/2003 | |
| WO | 2005074887 A2 | 8/2005 | |
| WO | 2009039505 A1 | 3/2009 | |
| WO | 2012056191 A1 | 5/2012 | |
| WO | WO-2012056191 A1 * | 5/2012 | C10L 1/19 |
| WO | 2013188882 A1 | 12/2013 | |
| WO | 2015195563 A1 | 12/2015 | |
| WO | 2017165836 A1 | 9/2017 | |

OTHER PUBLICATIONS

Kawase., T., Saito, I., Oida, T., "Monolayer Behavoir of Asymmetrical Gemini Amphiphiles", J. Oleo Sci, 2013, 62(6). 371-380 (Year: 2013).*

Uray, G., Lindner, W., "tert-Butyl Esters and Ethers of (R,R)-Tartaric Acid", Tetrahedron, 44(14), 4357-4362, 1988 (Year: 1988).*

Allen, C , et al., "Boundary layer lubrication: monolayer or multilayer", Wear 14(5), 363-384 (1969).

Allen, C. , et al., "Nano-engineering block copolymer aggregates for drug delivery", Colloids and Surfaces B: Biointerfaces 16, 3-27 (1999).

Bowden , et al., "Lubrication of Metal Surfaces by Fatty Acids", Nature 156, 97-101 (1945).

Camejo , et al., "The extracellular matrix on atherogenesis and diabetes-associated vascular disease", Atherosclerosis Supplements 3, 3-9 (2002).

Gammas , et al., "Functional poly[(ethylene oxide)—co-($\square$-benzyl-L-aspartate)] polymeric micelles: block copolymer synthesis and micelles formation", Macromol. Chem. Phys., 196, 1899-1905 (1995).

Chem Abstract , of JP-6305820 (1994).

Chnari, E. , et al., "Engineered polymeric nanoparticles for receptor-targeted blockage of oxidized low density lipoprotein uptake and atherogenesis in macrophages", Biomacromolecules 7(6), 1796-1805 (2006).

Chnari, E. , et al., "Nanoscale anionic macromolecules can inhibit cellular uptake of differentially oxidized LDL", Biomacromolecules 7 (2), 597-603 (2006).

Chnari, E. , et al., "Nanoscale anionic macromolecules for selective retention of low-density lipoproteins", Biomaterials 26 (17), 3749-3758 (2005).

Djodjevic , et al., "Polymeric Micelles Based on Amphiphilic Scorpion-like Macromolecules: Novel Carriers for Water-Insoluble Drugs", Pharmaceutical Research, 22(1), 24-32 (2005).

Djordjevic , et al., "Amphiphilic Star-Like Macromolecules as Novel Carriers for Topical Delivery of Nonsteroidal Anti-Inflammatory Drugs", AAPS PharmSci, 5 (4), 1-12, 2003.

Dogu, T , et al., "DRIFT Studies for the Reaction and Adsorption of Alcohols and Isobutylene on Acidic Resin Catalysts and the Mechanism of ETBE and MTBE Synthesis", Ind Eng Chem Res 40, 5044-5051 (2001).

Faig, J , et al., "Thermocleavable friction modifiers for controlled release in lubricants", Tribology International doi: 10.1016/j.triboint. 2017.11.030, 40 pages (2017).

Gao , et al., "A model of micellization for block copolymers in solutions", Macromolecules 26, 7353-7360 (1993).

Gitsov , et al., "Micelles with highly branched nanoporous interior: solution properties and binding capabilities of amphiphilic copolymers with linear dendritic architecture", Journal of Polymer Science: Part A: Polymer Chemistry 38, 2711-2727 (2000).

Harmon , et al., "In Vitro Evaluation of Amphiphilic Macromolecular Nanocarriers for Systemic Drug Delivery", Journal of Bioactive and Compatible Polymers 24, 185-197 (2009).

Helgesen, M , et al., "Photovoltaic Performance of Polymers Based on Dithienylthienopyrazines Bearing Thermocleavable Benzoate Esters", Macromolecules 43(3), 1253-1260 (2010).

Hersey, M , "Logic of oiliness", Journal of American Society of Mechanical Engineers 55, 561 (1933).

Iverson, N , et al., "Controllable inhibition of cellular uptake of oxidized low-density lipoprotein: Structure-function relationships for nanoscale amphiphilic polymers", Acta Biomaterialia 6, 3081-3091 (2010).

Jahanmir, S , "Chain length effects in boundary lubrication", Wear 102(4), 331-349 (1985).

Jahanmir, S , et al., "Effect of Additive Molecular Structure on Friction Coefficient and Adsorption", Journal of Tribology 108(1), 109-116 (1986).

Kataoka, K. , et al., "Block copolymer micelles for drug delivery: design, characterization and biological significance", Adv Drug Deliv Rev. 47(1), 113-31 (2001).

Kawase, T , et al., "Effects of Hdrophobic Chain Length on Temperature Dependence of Monolayer Behavior of Ester-type Tartaric Geminis", Journal of Oleo Science 60(2), 61-69 (2011).

Kreig , et al., "Micelle formation of randomly grafted copolymers in slightly selective solvents", Journal of Chemical Physics 115(13), 6243-6251 (2001).

Langer, R. , "New Methods of Drug Delivery", Science, 249(4976), 1527-1533, (Sep. 1990).

Liu , et al., "Unimolecular micelles: Synthesis and characterization of amphiphilic polymer systems", Journal of Polymer Science, Part A:P Polymer Chemistry, 37(6), 703-711 (1999).

Maki, T , et al., "Catalytic monoalkylation of 1,2-diols", Tetrahedron Letters 50(13), 1466-1468 (2009).

Minami, I , et al., "Concept of molecular design towards additive technology for advanced lubricants", Lubrication Science 19(2), 127-149 (2007).

Moghimi, S. M., et al., "Exploiting bone marrow microvascular structure for drug delivery and future therapies", Advanced Drug Delivery Reviews 17, 61-73 (1995).

Moghimi , et al., "Long-circulating and target-specific nanoparticles: theory to practice", J. Pharm. Rev. 53(2), 283-318 (2001).

Moore, Jeffrey S., et al., "Room temperature polyesterification", Macromolecules 23 (1), 65-70 (1990).

(56) References Cited

OTHER PUBLICATIONS

Otsuka, H., et al., "Self-assembly of poly(ethylene glycol)-based block copolymers for biomedical applications", Current Opinion in Colloid & Interface Science 6(1), 3-10 (2001).

Papisov, M.I., et al., "Modeling in vivo transfer of long-circulating polymers (two classes of long circulating polymers and factors affecting their transfer in vivo)", Advanced Drug Delivery Reviews 16, 127-139 (1995).

Patent Cooperation Treaty, International Searching Authority, Search Report and Written Opinion for PCT/US2017/045761, 19 pages, dated Oct. 27, 2017.

Peterson, M, et al., "Thermocleavable Low Band Gap Polymers and Solar Cells Therefrom with Remarkable Stability toward Oxygen", Macromolecules 41(23), 8986-8994 (2008).

Remmert, S, et al., "Demonstration of Fuel Economy Benefit of Friction Modifier Additives via Fuel-to-Lubricant Transfer in Euro-5 Gasoline Fleet", SAE International Journal of Fuels and Lubricants 6(3), 677-690 (2013).

Rousselle, et al., "New advances in the transport of doxorubicin through the blood-brain barrier by a peptide vector-mediated strategy", Molecular Pharmacology 57, 679-686 (2000).

Rudolph, et al., "A TGA-FTIR Perspective of Fatty Acid Adsorbed on Magnetite Nanoparticles—Decomposition Steps and Magnetite Reduction", Colloids and Surfaces A: Physicochemical and Engineering Aspects 397, 16-23 (2012).

Schmalenberg, et al., "Cytotoxicity of a unimolecular polymeric micelle and its degradation products", Biomacromolecules 2, 851-855 (2001).

Storey, R, et al., "Real-Time Monitoring of Carbocationic Polymerization of Isobutylene Using in Situ FTIR-ATR Spectroscopy with Conduit and Diamond-Composite Sensor Technology", Macromolecules 31(5), 1523-1526 (1998).

Tang, Z, et al., "A review of recent developments of friction modifiers for liquid lubricants (2007—present)", Current Opinion in Solid State and Materials Science 18(3), 119-139 (2014).

Tao, L., et al., "Novel amphiphilic macromolecules and their in vitro characterization as stabilized micellar drug delivery systems", J. Colloid Interface Sci 298 (1), 102-110 (2006).

Temsamani, et al., "Brain drug delivery technologies: novel approaches for transporting therapeutics", PSTT 3(5), 155-162 (2000).

Tian, et al., "Amphiphilic scorpion-like macromolecules: design, synthesis and characterization", Macromolecules 37, 538-543 (2004).

Tian, et al., "Design and synthesis of amphiphilic poly(ethylene glycol) derivaties as a micellar drug delivery system", Polymer Preprints, 43(2), 719-720 (2002).

Tian, et al., "Design and synthesis of amphiphilic poly(ethylene glycol) derivaties as a micellar drug delivery system", Abstracts of Papers, Part 2, 224, (1-2), abstract 748, 224th ACS National Meeting (2002).

Tian, et al., "Novel amphiphilic macromolecules for drug delivery applications: design, synthesis and characterization", in Dissertation, New Brunswick, New Jersey, pp. 13-48, 114-138 and 160-175, 2004.

Torchilin, V.P., et al., "Structure and design of polymeric surfactant-based drug delivery systems", J Control Release 73(2-3), 137-172 (2001).

Tuzar, et al., "Micelles of Block and Graft Copolymers in Solutions", Surface and Colloid Science 15, 1-83 (1993).

Uray, G, et al., "tert-Butyl esters and ethers of (R,R)-tartaric acid", Tetrahedron 44(14), 4357-4362 (1988).

Wang, et al., "Comparison of PEG chain length and density on amphiphilic macromolecular nanocarriers: Self-assembled and unimolecular micelles", Acta Biomaterialia 5, 883-892 (2009).

Wang, et al., "Nanoscale amphiphilic macromolecules as lipoprotein inhibitors: the role of charge and architecture", Int. J. Nanomedicine 2(4), 697-705 (2007).

Williams, et al., "The response-to-retention hypothesis of early atherogenesis", Arteriosclerosis, Thrombosis & Vascular Biology 15(5), 551-561 (1995).

Zhang, Y, et al., "Micellar and structural stability of nanoscale amphiphilic polymers: Implications for antiatherosclerotic bioactivity", Biomaterials 84, 230-240 (2016).

Zhang, Y, et al., "Micro-strain Evolution and Toughening Mechanisms in a Trimodal Al-Based Metal Matrix Composite", Metallurgical and Materials Transactions A 41(2), 532-541 (2009).

Zhu, et al., "Super Microcapsules" (SMC. I. Preparation and Characterization of Star Polyethylene Oxide (POE)-Polylactide (PLA) Copolymers, J. Polym. Sci. Polm. Chem. 27, 2151 (1989).

* cited by examiner

Figure 3A. Before Heating (154): R = -Et
(4): $R_1$ = -Et
(6): $R_1$ = -tBu

THERMOCLEAVABLE FRICTION MODIFIERS AND METHODS THEREOF

RELATED APPLICATION

This application claims the benefit of priority of U.S. Provisional Application Ser. No. 62/371,580 filed on Aug. 5, 2016, which application is incorporated by reference herein.

FIELD

The present invention relates to lubricating oil compositions comprising a lubricating oil base stock and a compound of formula (I), or a salt thereof. The lubricating oil compositions of this disclosure may be used to reduce friction in engines or other mechanical components, which may be lubricated with a lubricating oil. For example, the lubricating oil compositions of this disclosure may be used in automotive, marine, aviation, industrial engine and machine component applications, and the like.

BACKGROUND OF THE INVENTION

Improving frictional properties in lubricant compositions has been an objective of the industry. Friction between two surfaces will increase the power required to effect movement, and where the movement is an integral part of an energy conversion system, it is most desirable to effect lubrication in a manner that will minimize this friction. By minimizing friction in a lubricant system, fuel economy and energy efficiency are maximized. Friction modifiers have been used to promote such friction-reducing properties in lubricant systems.

A variety of friction modifiers are known in the art and include both ash and ashless modifiers. Recent emission concerns have resulted in a preference for ashless friction modifiers, such as fatty acid esters and amides. While efficacious, fatty acids tend to have a low solubility in base oil, decompose over time, and increase the acidity of the formulation.

Currently, there is a need for ashless additives that effectively reduce the friction coefficient of oil-based lubricants, but have improved solubility in base oil and/or sustained performance over time.

SUMMARY OF THE INVENTION

Friction modifiers, which provide thermally triggered, controlled release performance overtime, are described herein. These modifiers may have improved solubility in base oil, improve the fuel economy of, and/or reduce the emission from, engines or other mechanical components, which may be lubricated with a lubricating oil. The lubricating oil compositions of this disclosure may be used in, e.g., in automotive, marine, aviation, industrial engine and machine component applications, and the like.

Other objects and advantages of the present disclosure will become apparent from the detailed description that follows.

Accordingly, certain embodiments of the invention provide a lubricating oil composition comprising a lubricating oil base stock and a compound of formula (I):

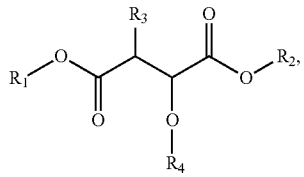

wherein, $R_1$ and $R_2$ are each independently H, $(C_1-C_{12})$alkyl, benzyl or phenethyl; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_1-C_{20})$alkyl, $(C_1-C_{20})$alkanoyl, $(C_2-C_{20})$alkenyl or $(C_3-C_{20})$alkenoyl; or a salt thereof.

Certain embodiments of the invention also provide a compound of formula (I):

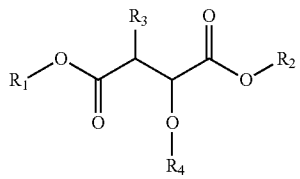

wherein, $R_1$ and $R_2$ are each independently H, $(C_1-C_{12})$alkyl, benzyl or phenethyl; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_1-C_{20})$alkyl, $(C_1-C_{20})$alkanoyl, $(C_2-C_{20})$alkenyl or $(C_3-C_{20})$alkenoyl; or a salt thereof, wherein the compound of formula (I) is not:

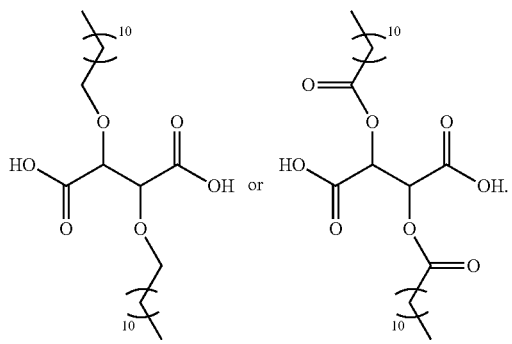

Certain embodiments of the invention provide a method for preparing a final compound of formula (I):

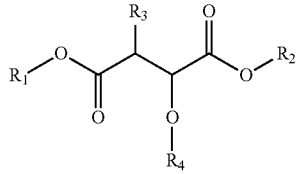

wherein, $R_1$ and $R_2$ are each independently $(C_1-C_{12})$alkyl, benzyl or phenethyl; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_1-C_{20})$alkyl, $(C_1-C_{20})$alkanoyl, $(C_2-C_{20})$alkenyl or $(C_3-C_{20})$alkenoyl;

comprising converting a corresponding compound, wherein $R_1$ and $R_2$ are each H, to the final compound of formula (I).

Certain embodiments of the invention provide a method for preparing a final compound of formula (I):

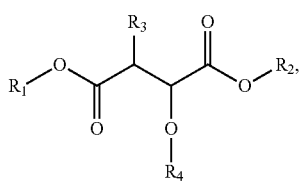
(I)

wherein, $R_1$ and $R_2$ are each H; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_1-C_{20})$alkyl, $(C_1-C_{20})$alkanoyl, $(C_2-C_{20})$alkenyl or $(C_3-C_{20})$alkenoyl; or a salt thereof, comprising acylating or alkylating tartaric acid to provide the final compound of formula (I), or a salt thereof.

Certain embodiments of the invention provide a method for preparing a final compound of formula (I):

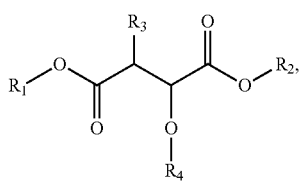
(I)

wherein, $R_1$ and $R_2$ are each H; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_1-C_{20})$alkyl, $(C_1-C_{20})$alkanoyl, $(C_2-C_{20})$alkenyl or $(C_3-C_{20})$alkenoyl; or a salt thereof, comprising saponifying a corresponding compound of formula (I), wherein $R_1$ and $R_2$ are each other than H, to provide the final compound of formula (I), or a salt thereof.

Certain embodiments of the invention provide a lubricating oil composition prepared by combining a lubricating oil base stock and a compound of formula (I):

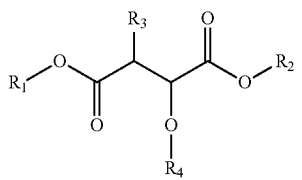
(I)

wherein, $R_1$ and $R_2$ are each independently H, $(C_1-C_{12})$alkyl, benzyl or phenethyl; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_1-C_{20})$alkyl, $(C_1-C_{20})$alkanoyl, $(C_2-C_{20})$alkenyl or $(C_3-C_{20})$alkenoyl; or a salt thereof.

Certain embodiments of the invention provide a method for improving the frictional properties of a lubricating oil composition, comprising adding to the lubricating oil composition a compound of formula (I):

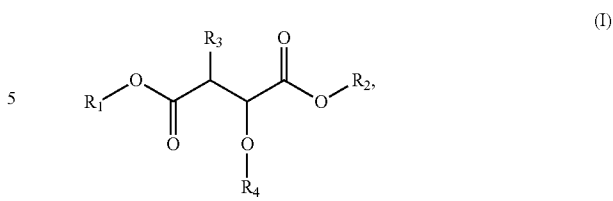
(I)

wherein, $R_1$ and $R_2$ are each independently H, $(C_1-C_{12})$alkyl, benzyl or phenethyl; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_1-C_{20})$alkyl, $(C_1-C_{20})$alkanoyl, $(C_2-C_{20})$alkenyl or $(C_3-C_{20})$alkenoyl; or a salt thereof.

Certain embodiments of the invention provide a method for improving friction control in an engine or other mechanical component lubricated with a lubricating oil, by using as the lubricating oil a formulated oil comprising a lubricating oil base stock as a major component, and one or more lubricating oil additives as a minor component, wherein at least one lubricating oil additive is a compound of formula (I):

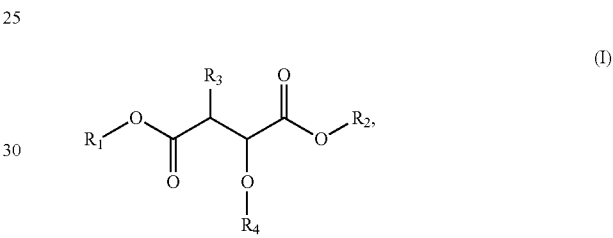
(I)

wherein, $R_1$ and $R_2$ are each independently H, $(C_1-C_{12})$alkyl, benzyl or phenethyl; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_1-C_{20})$alkyl, $(C_1-C_{20})$alkanoyl, $(C_2-C_{20})$alkenyl or $(C_3-C_{20})$alkenoyl; or a salt thereof.

Certain embodiments of the invention provide a method of reducing friction in an engine or other mechanical component lubricated with a lubricating oil, comprising providing a lubricating oil composition as described herein to the engine or other mechanical component.

Certain embodiments of the invention provide a method of providing friction reducing properties in a lubricant system, comprising adding a lubricating oil composition as described herein to the lubricant system.

Certain embodiments of the invention provide a method for improving the solubility (e.g., the solubility in non-polar media, such as, e.g., a lubricating oil base stock) of a compound of formula (I):

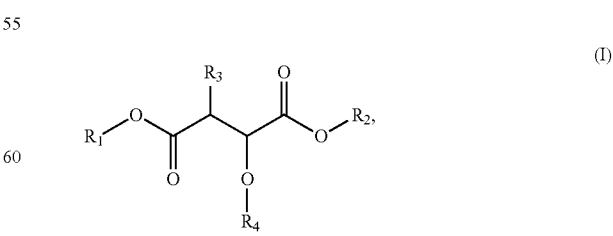
(I)

wherein, $R_1$ and $R_2$ are each H; comprising converting the compound to a corresponding compound of formula (I), wherein at least one of $R_1$ and $R_2$ is $(C_1-C_{12})$alkyl.

The invention also provides processes and intermediates disclosed herein that are useful for preparing compounds of formula (I), or salts thereof.

BRIEF DESCRIPTION OF THE FIGURES

FIG. 3A. $^1$H NMR spectrum of 1 wt. % 1 blended in PAO. FIG. 3B. $^1$H NMR spectrum of 1 wt. % 1 blended in PAO after being exposed to 100° C. for 2 h, revealing preservation of the methine peak. FIG. 3C. $^1$H NMR spectrum of 1 wt. % 1 blended in PAO after being exposed to 200° C. for 2 h, showing decomposition of the parent compound as indicated by the methine peak absence.

FIG. 5A. Thermogram of 1 displaying step-wise weight loss. FIG. 5B. Gas phase FTIR spectra of 1 displaying significant $CO_2$ evolution (doublet near 2356 $cm^{-1}$) in addition to multiple carbonyl stretches (1777 and 1797 $cm^{-1}$), an —OH stretch (3581 $cm^{-1}$) and potential C—O absorbance (1183 $cm^{-1}$).

FIG. 7A. Initial 5 decomposition generating a near identical spectra as 1 with a significant $CO_2$ evolution in addition to C=O, C—O, and —O—H stretches (onset ~184° C.). FIG. 7B. Second step of 5 decomposition with a large aliphatic content, carbonyl stretch and gas-phase hydroxyl stretching, indicative of stearic acid volatilization (onset ~230° C.). FIG. 7C. Volatilization of pure stearic acid for comparison (onset ~203° C.).

FIG. 8A. Gas phase FTIR spectra of 3 revealing significant aliphatic C—H stretching at 2933 and 2863 $cm^{-1}$, $CO_2$ stretches, and carbonyl stretch at 1751 $cm^{-1}$. FIG. 8B. Gas phase FTIR spectra of 4 showing similar FTIR spectra as 3.

FIG. 9A shows the results over 120 minutes; and FIG. 9B shows the results over 20 minutes.

FIG. 10A shows β-ester pyrolysis of 6 releasing isobutylene; FIG. 10B shows 2nd step of 6 decomposition cascade, which is near identical to the degradation of 5; and FIG. 10C shows stearic acid volatilization as indicated by the signature aliphatic, carbonyl, and hydroxyl stretches.

DETAILED DESCRIPTION

Figure 1:
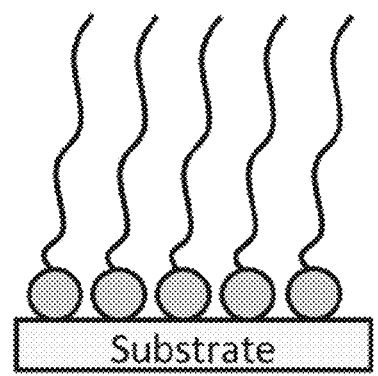
FIG. 1. Cartoon of FMs interacting with metal surface (substrate) generating a monolayer that provides sufficient lubricity, preventing direct metal/metal contact.

Described herein are friction modifiers that provide thermally triggered, controlled release performance overtime and that are simple to synthesize and formulate. As used herein, the term friction modifier refers to any material or materials that can alter the coefficient of friction of a surface lubricated by any lubricant or fluid containing such material(s). For both engine and industrial lubricant applications, it is important to have a lubricant formulation with a low friction coefficient. Fluids with low friction coefficients exhibit low frictional loss during lubrication, and therefore, provide improved energy and/or fuel efficiency of such formulated lubricants.

As discussed in the Examples, fatty acids (e.g., stearic acid) were incorporated into themocleavable systems; these compounds showed useful friction modifying performance over a prolonged timeframe. Specifically, experiments measuring the friction modifying capabilities in high frequency reciprocating rig (HFRR) analyses were performed using the compounds and compositions described herein. Certain compounds (e.g., compound (5) and compound (6)) showed friction modifying capabilities superior to a substantial majority of other additives. For example, compound (6) was shown by Fourier transform infrared spectroscopy coupled with thermogravimetric analysis to thermally degrade step-wise into a compound (5) intermediate, and subsequently stearic acid, upon being exposed to temperatures greater than or equal to 200° C. within the envelope. Moreover, both compound (5) and stearic acid have been shown to possess friction modifying capabilities, as exhibited by low friction coefficients, whereas compound (6) reduces friction only after exposure to test temperatures greater than 150° C. The friction coefficient obtained for compound (5) is significantly lower than values obtained by most commercially available additives.

The lubricating oil compositions described herein, which comprise a friction modifier of the invention, may provide enhanced engine protection. Additionally, these compositions may reduce consumer costs with improved lubricant lifetime and fuel economy.

Compositions of the Invention

Accordingly, certain embodiments of the invention provide a lubricating oil composition comprising a lubricating oil base stock and a compound of formula (I):

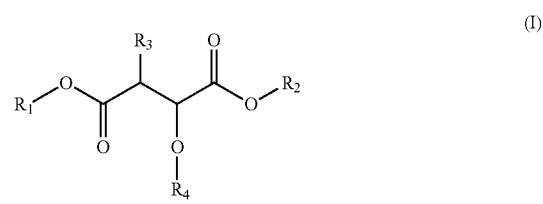

wherein, $R_1$ and $R_2$ are each independently H, $(C_1\text{-}_{12})$ alkyl, benzyl or phenethyl; $R_3$ is H or $OR^a$, wherein $R^a$ is $(C_1\text{-}C_{20})$alkyl, $(C_1\text{-}C_{20})$alkanoyl, $(C_2\text{-}C_{20})$alkenyl or $(C_3\text{-}$ $C_{20}$)alkenoyl; and $R_4$ is $(C_1$-$C_{20})$alkyl, $(C_1$-$C_{20})$alkanoyl, $(C_2$-$C_{20})$alkenyl or $(C_3$-$C_{20})$alkenoyl; or a salt thereof.

In certain embodiments, $R_1$ is H.

In certain embodiments, $R_1$ is $(C_1$-$C_{12})$alkyl. In certain embodiments, $R_1$ is $(C_1$-$C_6)$alkyl.

In certain embodiments, $R_1$ is methyl, ethyl, propyl, isopropyl, butyl, isobutyl, sec-butyl or tert-butyl. In certain embodiments, $R_1$ is ethyl. In certain embodiments, $R_1$ is tert-butyl.

In certain embodiments, $R_1$ is benzyl.

In certain embodiments, $R_2$ is H.

In certain embodiments, $R_2$ is $(C_1$-$C_{12})$alkyl. In certain embodiments, $R_2$ is $(C_1$-$C_6)$alkyl.

In certain embodiments, $R_2$ is methyl, ethyl, propyl, isopropyl, butyl, isobutyl, sec-butyl or tert-butyl. In certain embodiments, $R_2$ is ethyl. In certain embodiments, $R_2$ is tert-butyl.

In certain embodiments, $R_2$ is benzyl.

In certain embodiments, $R_1$ and $R_2$ are each H.

In certain embodiments, $R_1$ and $R_2$ are each $(C_1$-$C_{12})$alkyl. In certain embodiments, $R_1$ and $R_2$ are each $(C_1$-$C_6)$alkyl. In certain embodiments, $R^1$ and $R^2$ are each ethyl. In certain embodiments, $R_1$ and $R_2$ are each tert-butyl.

In certain embodiments, $R_1$ and $R_2$ are each benzyl.

In certain embodiments, $R_3$ is H.

In certain embodiments, $R_3$ is $OR^a$, wherein $R^a$ is $(C_1$-$C_{20})$alkyl, $(C_1$-$C_{20})$alkanoyl, $(C_2$-$C_{20})$alkenyl or $(C_3$-$C_{20})$alkenoyl.

In certain embodiments, $R_3$ is $OR^a$, wherein $R^a$ is $(C_1$-$C_{20})$alkyl. In certain embodiments, $R^a$ is $(C_2$-$C_{20})$alkyl. In certain embodiments, $R^a$ is $(C_4$-$C_{20})$alkyl. In certain embodiments, $R^a$ is $(C_6$-$C_{20})$alkyl. In certain embodiments, $R^a$ is $(C_8$-$C_{20})$alkyl. In certain embodiments, $R^a$ is $(C_{10}$-$C_{20})$alkyl. In certain embodiments, $R^a$ is $(C_1)$alkyl, $(C_2)$alkyl, $(C_3)$alkyl, $(C_4)$alkyl, $(C_5)$alkyl, $(C_6)$alkyl, $(C_7)$alkyl, $(C_8)$alkyl, $(C_9)$alkyl, $(C_{10})$alkyl, $(C_{11})$alkyl, $(C_{12})$alkyl, $(C_{13})$alkyl, $(C_{14})$alkyl, $(C_{15})$alkyl, $(C_{16})$alkyl, $(C_{17})$alkyl, $(C_{18})$alkyl, $(C_{19})$alkyl or $(C_{20})$alkyl. In certain embodiments, $R^a$ is $(C_1)$alkyl. In certain embodiments, $R^a$ is $(C_{12})$alkyl. In certain embodiments, $R^a$ is $(C_{14})$alkyl. In certain embodiments, $R^a$ is $(C_{16})$alkyl. In certain embodiments, $R^a$ is $(C_{18})$alkyl.

In certain embodiments, $R_3$ is $OR^a$, wherein $R^a$ is $(C_1$-$C_{20})$alkanoyl. In certain embodiments, $R^a$ is $(C_2$-$C_{20})$alkanoyl. In certain embodiments, $R^a$ is $(C_4$-$C_{20})$alkanoyl. In certain embodiments, $R^a$ is $(C_6$-$C_{20})$alkanoyl. In certain embodiments, $R^a$ is $(C_8$-$C_{20})$alkanoyl. In certain embodiments, $R^a$ is $(C_{10}$-$C_{20})$alkanoyl. In certain embodiments, $R^a$ is $(C_1)$alkanoyl, $(C_2)$alkanoyl, $(C_3)$alkanoyl, $(C_4)$alkanoyl, $(C_5)$alkanoyl, $(C_6)$alkanoyl, $(C_7)$alkanoyl, $(C_8)$alkanoyl, $(C_9)$alkanoyl, $(C_{10})$alkanoyl, $(C_{11})$alkanoyl, $(C_{12})$alkanoyl, $(C_{13})$alkanoyl, $(C_{14})$alkanoyl, $(C_{15})$alkanoyl, $(C_{16})$alkanoyl, $(C_{17})$alkanoyl, $(C_{18})$alkanoyl, $(C_{19})$alkanoyl or $(C_{20})$alkanoyl. In certain embodiments, $R^a$ is $(C_1)$alkanoyl. In certain embodiments, $R^a$ is $(C_{12})$alkanoyl. In certain embodiments, $R^a$ is $(C_{14})$alkanoyl. In certain embodiments, $R^a$ is $(C_{16})$alkanoyl. In certain embodiments, $R^a$ is $(C_{18})$alkanoyl.

In certain embodiments, $R_3$ is $OR^a$, wherein $R^a$ is $(C_2$-$C_{20})$alkenyl. In certain embodiments, $R^a$ is $(C_4$-$C_{20})$alkenyl. In certain embodiments, $R^a$ is $(C_6$-$C_{20})$alkenyl. In certain embodiments, $R^a$ is $(C_8$-$C_{20})$alkenyl. In certain embodiments, $R^a$ is $(C_{10}$-$C_{20})$alkenyl. In certain embodiments, $R^a$ is $(C_2)$alkenyl, $(C_3)$alkenyl, $(C_4)$alkenyl, $(C_5)$alkenyl, $(C_6)$alkenyl, $(C_7)$alkenyl, $(C_8)$alkenyl, $(C_9)$alkenyl, $(C_{10})$alkenyl, $(C_{11})$alkenyl, $(C_{12})$alkenyl, $(C_{13})$alkenyl, $(C_{14})$alkenyl, $(C_{15})$alkenyl, $(C_{16})$alkenyl, $(C_{17})$alkenyl, $(C_{18})$alkenyl, $(C_{19})$alkenyl or $(C_{20})$alkenyl. In certain embodiments, $R^a$ is $(C_{12})$alkenyl. In certain embodiments, $R^a$ is $(C_{14})$alkenyl. In certain embodiments, $R^a$ is $(C_{16})$alkenyl. In certain embodiments, $R^a$ is $(C_{18})$alkenyl.

In certain embodiments, $R_3$ is $OR^a$, wherein $R^a$ is $(C_3$-$C_{20})$alkenoyl. In certain embodiments, $R^a$ is $(C_6$-$C_{20})$alkenoyl. In certain embodiments, $R^a$ is $(C_8$-$C_{20})$alkenoyl. In certain embodiments, $R^a$ is $(C_{10}$-$C_{20})$alkenoyl. In certain embodiments, $R^a$ is $(C_3)$alkenoyl, $(C_4)$alkenoyl, $(C_5)$alkenoyl, $(C_6)$alkenoyl, $(C_7)$alkenoyl, $(C_8)$alkenoyl, $(C_9)$alkenoyl, $(C_{10})$alkenoyl, $(C_{11})$alkenoyl, $(C_{12})$alkenoyl, $(C_{13})$alkenoyl, $(C_{14})$alkenoyl, $(C_{15})$alkenoyl, $(C_{16})$alkenoyl, $(C_{17})$alkenoyl, $(C_{18})$alkenoyl, $(C_{19})$alkenoyl or $(C_{20})$alkenoyl. In certain embodiments, $R^a$ is $(C_{12})$alkenoyl. In certain embodiments, $R^a$ is $(C_{14})$alkenoyl. In certain embodiments, $R^a$ is $(C_{16})$alkenoyl. In certain embodiments, $R^a$ is $(C_{18})$alkenoyl.

In certain embodiments, $R_3$ is $OR^a$, wherein $R^a$ is derivable from an unsaturated fatty acid. In certain embodiments, $R^a$ is derivable from crotonic acid, sapienic acid, gadoleic acid, eicosenoic acid, arachidonic acid, α-linolenic acid, stearidonic acid, eicosapentaenoic acid, γ-linolenic acid, dihomo-γ-linolenic acid, docosatetraenoic acid, vaccenic acid, paullinic acid, elaidic acid, gondoic acid, mead acid, monolein, myristoleic acid, palmitoleic acid, oleic acid, linoleic acid, pinolenic acid, eleostearic acid or eicosatrienoic acid. In certain embodiments, $R^a$ is derivable from oleic acid.

In certain embodiments, $R_4$ is $(C_1$-$C_{20})$alkyl. In certain embodiments, $R_4$ is $(C_2$-$C_{20})$alkyl. In certain embodiments, $R_4$ is $(C_4$-$C_{20})$alkyl. In certain embodiments, $R_4$ is $(C_6$-$C_{20})$alkyl. In certain embodiments, $R_4$ is $(C_8$-$C_{20})$alkyl. In certain embodiments, $R_4$ is $(C_{10}$-$C_{20})$alkyl. In certain embodiments, $R_4$ is $(C_1)$alkyl, $(C_2)$alkyl, $(C_3)$alkyl, $(C_4)$alkyl, $(C_5)$alkyl, $(C_6)$alkyl, $(C_7)$alkyl, $(C_8)$alkyl, $(C_9)$alkyl, $(C_{10})$alkyl, $(C_{11})$alkyl, $(C_{12})$alkyl, $(C_{13})$alkyl, $(C_{14})$alkyl, $(C_{15})$alkyl, $(C_{16})$alkyl, $(C_{17})$alkyl, $(C_{18})$alkyl, $(C_{19})$alkyl or $(C_{20})$alkyl. In certain embodiments, $R_4$ is $(C_1)$alkyl. In certain embodiments, $R_4$ is $(C_{12})$alkyl. In certain embodiments, $R_4$ is $(C_{14})$alkyl. In certain embodiments, $R_4$ is $(C_{16})$alkyl. In certain embodiments, $R_4$ is $(C_{18})$alkyl.

In certain embodiments, $R_4$ is $(C_1$-$C_{20})$alkanoyl. In certain embodiments, $R_4$ is $(C_2$-$C_{20})$alkanoyl. In certain embodiments, $R_4$ is $(C_4$-$C_{20})$alkanoyl. In certain embodiments, $R_4$ is $(C_6$-$C_{20})$alkanoyl. In certain embodiments, $R_4$ is $(C_8$-$C_{20})$alkanoyl. In certain embodiments, $R_4$ is $(C_{10}$-$C_{20})$alkanoyl. In certain embodiments, $R_4$ is $(C_1)$alkanoyl, $(C_2)$alkanoyl, $(C_3)$alkanoyl, $(C_4)$alkanoyl, $(C_5)$alkanoyl, $(C_6)$alkanoyl, $(C_7)$alkanoyl, $(C_8)$alkanoyl, $(C_9)$alkanoyl, $(C_{10})$alkanoyl, $(C_{11})$alkanoyl, $(C_{12})$alkanoyl, $(C_{13})$alkanoyl, $(C_{14})$alkanoyl, $(C_{15})$alkanoyl, $(C_{16})$alkanoyl, $(C_{17})$alkanoyl, $(C_{18})$alkanoyl, $(C_{19})$alkanoyl or $(C_{20})$alkanoyl. In certain embodiments, $R_4$ is $(C_1)$alkanoyl. In certain embodiments, $R_4$ is $(C_{12})$alkanoyl. In certain embodiments, $R_4$ is $(C_{14})$alkanoyl. In certain embodiments, $R_4$ is $(C_{16})$alkanoyl. In certain embodiments, $R_4$ is $(C_{18})$alkanoyl.

In certain embodiments, $R_4$ is $(C_2$-$C_{20})$alkenyl. In certain embodiments, $R_4$ is $(C_4$-$C_{20})$alkenyl. In certain embodiments, $R_4$ is $(C_6$-$C_{20})$alkenyl. In certain embodiments, $R_4$ is $(C_8$-$C_{20})$alkenyl. In certain embodiments, $R_4$ is $(C_{10}$-$C_{20})$alkenyl. In certain embodiments, $R_4$ is $(C_2)$alkenyl, $(C_3)$alkenyl, $(C_4)$alkenyl, $(C_5)$alkenyl, $(C_6)$alkenyl, $(C_7)$alkenyl, $(C_8)$alkenyl, $(C_9)$alkenyl, $(C_{10})$alkenyl, $(C_{11})$alkenyl, $(C_{12})$alkenyl, $(C_{13})$alkenyl, $(C_{14})$alkenyl, $(C_{15})$alkenyl, $(C_{16})$alkenyl, $(C_{17})$alkenyl, $(C_{18})$alkenyl, $(C_{19})$alkenyl or $(C_{20})$alkenyl. In certain embodiments, $R_4$ is $(C_{12})$alkenyl. In certain embodiments, $R_4$ is $(C_{14})$alkenyl. In certain embodiments, $R_4$ is $(C_{16})$alkenyl. In certain embodiments, $R_4$ is $(C_{18})$alkenyl.

In certain embodiments, $R_4$ is $(C_3-C_{20})$alkenoyl. In certain embodiments, $R_4$ is $(C_6-C_{20})$alkenoyl. In certain embodiments, $R_4$ is $(C_8-C_{20})$alkenoyl. In certain embodiments, $R_4$ is $(C_{10}-C_{20})$alkenoyl. In certain embodiments, $R_4$ is $(C_3)$alkenoyl, $(C_4)$alkenoyl, $(C_5)$alkenoyl, $(C_6)$alkenoyl, $(C_7)$alkenoyl, $(C_8)$alkenoyl, $(C_9)$alkenoyl, $(C_{10})$alkenoyl, $(C_{11})$alkenoyl, $(C_{12})$alkenoyl, $(C_{13})$alkenoyl, $(C_{14})$alkenoyl, $(C_{15})$alkenoyl, $(C_{16})$alkenoyl, $(C_{17})$alkenoyl, $(C_{18})$alkenoyl, $(C_{19})$alkenoyl or $(C_{20})$alkenoyl. In certain embodiments, $R_4$ is $(C_{12})$alkenoyl. In certain embodiments, $R_4$ is $(C_{14})$alkenoyl. In certain embodiments, $R_4$ is $(C_{16})$alkenoyl. In certain embodiments, $R_4$ is $(C_{18})$alkenoyl.

In certain embodiments, $R_4$ is derivable from an unsaturated fatty acid. In certain embodiments, $R_4$ is derivable from crotonic acid, sapienic acid, gadoleic acid, eicosenoic acid, arachidonic acid, α-linolenic acid, stearidonic acid, eicosapentaenoic acid, γ-linolenic acid, dihomo-γ-linolenic acid, docosatetraenoic acid, vaccenic acid, paullinic acid, elaidic acid, gondoic acid, mead acid, monolein, myristoleic acid, palmitoleic acid, oleic acid, linoleic acid, pinolenic acid, eleostearic acid or eicosatrienoic acid. In certain embodiments, $R_4$ is derivable from oleic acid.

In certain embodiments, the compound of formula (I) is a compound of formula (Ia), (Ib), (Ic), (Id) or (Ie), as described below.

In certain embodiments, the compound of formula (I) is selected from the group consisting of:

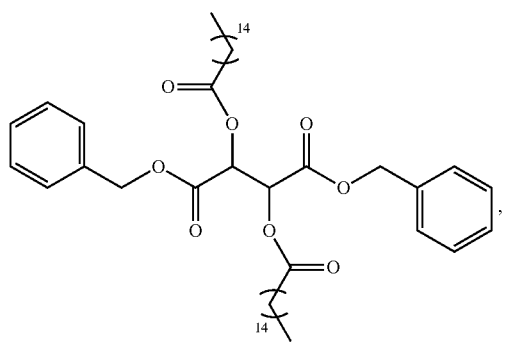
,

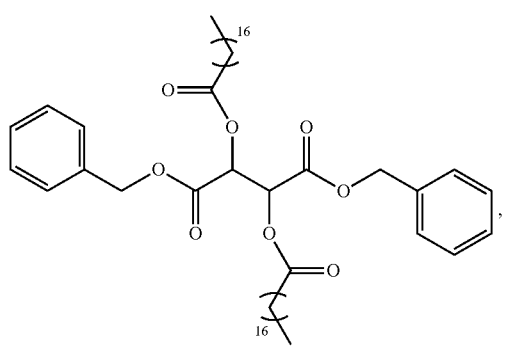
,

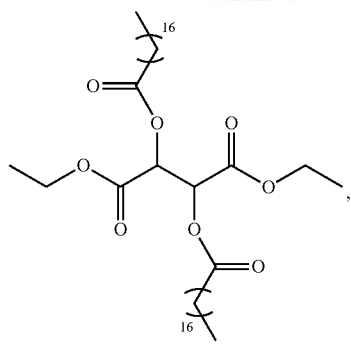
,

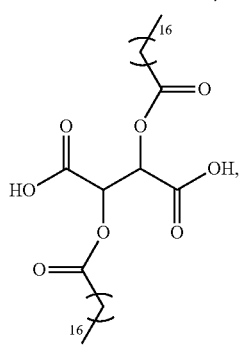

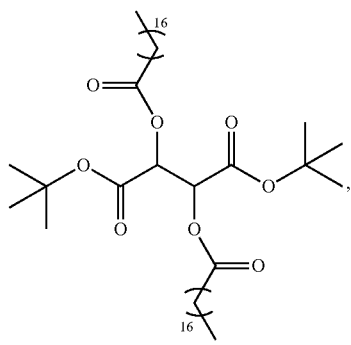
,

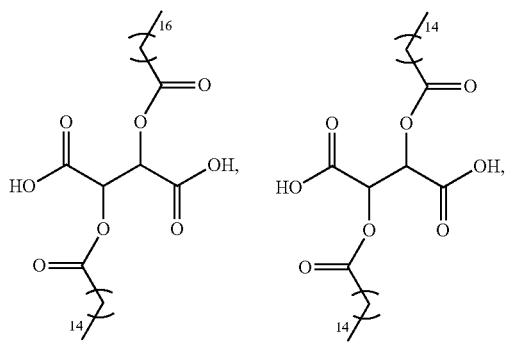

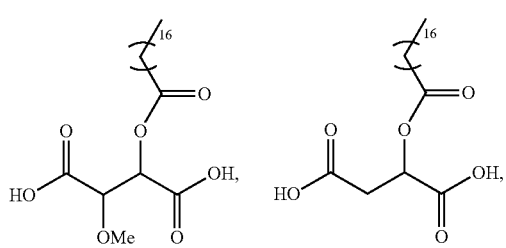

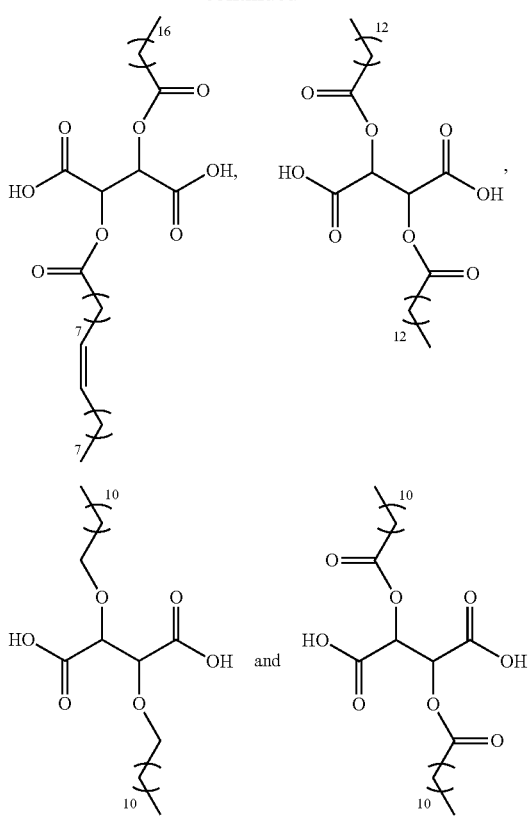
and salts thereof.
In certain embodiments, the compound of formula (I) is selected from the group consisting of:
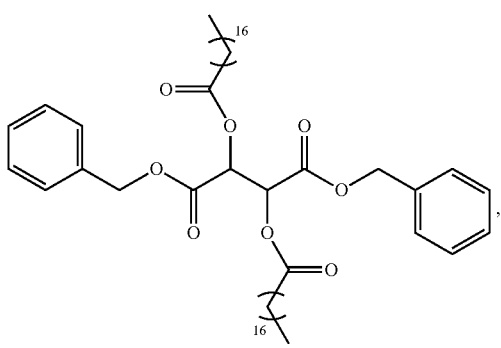
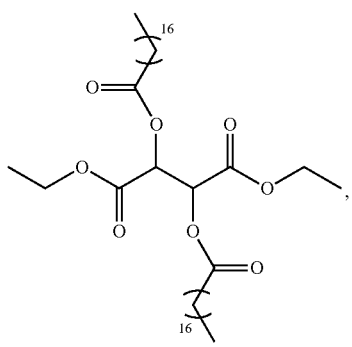
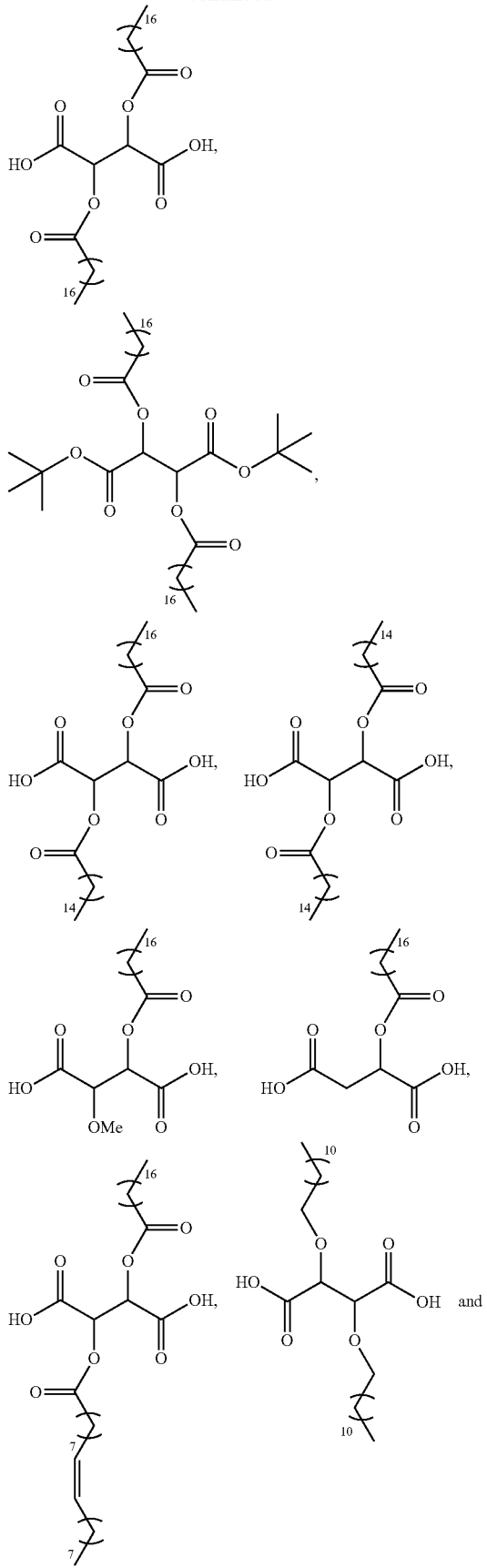

-continued

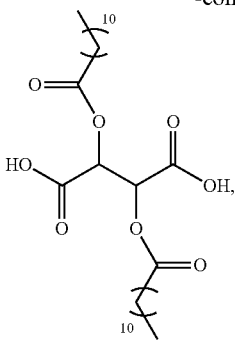

and salts thereof.

In certain embodiments, the compound of formula (I) is:

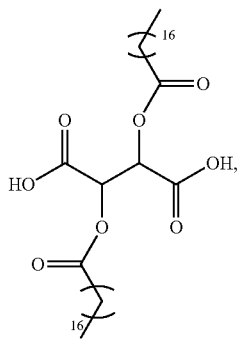

or a salt thereof.

In certain embodiments, the compound of formula (I) is:

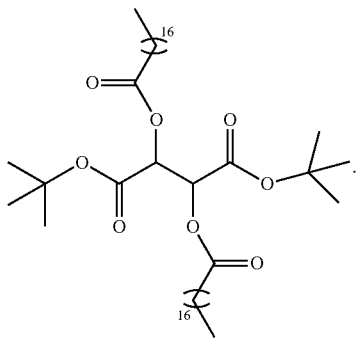

As certain compounds of formula (I) may have different thermal release temperatures, it may be advantageous to include a mixture of compounds of formula (I) in a lubricating oil composition described herein. Specifically, by mixing compounds of formula (I), a smoother progression of thermal release through the temperature range of the operating equipment may be obtained. Additionally, different types of engines/mechanical components may have different operating temperatures. Accordingly, in certain embodiments of the invention, a lubricating oil composition as described herein, comprises a mixture of compounds of formula (I) (e.g., two or more compounds of formula (I)), or a salts thereof. In certain embodiments of the invention, a lubricating oil composition as described herein, comprises a mixture of compounds of formula (I), or a salts thereof, wherein the compounds of formula (I) have different thermal release temperatures.

In certain embodiments of the invention, a lubricating oil composition as described herein, comprises one or more compounds of formula (I), or a salt thereof, in an amount of from about 0.01 weight percent to about 5 weight percent, based on the total weight of the lubricating oil composition. In certain embodiments, the one or more compounds of formula (I), or a salt thereof, is present in an amount of from about 0.1 weight percent to about 2.5 weight percent, based on the total weight of the lubricating oil composition. In certain embodiments, the one or more compounds of formula (I), or a salt thereof, is present in an amount of from about 0.1 weight percent to about 1.5 weight percent, based on the total weight of the lubricating oil composition. In certain embodiments, the one or more compounds of formula (I), or a salt thereof, is present in an amount of from about 0.1 weight percent to about 1 weight percent, based on the total weight of the lubricating oil composition.

In certain embodiments of the invention, a lubricating oil composition as described herein, comprises an oil base stock in an amount of from about 70 weight percent to about 95 weight percent, based on the total weight of the lubricating oil composition.

Certain embodiments of the invention provide a lubricating oil composition prepared by combining a lubricating oil base stock and a compound of formula (I), or a salt thereof, as described herein.

In certain embodiments, the lubricating oil composition further comprises one or more lubricating performance additives.

In certain embodiments, the lubricating performance additive is selected from the group consisting of an anti-wear additive, viscosity modifier, antioxidant, detergent, dispersant, pour point depressant, corrosion inhibitor, metal deactivator, seal compatibility additive, anti-foam agent, other friction modifier and anti-rust additive/inhibitor.

Lubricating Oil Base Stocks

As described below, lubricating base oils are known in the art. Lubricating base oils that are useful in the present disclosure include, but are not limited to, natural oils, synthetic oils, unconventional oils, and mixtures thereof. Unconventional oils may be unrefined, refined or rerefined (i.e., reclaimed or reprocessed oil). Unrefined oils are those obtained directly from a natural or synthetic source and used without added purification. These include shale oil obtained directly from retorting operations, petroleum oil obtained directly from primary distillation, and ester oil obtained directly from an esterification process. Refined oils are similar to the oils discussed for unrefined oils except refined oils are subjected to one or more purification steps to improve at least one lubricating oil property. One skilled in the art is familiar with many purification processes. These processes include solvent extraction, secondary distillation, acid extraction, base extraction, filtration, and percolation. Rerefined oils are obtained by processes analogous to refined oils but using an oil that has been previously used as a feed stock.

Groups I, II, III, IV and V are broad base oil stock categories developed and defined by the American Petroleum Institute (API Publication 1509; www.API.org) to create guidelines for lubricant base oils. Group I base stocks have a viscosity index of between about 80 to 120 and contain greater than about 0.03% sulfur and/or less than about 90% saturates. Group II base stocks have a viscosity index of between about 80 to 120, and contain less than or equal to about 0.03% sulfur and greater than or equal to about 90% saturates. Group III stocks have a viscosity index greater than about 120 and contain less than or equal to about 0.03% sulfur and greater than about 90% saturates. Group IV includes polyalphaolefins (PAO). Group V base stock includes base stocks not included in Groups I-IV. The table below summarizes properties of each of these five groups.

| Base Oil Properties | | | |
|---|---|---|---|
| | Saturates | Sulfur | Viscosity Index |
| Group I | <90 and/or | >0.03% and | ≥80 and <120 |
| Group II | ≥90 and | ≤0.03% and | ≥80 and <120 |
| Group III | ≥90 and | ≤0.03% and | ≥120 |
| Group IV | polyalphaolefins (PAO) | | |
| Group V | All other base oil stocks not included in Groups I, II, III or IV | | |

Accordingly, in certain embodiments of the invention, the lubricating oil base stock comprises a Group I, Group II, Group III, Group IV or Group V base oil.

Natural oils include animal oils, vegetable oils (castor oil and lard oil, for example), and mineral oils. Animal and vegetable oils possessing favorable thermal oxidative stability can be used. Mineral oil is a specific example of a natural oil. Mineral oils vary widely as to their crude source, for example, as to whether they are paraffinic, naphthenic, or mixed paraffinic-naphthenic. Oils derived from coal or shale are also useful. Natural oils vary also as to the method used for their production and purification, for example, their distillation range and whether they are straight run or cracked, hydrorefined, or solvent extracted.

Group II and/or Group III hydroprocessed or hydrocracked basestocks, including synthetic oils such as polyalphaolefins, alkyl aromatics and synthetic esters are also well known basestock oils.

Synthetic oils include hydrocarbon oil. Hydrocarbon oils include oils such as polymerized and interpolymerized olefins (polybutylenes, polypropylenes, propylene isobutylene copolymers, ethylene-olefin copolymers, and ethylene-alphaolefin copolymers, for example). Polyalphaolefin (PAO) oil base stocks are commonly used synthetic hydrocarbon oil. By way of example, PAOs derived from $C_8$, $C_{10}$, $C_{12}$, $C_{14}$ olefins or mixtures thereof may be utilized. See U.S. Pat. Nos. 4,956,122; 4,827,064; and 4,827,073.

The number average molecular weights of the PAOs, which are known materials and generally available on a major commercial scale from suppliers such as ExxonMobil Chemical Company, Chevron Phillips Chemical Company, BP, and others, typically vary from about 250 to about 3,000, although PAO's may be made in viscosities up to about 150 cSt (100° C.). The PAOs are typically comprised of relatively low molecular weight hydrogenated polymers or oligomers of alphaolefins which include, but are not limited to, $C_2$ to about $C_{32}$ alphaolefins with the $C_8$ to about $C_{16}$ alphaolefins, such as 1-octene, 1-decene, 1-dodecene and the like, being specific alphaolefins. In certain embodiments, a polyalphaolefin may be poly-1-octene, poly-1-decene and poly-1-dodecene and mixtures thereof and mixed olefin-derived polyolefins. However, the dimers of higher olefins in the range of $C_{14}$ to $C_{18}$ may be used to provide low viscosity base stocks of acceptably low volatility. Depending on the viscosity grade and the starting oligomer, the PAOs may be predominantly trimers and tetramers of the starting olefins, with minor amounts of the higher oligomers, having a viscosity range of 1.5 to 12 cSt. PAO fluids of particular use may include 3.0 cSt, 3.4 cSt, and/or 3.6 cSt and combinations thereof. Mixtures of PAO fluids having a viscosity range of 1.5 to approximately 150 cSt or more may be used if desired.

The PAO fluids may be conveniently made by the polymerization of an alphaolefin in the presence of a polymerization catalyst such as the Friedel-Crafts catalysts including, for example, aluminum trichloride, boron trifluoride or complexes of boron trifluoride with water, alcohols such as ethanol, propanol or butanol, carboxylic acids or esters such as ethyl acetate or ethyl propionate. For example the methods disclosed by U.S. Pat. No. 4,149,178 or 3,382,291 may be conveniently used herein. Other descriptions of PAO synthesis are found in the following U.S. Pat. Nos. 3,742,082; 3,769,363; 3,876,720; 4,239,930; 4,367,352; 4,413,156; 4,434,408; 4,910,355; 4,956,122; and 5,068,487. The dimers of the $C_{14}$ to $C_{18}$ olefins are described in U.S. Pat. No. 4,218,330.

Other useful lubricant oil base stocks include wax isomerate base stocks and base oils, comprising hydroisomerized waxy stocks (e.g. waxy stocks such as gas oils, slack waxes, fuels hydrocracker bottoms, etc.), hydroisomerized Fischer-Tropsch waxes, Gas-to-Liquids (GTL) base stocks and base oils, and other wax isomerate hydroisomerized base stocks and base oils, or mixtures thereof Fischer-Tropsch waxes, the high boiling point residues of Fischer-Tropsch synthesis, are highly paraffinic hydrocarbons with very low sulfur content. The hydroprocessing used for the production of such base stocks may use an amorphous hydrocracking/hydroisomerization catalyst, such as one of the specialized lube hydrocracking (LHDC) catalysts or a crystalline hydrocracking/hydroisomerization catalyst, e.g., a zeolitic catalyst. For example, one useful catalyst is ZSM-48 as described in U.S. Pat. No. 5,075,269, the disclosure of which is incorporated herein by reference in its entirety. Processes for making hydrocracked/hydroisomerized distillates and hydrocracked/hydroisomerized waxes are described, for example, in U.S. Pat. Nos. 2,817,693; 4,975,177; 4,921,594 and 4,897,178 as well as in British Patent Nos. 1,429,494; 1,350,257; 1,440,230 and 1,390,359. Each of the aforementioned patents is incorporated herein in their entirety. Particularly favorable processes are described in European Patent Application Nos. 464546 and 464547, also incorporated herein by reference. Processes using Fischer-Tropsch wax feeds are described in U.S. Pat. Nos. 4,594,172 and 4,943,672, the disclosures of which are incorporated herein by reference in their entirety.

Gas-to-Liquids (GTL) base oils, Fischer-Tropsch wax derived base oils, and other wax-derived hydroisomerized (wax isomerate) base oils may be advantageously used in the instant disclosure, and may have useful kinematic viscosities at 100° C. of about 3 cSt to about 50 cSt, specifically about 3 cSt to about 30 cSt, more specifically about 3.5 cSt to about 25 cSt, as exemplified by GTL 4 with kinematic viscosity of about 4.0 cSt at 100° C. and a viscosity index of about 141. These Gas-to-Liquids (GTL) base oils, Fischer-Tropsch wax derived base oils, and other wax-derived hydroisomerized base oils may have useful pour points of about −20° C. or lower, and under some conditions may have advantageous pour points of about −25° C. or lower, with useful pour points of about −30° C. to about −40° C. or lower. Useful compositions of Gas-to-Liquids (GTL) base oils, Fischer-Tropsch wax derived base oils, and wax-derived hydroisomerized base oils are recited in U.S. Pat. Nos. 6,080,301; 6,090,989, and 6,165,949 for example, and are incorporated herein in their entirety by reference.

The hydrocarbyl aromatics can be used as base oil or base oil component and can be any hydrocarbyl molecule that contains at least about 5% of its weight derived from an aromatic moiety such as a benzenoid moiety or naphthenoid moiety, or their derivatives. These hydrocarbyl aromatics include alkyl benzenes, alkyl naphthalenes, alkyl diphenyl oxides, alkyl naphthols, alkyl diphenyl sulfides, alkylated bis-phenol A, alkylated thiodiphenol, and the like. The aromatic can be mono-alkylated, dialkylated, polyalkylated, and the like. The aromatic can be mono- or poly-functionalized. The hydrocarbyl groups can also be comprised of mixtures of alkyl groups, alkenyl groups, alkynyl, cycloalkyl groups, cycloalkenyl groups and other related hydrocarbyl groups. The hydrocarbyl groups can range from about $C_6$ up to about $C_{60}$, with a specific range of about $C_8$ to about $C_{20}$ often being used. A mixture of hydrocarbyl groups is typical, and up to about three such substituents may be present. The hydrocarbyl group can optionally contain sulfur, oxygen, and/or nitrogen containing substituents. The aromatic group can also be derived from natural (petroleum) sources, provided at least about 5% of the molecule is comprised of an above-type aromatic moiety. Viscosities at 100° C. of approximately 3 cSt to about 50 cSt are typical, with viscosities of approximately 3.4 cSt to about 20 cSt often being used for the hydrocarbyl aromatic component. In one embodiment, an alkyl naphthalene where the alkyl group is primarily comprised of 1-hexadecene is used. Other alkylates of aromatics can be advantageously used. Naphthalene or methyl naphthalene, for example, can be alkylated with olefins such as octene, decene, dodecene, tetradecene or higher, mixtures of similar olefins, and the like. Useful concentrations of hydrocarbyl aromatic in a lubricant oil composition can be about 2% to about 25%, specifically about 4% to about 20%, and more specifically about 4% to about 15%, depending on the application.

Alkylated aromatics such as the hydrocarbyl aromatics of the present disclosure may be produced by well-known Friedel-Crafts alkylation of aromatic compounds. See Friedel-Crafts and Related Reactions, Olah, G. A. (ed.), Inter-science Publishers, New York, 1963. For example, an aromatic compound, such as benzene or naphthalene, is alkylated by an olefin, alkyl halide or alcohol in the presence of a Friedel-Crafts catalyst. See Friedel-Crafts and Related Reactions, Vol. 2, part 1, chapters 14, 17, and 18, See Olah, G. A. (ed.), Inter-science Publishers, New York, 1964. Many homogeneous or heterogeneous, solid catalysts are known to one skilled in the art. The choice of catalyst depends on the reactivity of the starting materials and product quality requirements. For example, strong acids such as $AlCl_3$, $BF_3$, or HF may be used.

In some cases, milder catalysts such as $FeCl_3$ or $SnCl_4$ are used. Newer alkylation technology uses zeolites or solid super acids.

Esters comprise a useful base stock. Additive solvency and seal compatibility characteristics may be secured by the use of esters such as the esters of dibasic acids with monoalkanols and the polyol esters of monocarboxylic acids. Esters of the former type include, for example, the esters of dicarboxylic acids such as phthalic acid, succinic acid, alkyl succinic acid, alkenyl succinic acid, maleic acid, azelaic acid, suberic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc.

Particularly useful synthetic esters are those which are obtained by reacting one or more polyhydric alcohols, specifically the hindered polyols (such as the neopentyl polyols, e.g., neopentyl glycol, trimethylol ethane, 2-methyl-2-propyl-1,3-propanediol, trimethylol propane, pentaerythritol and dipentaerythritol) with alkanoic acids containing at least about 4 carbon atoms, specifically $C_5$ to $C_{30}$ acids such as saturated straight chain fatty acids including caprylic acid, capric acid, lauric acid, myristic acid, palmitic acid, stearic acid, arachic acid, and behenic acid, or the corresponding branched chain fatty acids or unsaturated fatty acids such as oleic acid, or mixtures of any of these materials.

Suitable synthetic ester components include the esters of trimethylol propane, trimethylol butane, trimethylol ethane, pentaerythritol and/or dipentaerythritol with one or more monocarboxylic acids containing from about 5 to about 10 carbon atoms. These esters are widely available commercially, for example, the Mobil P-41 and P-51 esters of ExxonMobil Chemical Company.

Also useful are esters derived from renewable material such as coconut, palm, rapeseed, soy, sunflower and the like. These esters may be monoesters, di-esters, polyol esters, complex esters, or mixtures thereof. These esters are widely available commercially, for example, the Mobil P-51 ester of ExxonMobil Chemical Company.

Engine oil formulations containing renewable esters are included in this disclosure. For such formulations, the renewable content of the ester is typically greater than about 70 weight percent, specifically more than about 80 weight percent and most specifically more than about 90 weight percent.

Other useful fluids of lubricating viscosity include non-conventional or unconventional base stocks that have been processed, typically catalytically, or synthesized to provide high performance lubrication characteristics.

Non-conventional or unconventional base stocks/base oils include one or more of a mixture of base stock(s) derived from one or more Gas-to-Liquids (GTL) materials, as well as isomerate/isodewaxate base stock(s) derived from natural wax or waxy feeds, mineral and or non-mineral oil waxy feed stocks such as slack waxes, natural waxes, and waxy stocks such as gas oils, waxy fuels hydrocracker bottoms, waxy raffinate, hydrocrackate, thermal crackates, or other mineral, mineral oil, or even non-petroleum oil derived waxy materials such as waxy materials received from coal liquefaction or shale oil, and mixtures of such base stocks.

GTL materials are materials that are derived via one or more synthesis, combination, transformation, rearrangement, and/or degradation/deconstructive processes from gaseous carbon-containing compounds, hydrogen-containing compounds and/or elements as feed stocks such as hydrogen, carbon dioxide, carbon monoxide, water, methane, ethane, ethylene, acetylene, propane, propylene, propyne, butane, butylenes, and butynes. GTL base stocks and/or base oils are GTL materials of lubricating viscosity that are generally derived from hydrocarbons; for example, waxy synthesized hydrocarbons, that are themselves derived from simpler gaseous carbon-containing compounds, hydrogen-containing compounds and/or elements as feed stocks. GTL base stock(s) and/or base oil(s) include oils boiling in the lube oil boiling range (1) separated/fractionated from synthesized GTL materials such as, for example, by distillation and subsequently subjected to a final wax processing step which involves either or both of a catalytic dewaxing process, or a solvent dewaxing process, to produce lube oils of reduced/low pour point; (2) synthesized wax isomerates, comprising, for example, hydrodewaxed or hydroisomerized cat and/or solvent dewaxed synthesized wax or waxy hydrocarbons; (3) hydrodewaxed or hydroisomerized cat and/or solvent dewaxed Fischer-Tropsch (F-T) material (i.e., hydrocarbons, waxy hydrocarbons, waxes and possible analogous oxygenates); specifically hydrodewaxed or hydroisomerized/followed by cat and/or solvent dewaxing dewaxed F-T waxy hydrocarbons, or hydrodewaxed or hydroisomerized/followed by cat (or solvent) dewaxing dewaxed, F-T waxes, or mixtures thereof.

GTL base stock(s) and/or base oil(s) derived from GTL materials, especially, hydrodewaxed or hydroisomerized/ followed by cat and/or solvent dewaxed wax or waxy feed, specifically F-T material derived base stock(s) and/or base oil(s), are characterized typically as having kinematic viscosities at 100° C. of from about 2 $mm^2/s$ to about 50 $mm^2/s$ (ASTM D445). They are further characterized typically as having pour points of −5° C. to about −40° C. or lower (ASTM D97). They are also characterized typically as having viscosity indices of about 80 to about 140 or greater (ASTM D2270).

In addition, the GTL base stock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stock(s) and/or base oil(s) typically have very low sulfur and nitrogen content, generally containing less than about 10 ppm, and more typically less than about 5 ppm of each of these elements. The sulfur and nitrogen content of GTL base stock(s) and/or base oil(s) obtained from F-T material, especially F-T wax, is essentially nil. In addition, the absence of phosphorous and aromatics make this materially especially suitable for the formulation of low SAP products.

The term GTL base stock and/or base oil and/or wax isomerate base stock and/or base oil is to be understood as embracing individual fractions of such materials of wide viscosity range as recovered in the production process, mixtures of two or more of such fractions, as well as mixtures of one or two or more low viscosity fractions with one, two or more higher viscosity fractions to produce a blend wherein the blend exhibits a target kinematic viscosity.

The GTL material, from which the GTL base stock(s) and/or base oil(s) is/are derived is typically an F-T material (i.e., hydrocarbons, waxy hydrocarbons, wax).

In addition, the GTL base stock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stock(s) and/or base oil(s) and hydrodewaxed, or hydroisomerized/cat (and/or solvent) dewaxed base stock(s) and/or base oil(s) typically have very low sulfur and nitrogen content, generally containing less than about 10 ppm, and more typically less than about 5 ppm of each of these elements. The sulfur and nitrogen content of GTL base stock(s) and/or base oil(s) obtained from F-T material, especially F-T wax, is essentially nil. In addition, the absence of phosphorous and aromatics make this material especially suitable for the formulation of low sulfur, sulfated ash, and phosphorus (low SAP) products.

Base oils for use in the formulated lubricating oils useful in the present disclosure are any of the variety of oils corresponding to API Group I, Group II, Group III, Group IV, and Group V oils and mixtures thereof, specifically API Group II, Group III, Group IV, and Group V oils and mixtures thereof, more specifically the Group III to Group V base oils due to their exceptional volatility, stability, viscometric and cleanliness features. Minor quantities of Group I stock, such as the amount used to dilute additives for blending into formulated lube oil products, can be tolerated but should typically be kept to a minimum, i.e. amounts only associated with their use as diluent/carrier oil for additives used on an "as-received" basis. Even in regard to the Group II stocks, stocks in the higher quality range associated with that stock, i.e. a Group II stock having a viscosity index in the range 100<VI<120, may be particularly useful.

The base oil typically constitutes the major component of the engine oil lubricant composition of the present disclosure and typically is present in an amount ranging from about 50 to about 99 weight percent, specifically from about 70 to about 95 weight percent, and more specifically from about 85 to about 95 weight percent, based on the total weight of the composition. The base oil may be selected from any of the synthetic or natural oils typically used as crankcase lubricating oils for spark-ignited and compression-ignited engines. The base oil conveniently may have a kinematic viscosity, according to ASTM standards, of about 2.5 cSt to about 12 cSt (or $mm^2/s$) at 100° C. In one embodiment the base oil may have a kinetic viscosity of about 2.5 cSt to about 9 cSt (or $mm^2/s$) at 100° C. Mixtures of synthetic and natural base oils may be used. Bi-modal mixtures of Group I, II, III, IV, and/or V base stocks may also be used.

Other Additives

The formulated lubricating oil useful in the present disclosure may additionally contain one or more lubricating oil performance additives, which may include, but are not limited to, anti-wear additives, viscosity modifiers, antioxidants, detergents, dispersants, pour point depressants, corrosion inhibitors, metal deactivators, seal compatibility additives, anti-foam agents, other friction modifiers, anti-rust additives/inhibitors, extreme pressure additives, anti-seizure agents, wax modifiers, fluid-loss additives, lubricity agents, anti-staining agents, chromophoric agents, demulsifiers, emulsifiers, densifiers, wetting agents, gelling agents, tackiness agents, colorants, and others. For a review of many commonly used additives, see Klamann in Lubricants and Related Products, Verlag Chemie, Deerfield Beach, Fla.; ISBN 0-89573-177-0. Reference is also made to "Lubricant Additives" by M. W. Ranney, published by Noyes Data Corporation of Parkridge, N J (1973); see also U.S. Pat. No. 7,704,930 and U.S. Patent Publication No. 2015-0344805, the disclosures of which are incorporated herein in their entirety. These additives are commonly delivered with varying amounts of diluent oil, that may range from 5 weight percent to 50 weight percent.

The types and quantities of performance additives used in combination with the instant disclosure in lubricant compositions are not limited by the examples shown herein as illustrations.

Dispersants

During engine operation, oil-insoluble oxidation byproducts are produced. Dispersants help keep these byproducts in solution, thus diminishing their deposition on metal surfaces. Thus, in certain embodiments of the invention, the lubricating oil composition further comprises one or more dispersants.

Dispersants used in the formulation of the lubricating oil composition may be ashless or ash-forming in nature. One particular dispersant is ashless. So called ashless dispersants are organic materials that form substantially no ash upon combustion. For example, non-metal-containing or borated metal-free dispersants are considered ashless. In contrast, metal-containing detergents discussed above form ash upon combustion.

Suitable dispersants typically contain a polar group attached to a relatively high molecular weight hydrocarbon chain. The polar group typically contains at least one element of nitrogen, oxygen, or phosphorus. Typical hydrocarbon chains contain 50 to 400 carbon atoms.

A particularly useful class of dispersants are the (poly) alkenylsuccinic derivatives, typically produced by the reaction of a long chain hydrocarbyl substituted succinic compound, usually a hydrocarbyl substituted succinic anhydride, with a polyhydroxy or polyamino compound. The long chain hydrocarbyl group constituting the oleophilic portion of the molecule which confers solubility in the oil, is normally a polyisobutylene group. Many examples of this type of dispersant are well known commercially and in the literature. Exemplary U.S. patents describing such dispersants are U.S. Pat. Nos. 3,172,892; 3,2145,707; 3,219,666; 3,316,177; 3,341,542; 3,444,170; 3,454,607; 3,541,012; 3,630,904; 3,632,511; 3,787,374 and 4,234,435. Other types of dispersant are described in U.S. Pat. Nos. 3,036,003; 3,200,107; 3,254,025; 3,275,554; 3,438,757; 3,454,555; 3,565,804; 3,413,347; 3,697,574; 3,725,277; 3,725,480; 3,726,882; 4,454,059; 3,329,658; 3,449,250; 3,519,565; 3,666,730; 3,687,849; 3,702,300; 4,100,082; 5,705,458. A further description of dispersants may be found, for example, in European Patent Application No. 471 071, to which reference is made for this purpose.

Hydrocarbyl-substituted succinic acid and hydrocarbyl-substituted succinic anhydride derivatives are useful dispersants. In particular, succinimide, succinate esters, or succinate ester amides prepared by the reaction of a hydrocarbon-substituted succinic acid compound typically having at least 50 carbon atoms in the hydrocarbon substituent, with at least one equivalent of an alkylene amine are particularly useful.

Succinimides are formed by the condensation reaction between hydrocarbyl substituted succinic anhydrides and amines. Molar ratios can vary depending on the polyamine. For example, the molar ratio of hydrocarbyl substituted succinic anhydride to TEPA can vary from about 1:1 to about 5:1. Representative examples are shown in U.S. Pat. Nos. 3,087,936; 3,172,892; 3,219,666; 3,272,746; 3,322,670; and U.S. Pat. Nos. 3,652,616, 3,948,800; and Canada Patent No. 1,094,044.

Succinate esters are formed by the condensation reaction between hydrocarbyl substituted succinic anhydrides and alcohols or polyols. Molar ratios can vary depending on the alcohol or polyol used. For example, the condensation product of a hydrocarbyl substituted succinic anhydride and pentaerythritol is a useful dispersant.

Succinate ester amides are formed by condensation reaction between hydrocarbyl substituted succinic anhydrides and alkanol amines. For example, suitable alkanol amines include ethoxylated polyalkylpolyamines, propoxylated polyalkylpolyamines and polyalkenylpolyamines such as polyethylene polyamines. One example is propoxylated hexamethylenediamine. Representative examples are shown in U.S. Pat. No. 4,426,305.

The molecular weight of the hydrocarbyl substituted succinic anhydrides used in the preceding paragraphs will typically range between 800 and 2,500 or more. The above products can be post-reacted with various reagents such as sulfur, oxygen, formaldehyde, carboxylic acids such as oleic acid. The above products can also be post reacted with boron compounds such as boric acid, borate esters or highly borated dispersants, to form borated dispersants generally having from about 0.1 to about 5 moles of boron per mole of dispersant reaction product.

Mannich base dispersants are made from the reaction of alkylphenols, formaldehyde, and amines. See U.S. Pat. No. 4,767,551, which is incorporated herein by reference. Process aids and catalysts, such as oleic acid and sulfonic acids, can also be part of the reaction mixture. Molecular weights of the alkylphenols range from 800 to 2,500. Representative examples are shown in U.S. Pat. Nos. 3,697,574; 3,703,536; 3,704,308; 3,751,365; 3,756,953; 3,798,165; and 3,803,039.

Typical high molecular weight aliphatic acid modified Mannich condensation products useful in this disclosure can be prepared from high molecular weight alkyl-substituted hydroxyaromatics or $HNR_2$ group-containing reactants.

Hydrocarbyl substituted amine ashless dispersant additives are well known to one skilled in the art; see, for example, U.S. Pat. Nos. 3,275,554; 3,438,757; 3,565,804; 3,755,433, 3,822,209, and 5,084,197.

Typical dispersants include borated and non-borated succinimides, including those derivatives from mono-succinimides, bis-succinimides, and/or mixtures of mono- and bis-succinimides, wherein the hydrocarbyl succinimide is derived from a hydrocarbylene group such as polyisobutylene having a Mn of from about 500 to about 5000, or from about 1000 to about 3000, or about 1000 to about 2000, or a mixture of such hydrocarbylene groups, often with high terminal vinylic groups. Other specific dispersants include succinic acid-esters and amides, alkylphenol-polyamine-coupled Mannich adducts, their capped derivatives, and other related components.

Polymethacrylate or polyacrylate derivatives are another class of dispersants. These dispersants are typically prepared by reacting a nitrogen containing monomer and a methacrylic or acrylic acid esters containing 5-25 carbon atoms in the ester group. Representative examples are shown in U.S. Pat. Nos. 2,100,993, and 6,323,164. Polymethacrylate and polyacrylate dispersants are normally used as multifunctional viscosity modifiers. The lower molecular weight versions can be used as lubricant dispersants or fuel detergents.

Illustrative dispersants particularly useful in this disclosure include those derived from polyalkenyl-substituted mono- or dicarboxylic acid, anhydride or ester, which dispersant has a polyalkenyl moiety with a number average molecular weight of at least 900 and from greater than 1.3 to 1.7, specifically from greater than 1.3 to 1.6, most specifically from greater than 1.3 to 1.5, functional groups (mono- or dicarboxylic acid producing moieties) per polyalkenyl moiety (a medium functionality dispersant). Functionality (F) can be determined according to the following formula:

$$F=(SAP \times M_n)/((112,200 \times A.I.)-(SAP \times 98))$$

wherein SAP is the saponification number (i.e., the number of milligrams of KOH consumed in the complete neutralization of the acid groups in one gram of the succinic-containing reaction product, as determined according to ASTM D94); $M_n$ is the number average molecular weight of the starting olefin polymer; and A.I. is the percent active ingredient of the succinic-containing reaction product (the remainder being unreacted olefin polymer, succinic anhydride and diluent).

The polyalkenyl moiety of the dispersant may have a number average molecular weight of at least 900, suitably at least 1500, specifically between 1800 and 3000, such as between 2000 and 2800, more specifically from about 2100 to 2500, and most specifically from about 2200 to about 2400. The molecular weight of a dispersant is generally expressed in terms of the molecular weight of the polyalkenyl moiety. This is because the precise molecular weight range of the dispersant depends on numerous parameters including the type of polymer used to derive the dispersant, the number of functional groups, and the type of nucleophilic group employed.

Polymer molecular weight, specifically Mn, can be determined by various known techniques. One convenient method is gel permeation chromatography (GPC), which additionally provides molecular weight distribution information (see W. W. Yau, J. J. Kirkland and D. D. Bly, "Modern Size Exclusion Liquid Chromatography", John Wiley and Sons, New York, 1979). Another useful method for determining molecular weight, particularly for lower molecular weight polymers, is vapor pressure osmometry (e.g., ASTM D3592).

The polyalkenyl moiety in a dispersant typically has a narrow molecular weight distribution (MWD), also referred to as polydispersity, as determined by the ratio of weight average molecular weight ($M_w$) to number average molecular weight ($M_n$). Polymers having a $M_w/M_n$ of less than 2.2, specifically less than 2.0, are most desirable. Suitable polymers have a polydispersity of from about 1.5 to 2.1, specifically from about 1.6 to about 1.8.

Suitable polyalkenes employed in the formation of the dispersants include homopolymers, interpolymers or lower molecular weight hydrocarbons. One family of such polymers comprise polymers of ethylene and/or at least one $C_3$ to $C_2$ alpha-olefin having the formula $H_2C=CHR^1$ wherein $R^1$ is a straight or branched chain alkyl radical comprising 1 to 26 carbon atoms and wherein the polymer contains carbon-to-carbon unsaturation, and a high degree of terminal ethenylidene unsaturation. Typically, such polymers comprise interpolymers of ethylene and at least one alpha-olefin of the above formula, wherein $R^1$ is alkyl of from 1 to 18 carbon atoms, and more specifically is alkyl of from 1 to 8 carbon atoms, and more specifically still of from 1 to 2 carbon atoms.

Another useful class of polymers is polymers prepared by cationic polymerization of monomers such as isobutene and styrene. Common polymers from this class include polyisobutenes obtained by polymerization of a $C_4$ refinery stream having a butene content of 35 to 75% by wt., and an isobutene content of 30 to 60% by wt. A typical source of monomer for making poly-n-butenes is petroleum feedstreams such as Raffinate II. These feedstocks are disclosed in the art such as in U.S. Pat. No. 4,952,739. A specific embodiment utilizes polyisobutylene prepared from a pure isobutylene stream or a Raffinate I stream to prepare reactive isobutylene polymers with terminal vinylidene olefins. Polyisobutene polymers that may be employed are generally based on a polymer chain of from 1500 to 3000.

The dispersant(s) are typically non-polymeric (e.g., mono- or bis-succinimides). Such dispersants can be prepared by conventional processes such as disclosed in U.S. Patent Application Publication No. 2008/0020950, the disclosure of which is incorporated herein by reference.

The dispersant(s) can be borated by conventional means, as generally disclosed in U.S. Pat. Nos. 3,087,936, 3,254,025 and 5,430,105.

Such dispersants may be used in an amount of about 0.01 to 20 weight percent or 0.01 to 10 weight percent, specifically about 0.5 to 8 weight percent, or more specifically 0.5 to 6 weight percent. Or such dispersants may be used in an amount of about 2 to 12 weight percent, specifically about 4 to 10 weight percent, or more specifically 6 to 9 weight percent. On an active ingredient basis, such additives may be used in an amount of about 0.06 to 14 weight percent, specifically about 0.3 to 6 weight percent. The hydrocarbon portion of the dispersant atoms can range from $C_{60}$ to $C_{1000}$, or from $C_{70}$ to $C_{300}$, or from $C_{70}$ to $C_{200}$. These dispersants may contain both neutral and basic nitrogen, and mixtures of both. Dispersants can be end-capped by borates and/or cyclic carbonates.

As used herein, the dispersant concentrations are given on an "as delivered" basis. Typically, the active dispersant is delivered with a process oil. The "as delivered" dispersant typically contains from about 20 weight percent to about 80 weight percent, or from about 40 weight percent to about 60 weight percent, of active dispersant in the "as delivered" dispersant product.

Viscosity Modifiers

In certain embodiments of the invention, viscosity modifiers (also known as viscosity index improvers (VI improvers), and viscosity improvers) may also be included in the lubricant compositions of this disclosure.

Viscosity modifiers provide lubricants with high and low temperature operability. These additives impart shear stability at elevated temperatures and acceptable viscosity at low temperatures.

Suitable viscosity modifiers include high molecular weight hydrocarbons, polyesters and viscosity modifier dispersants that function as both a viscosity modifier and a dispersant. Typical molecular weights of these polymers are between about 10,000 to 1,500,000, more typically about 20,000 to 1,200,000, and even more typically between about 50,000 and 1,000,000.

Examples of suitable viscosity modifiers are linear or star-shaped polymers and copolymers of methacrylate, butadiene, olefins, or alkylated styrenes. Polyisobutylene is a commonly used viscosity modifier. Another suitable viscosity modifier is polymethacrylate (copolymers of various chain length alkyl methacrylates, for example), some formulations of which also serve as pour point depressants. Other suitable viscosity modifiers include copolymers of ethylene and propylene, hydrogenated block copolymers of styrene and isoprene, and polyacrylates (copolymers of various chain length acrylates, for example). Specific examples include styrene-isoprene or styrene-butadiene based polymers of 50,000 to 200,000 molecular weight.

Olefin copolymers are commercially available from Chevron Oronite Company LLC under the trade designation "PARATONE®" (such as "PARATONE® 8921" and "PARATONE® 8941"); from Afton Chemical Corporation under the trade designation "HiTEC®" (such as "HiTEC® 5850B"; and from The Lubrizol Corporation under the trade designation "Lubrizol® 7067C". Hydrogenated polyisoprene star polymers are commercially available from Infineum International Limited, e.g., under the trade designation "SV200" and "SV600". Hydrogenated diene-styrene block copolymers are commercially available from Infineum International Limited, e.g., under the trade designation "SV 50".

The polymethacrylate or polyacrylate polymers can be linear polymers which are available from Evnoik Industries under the trade designation "Viscoplex®" (e.g., Viscoplex 6-954) or star polymers which are available from Lubrizol Corporation under the trade designation Asteric™ (e.g., Lubrizol 87708 and Lubrizol 87725).

Illustrative vinyl aromatic-containing polymers useful in this disclosure may be derived predominantly from vinyl aromatic hydrocarbon monomer. Illustrative vinyl aromatic-containing copolymers useful in this disclosure may be represented by the following general formula:

A-B wherein A is a polymeric block derived predominantly from vinyl aromatic hydrocarbon monomer, and B is a polymeric block derived predominantly from conjugated diene monomer.

The vinyl aromatic-containing polymers or copolymers useful in this disclosure have a weight average molecular weight greater than about 80,000, and a number average molecular weight greater than about 40,000; specifically a weight average molecular weight greater than about 90,000, and a number average molecular weight greater than about 75,000; and more specifically a weight average molecular weight greater than about 100,000 and less than 1,000,000, and a number average molecular weight greater than about 100,000 and less than 1,000,000. The vinyl aromatic-containing polymers or copolymers have an amount of vinyl aromatic content greater than about 10% by weight, or greater than about 20% by weight, or greater than about 30% by weight, of the vinyl aromatic-containing polymer or copolymer. The vinyl aromatic-containing polymers or copolymers have an amount of vinyl aromatic content typically between about 10% and about 50% by weight, more specifically between about 15% and about 40% by weight, and even more specifically between about 20% and about 35% by weight, of the vinyl aromatic-containing polymer or copolymer.

In an embodiment of this disclosure, the viscosity modifiers may be used in an amount of less than about 2.0 weight percent, specifically less than about 1.0 weight percent, and more specifically less than about 0.5 weight percent, based on the total weight of the formulated oil or lubricating oil. Viscosity modifiers are typically added as concentrates, in large amounts of diluent oil.

In another embodiment of this disclosure, the viscosity modifiers may be used in an amount of from 0.05 to about 2.0 weight percent, specifically 0.15 to about 1.0 weight percent, and more specifically 0.25 to about 0.5 weight percent, based on the total weight of the formulated oil or lubricating oil. Or the viscosity modifiers may be used in an amount (total solid polymer content) of from 0.5 to about 2.0 weight percent, specifically 0.8 to about 1.5 weight percent, and more specifically 1.0 to about 1.3 weight percent, based on the total weight of the formulated oil or lubricating oil.

As used herein, the viscosity modifier concentrations are given on an "as delivered" basis. Typically, the active polymer is delivered with a diluent oil. The "as delivered" viscosity modifier typically contains from 20 weight percent to 75 weight percent of an active polymer for polymethacrylate or polyacrylate polymers, or from 8 weight percent to 20 weight percent of an active polymer for olefin copolymers, hydrogenated polyisoprene star polymers, or hydrogenated diene-styrene block copolymers, in the "as delivered" polymer concentrate.

Antiwear Additives

In certain embodiments of the invention, the lubricating oil composition further comprises one or more other antiwear agents. A metal alkylthiophosphate, and more particularly a metal dialkyl dithio phosphate in which the metal constituent is zinc, or zinc dialkyl dithio phosphate (ZDDP), is a useful component of the lubricating oils of this disclosure. ZDDP can be derived from primary alcohols, secondary alcohols or mixtures thereof. ZDDP compounds generally are of the formula:

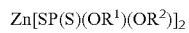

where $R^1$ and $R^2$ are $C_1$-$C_{18}$ alkyl groups, specifically $C_2$-$C_{12}$ alkyl groups. These alkyl groups may be straight chain or branched. Alcohols used in the ZDDP can be 2-propanol, butanol, secondary butanol, pentanols, hexanols such as 4-methyl-2-pentanol, n-hexanol, n-octanol, 2-ethyl hexanol, alkylated phenols, and the like. Mixtures of secondary alcohols or of primary and secondary alcohol can be used. Alkyl aryl groups may also be used.

Zinc dithiophosphates which are commercially available include secondary zinc dithiophosphates such as those available from for example, The Lubrizol Corporation under the trade designations "LZ 677A", "LZ 1095" and "LZ 1371", from for example Chevron Oronite under the trade designation "OLOA 262" and from for example Afton Chemical under the trade designation "HITEC 7169".

The ZDDP is typically used in amounts of from about 0.4 weight percent to about 1.2 weight percent, specifically from about 0.5 weight percent to about 1.0 weight percent, and more specifically from about 0.6 weight percent to about 0.8 weight percent, based on the total weight of the lubricating oil composition, although more or less can often be used advantageously. Typically, the ZDDP is a secondary ZDDP and present in an amount of from about 0.6 to 1.0 weight percent of the total weight of the lubricating oil composition.

Low phosphorus engine oil formulations are included in this disclosure. For such formulations, the phosphorus content is typically less than about 0.12 weight percent specifically less than about 0.10 weight percent and most specifically less than about 0.085 weight percent.

Detergents

In certain embodiments of the invention, the lubricating oil composition further comprises one or more detergents. Illustrative detergents useful in this disclosure include, for example, alkali metal detergents, alkaline earth metal detergents, or mixtures of one or more alkali metal detergents and one or more alkaline earth metal detergents. A typical detergent is an anionic material that contains a long chain hydrophobic portion of the molecule and a smaller anionic or oleophobic hydrophilic portion of the molecule. The anionic portion of the detergent is typically derived from an organic acid such as a sulfur acid, carboxylic acid, phosphorous acid, phenol, or mixtures thereof. The counterion is typically an alkaline earth or alkali metal.

Salts that contain a substantially stochiometric amount of the metal are described as neutral salts and have a total base number (TBN, as measured by ASTM D2896) of from 0 to 80. Many compositions are overbased, containing large amounts of a metal base that is achieved by reacting an excess of a metal compound (a metal hydroxide or oxide, for example) with an acidic gas (such as carbon dioxide). Useful detergents can be neutral, mildly overbased, or highly overbased. These detergents can be used in mixtures of neutral, overbased, highly overbased calcium salicylate, sulfonates, phenates and/or magnesium salicylate, sulfonates, phenates. The TBN ranges can vary from low, medium to high TBN products, including as low as 0 to as high as 600. Mixtures of low, medium, high TBN can be used, along with mixtures of calcium and magnesium metal based detergents, and including sulfonates, phenates, salicylates, and carboxylates. A detergent mixture with a metal ratio of 1, in conjunction of a detergent with a metal ratio of 2, and as high as a detergent with a metal ratio of 5, can be used. Borated detergents can also be used.

Alkaline earth phenates are another useful class of detergent. These detergents can be made by reacting alkaline earth metal hydroxide or oxide (CaO, Ca(OH)$_2$, BaO, Ba(OH)$_2$, MgO, Mg(OH)$_2$, for example) with an alkyl phenol or sulfurized alkylphenol. Useful alkyl groups include straight chain or branched $C_1$-$C_{30}$ alkyl groups, specifically, $C_4$-$C_{20}$ or mixtures thereof. Examples of suitable phenols include isobutylphenol, 2-ethylhexylphenol, nonylphenol, dodecyl phenol, and the like. It should be noted that starting alkylphenols may contain more than one alkyl substituent that are each independently straight chain or branched and can be used from 0.5 to 6 weight percent. When a non-sulfurized alkylphenol is used, the sulfurized product may be obtained by methods well known in the art. These methods include heating a mixture of alkylphenol and sulfurizing agent (including elemental sulfur, sulfur halides such as sulfur dichloride, and the like) and then reacting the sulfurized phenol with an alkaline earth metal base.

Metal salts of carboxylic acids are also useful as detergents. These carboxylic acid detergents may be prepared by reacting a basic metal compound with at least one carboxylic acid and removing free water from the reaction product. These compounds may be overbased to produce the desired TBN level. Detergents made from salicylic acid are one useful class of detergents derived from carboxylic acids. Useful salicylates include long chain alkyl salicylates. One useful family of compositions is of the formula

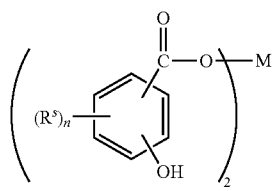

where $R^s$ is an alkyl group having 1 to about 30 carbon atoms, n is an integer from 1 to 4, and M is an alkaline earth metal. Typical $R^s$ groups are alkyl chains of at least $C_{11}$, specifically $C_{13}$ or greater. $R^s$ may be optionally substituted with substituents that do not interfere with the detergent's function. In a specific embodiment, M is calcium, magnesium, or barium. In a more specific embodiment, M is calcium.

Hydrocarbyl-substituted salicylic acids may be prepared from phenols by the Kolbe reaction (see U.S. Pat. No. 3,595,791). The metal salts of the hydrocarbyl-substituted salicylic acids may be prepared by double decomposition of a metal salt in a polar solvent such as water or alcohol.

Alkaline earth metal phosphates are also used as detergents and are known in the art.

Detergents may be simple detergents or what is known as hybrid or complex detergents. The latter detergents can provide the properties of two detergents without the need to blend separate materials. See U.S. Pat. No. 6,034,039.

Typical detergents include calcium phenates, calcium sulfonates, calcium salicylates, magnesium phenates, magnesium sulfonates, magnesium salicylates and other related components (including borated detergents), and mixtures thereof. Typical mixtures of detergents include magnesium sulfonate and calcium salicylate, magnesium sulfonate and calcium sulfonate, magnesium sulfonate and calcium phenate, calcium phenate and calcium salicylate, calcium phenate and calcium sulfonate, calcium phenate and magnesium salicylate, calcium phenate and magnesium phenate.

The lubricating oils of this disclosure exhibit desired properties, e.g., wear control and fuel efficiency, in the presence or absence of a detergent, in particular, the presence or absence of a salicylate detergent or a sulfonate detergent.

The detergent concentration in the lubricating oils of this disclosure can range from about 0.5 to about 6.0 weight percent, specifically about 0.6 to 5.0 weight percent, and more specifically from about 0.8 weight percent to about 4.0 weight percent, based on the total weight of the lubricating oil composition.

As used herein, the detergent concentrations are given on an "as delivered" basis. Typically, the active detergent is delivered with a process oil. The "as delivered" detergent typically contains from about 20 weight percent to about 100 weight percent, or from about 40 weight percent to about 60 weight percent, of active detergent in the "as delivered" detergent product.

Antioxidants

In certain embodiments of the invention, the lubricating oil composition further comprises one or more antioxidants. Antioxidants retard the oxidative degradation of base oils during service. Such degradation may result in deposits on metal surfaces, the presence of sludge, or a viscosity increase in the lubricant. One skilled in the art knows a wide variety of oxidation inhibitors that are useful in lubricating oil compositions. See, Klamann in Lubricants and Related Products, op cite, and U.S. Pat. Nos. 4,798,684 and 5,084,197, for example.

Useful antioxidants include hindered phenols. These phenolic antioxidants may be ashless (metal-free) phenolic compounds or neutral or basic metal salts of certain phenolic compounds. Typical phenolic antioxidant compounds are the hindered phenolics which are the ones which contain a sterically hindered hydroxyl group, and these include those derivatives of dihydroxy aryl compounds in which the hydroxyl groups are in the o- or p-position to each other. Typical phenolic antioxidants include the hindered phenols substituted with $C_6$+ alkyl groups and the alkylene coupled derivatives of these hindered phenols. Examples of phenolic materials of this type 2-t-butyl-4-heptyl phenol; 2-t-butyl-4-octyl phenol; 2-t-butyl-4-dodecyl phenol; 2,6-di-t-butyl-4-heptyl phenol; 2,6-di-t-butyl-4-dodecyl phenol; 2-methyl-6-t-butyl-4-heptyl phenol; and 2-methyl-6-t-butyl-4-dodecyl phenol. Other useful hindered mono-phenolic antioxidants may include for example hindered 2,6-di-alkyl-phenolic proprionic ester derivatives. Bis-phenolic antioxidants may also be advantageously used in combination with the instant disclosure. Examples of ortho-coupled phenols include: 2,2'-bis(4-heptyl-6-t-butyl-phenol); 2,2'-bis(4-octyl-6-t-butyl-phenol); and 2,2'-bis(4-dodecyl-6-t-butyl-phenol). Para-coupled bisphenols include for example 4,4'-bis(2,6-di-t-butyl phenol) and 4,4'-methylene-bis(2,6-di-t-butyl phenol).

Effective amounts of one or more catalytic antioxidants may also be used. The catalytic antioxidants comprise an effective amount of a) one or more oil soluble polymetal organic compounds; and, effective amounts of b) one or more substituted N,N'-diaryl-o-phenylenediamine compounds or c) one or more hindered phenol compounds; or a combination of both b) and c). Catalytic antioxidants are more fully described in U.S. Pat. No. 8,048,833, herein incorporated by reference in its entirety.

Non-phenolic oxidation inhibitors which may be used include aromatic amine antioxidants and these may be used either as such or in combination with phenolics. Typical examples of non-phenolic antioxidants include: alkylated and non-alkylated aromatic amines such as aromatic monoamines of the formula $R^8R^9R^{10}N$ where $R^8$ is an aliphatic, aromatic or substituted aromatic group, $R^9$ is an aromatic or a substituted aromatic group, and $R^{10}$ is H, alkyl, aryl or $R^{11}S(O)_xR^{12}$ where $R^{11}$ is an alkylene, alkenylene, or aralkylene group, $R^{12}$ is a higher alkyl group, or an alkenyl, aryl, or alkaryl group, and x is 0, 1 or 2. The aliphatic group $R^8$ may contain from 1 to about 20 carbon atoms, and in certain embodiments, contains from about 6 to 12 carbon atoms. The aliphatic group is a saturated aliphatic group. In one embodiment, both $R^8$ and $R^9$ are aromatic or substituted aromatic groups, and the aromatic group may be a fused ring aromatic group such as naphthyl. Aromatic groups $R^8$ and $R^9$ may be joined together with other groups such as S.

Typical aromatic amines antioxidants have alkyl substituent groups of at least about 6 carbon atoms. Examples of aliphatic groups include hexyl, heptyl, octyl, nonyl, and decyl. Generally, the aliphatic groups will not contain more than about 14 carbon atoms. The general types of amine antioxidants useful in the present compositions include diphenylamines, phenyl naphthylamines, phenothiazines, imidodibenzyls and diphenyl phenylene diamines. Mixtures of two or more aromatic amines are also useful. Polymeric amine antioxidants can also be used. Particular examples of aromatic amine antioxidants useful in the present disclosure include: p,p'-dioctyldiphenylamine; t-octylphenyl-alphanaphthylamine; phenyl-alphanaphthylamine; and p-octylphenyl-alpha-naphthylamine.

Sulfurized alkyl phenols and alkali or alkaline earth metal salts thereof also are useful antioxidants.

Typical antioxidants include hindered phenols, arylamines. These antioxidants may be used individually by type or in combination with one another. Such additives may be used in an amount of about 0.01 to 5 weight percent, specifically about 0.01 to 1.5 weight percent, more specifically zero to less than 1.5 weight percent, more specifically zero to less than 1 weight percent.

Pour Point Depressants (PPDs)

Conventional pour point depressants (also known as lube oil flow improvers) may be added to the compositions of the present disclosure if desired. These pour point depressant may be added to lubricating compositions of the present disclosure to lower the minimum temperature at which the fluid will flow or can be poured. Examples of suitable pour point depressants include polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. U.S. Pat. Nos. 1,815,022; 2,015,748; 2,191,498; 2,387,501; 2,655, 479; 2,666,746; 2,721,877; 2,721,878; and 3,250,715 describe useful pour point depressants and/or the preparation thereof. Such additives may be used in an amount of about 0.01 to 5 weight percent, specifically about 0.01 to 1.5 weight percent.

Seal Compatibility Agents

In certain embodiments of the invention, the lubricating oil composition further comprises one or more seal compatibility agents. Seal compatibility agents help to swell elastomeric seals by causing a chemical reaction in the fluid or physical change in the elastomer. Suitable seal compatibility agents for lubricating oils include organic phosphates, aromatic esters, aromatic hydrocarbons, esters (butylbenzyl phthalate, for example), and polybutenyl succinic anhydride. Such additives may be used in an amount of about 0.01 to 3 weight percent, specifically about 0.01 to 2 weight percent.

Antifoam Agents

Anti-foam agents may advantageously be added to lubricant compositions. These agents retard the formation of stable foams. Silicones and organic polymers are typical anti-foam agents. For example, polysiloxanes, such as silicon oil or polydimethyl siloxane, provide antifoam properties. Anti-foam agents are commercially available and may be used in conventional minor amounts along with other additives such as demulsifiers; usually the amount of these additives combined is less than 1 weight percent and often less than 0.1 weight percent.

Inhibitors and Antirust Additives

In certain embodiments of the invention, the lubricating oil composition further comprises one or more inhibitor/antirust additives. Antirust additives (or corrosion inhibitors) are additives that protect lubricated metal surfaces against chemical attack by water or other contaminants. A wide variety of these are commercially available.

One type of antirust additive is a polar compound that wets the metal surface, and in certain embodiments, protects it with a film of oil. Another type of antirust additive absorbs water by incorporating it in a water-in-oil emulsion so that only the oil touches the metal surface. Yet another type of antirust additive chemically adheres to the metal to produce a non-reactive surface. Examples of suitable additives include zinc dithiophosphates, metal phenolates, basic metal sulfonates, fatty acids and amines. Such additives may be used in an amount of about 0.01 to 5 weight percent, specifically about 0.01 to 1.5 weight percent.

Friction Modifiers

In certain embodiments of the invention, the lubricating oil composition further comprises one or more additional friction modifiers. (e.g., a mixture a compound of formula (I) and one or more other friction modifier(s)). As discussed herein, a friction modifier (also known as a friction reducer, or lubricity agent or oiliness agent) is any material or materials that can alter the coefficient of friction of a surface lubricated by any lubricant or fluid containing such material(s) (e.g., base oils, formulated lubricant compositions or functional fluids). As described herein, compounds of formula (I) may thermally degrade step-wise (i.e., a degradation product may function as a friction modifier). Accordingly, in certain embodiments, a friction modifier may be a thermally activated friction modifier.

Illustrative friction modifiers may include, for example, organometallic compounds or materials, or mixtures thereof. Illustrative organometallic friction modifiers useful in the lubricating oil formulations of this disclosure include, for example, molybdenum amine, molybdenum diamine, an organotungstenate, a molybdenum dithiocarbamate, molybdenum dithiophosphates, molybdenum amine complexes, molybdenum carboxylates, and the like, and mixtures thereof. Similar tungsten based compounds may be used.

Other illustrative friction modifiers useful in the lubricating oil formulations of this disclosure include, for example, alkoxylated fatty acid esters, alkanolamides, polyol fatty acid esters, borated glycerol fatty acid esters, fatty alcohol ethers, and mixtures thereof.

Illustrative alkoxylated fatty acid esters include, for example, polyoxyethylene stearate, fatty acid polyglycol ester, and the like. These can include polyoxypropylene stearate, polyoxybutylene stearate, polyoxyethylene isostearate, polyoxypropylene isostearate, polyoxyethylene palmitate, and the like.

Illustrative alkanolamides include, for example, lauric acid diethylalkanolamide, palmic acid diethylalkanolamide, and the like. These can include oleic acid diethylalkanolamide, stearic acid diethylalkanolamide, oleic acid diethylalkanolamide, polyethoxylated hydrocarbylamides, polypropoxylated hydrocarbylamides, and the like.

Illustrative polyol fatty acid esters include, for example, glycerol mono-oleate, saturated mono-, di-, and tri-glyceride esters, glycerol mono-stearate, and the like. These can include polyol esters, hydroxyl-containing polyol esters, and the like.

Illustrative borated glycerol fatty acid esters include, for example, borated glycerol mono-oleate, borated saturated mono-, di-, and tri-glyceride esters, borated glycerol monosterate, and the like. In addition to glycerol polyols, these can include trimethylolpropane, pentaerythritol, sorbitan, and the like. These esters can be polyol monocarboxylate esters, polyol dicarboxylate esters, and on occasion polyoltricarboxylate esters. Specific embodiments can be the glycerol mono-oleates, glycerol dioleates, glycerol trioleates, glycerol monostearates, glycerol distearates, and glycerol tristearates and the corresponding glycerol monopalmitates, glycerol dipalmitates, and glycerol tripalmitates, and the respective isostearates, linoleates, and the like. On occasion the glycerol esters can be particularly useful, as well as mixtures containing any of these. Ethoxylated, propoxylated, butoxylated fatty acid esters of polyols, especially using glycerol as underlying polyol, can be particularly useful.

Illustrative fatty alcohol ethers include, for example, stearyl ether, myristyl ether, and the like. Alcohols, including those that have carbon numbers from $C_3$ to $C_{50}$, can be ethoxylated, propoxylated, or butoxylated to form the corresponding fatty alkyl ethers. The underlying alcohol portion can specifically be stearyl, myristyl, $C_{11}$-$C_{13}$ hydrocarbon, oleyl, isosteryl, and the like.

The lubricating oils of this disclosure exhibit desired properties, e.g., wear control, in the presence or absence of additional friction modifiers.

Useful concentrations of friction modifiers may typically range from 0.01 weight percent to 5 weight percent, or about 0.1 weight percent to about 2.5 weight percent, or about 0.1 weight percent to about 1.5 weight percent, or about 0.1 weight percent to about 1 weight percent. Concentrations of molybdenum-containing materials are often described in terms of Mo metal concentration. Advantageous concentrations of Mo may range from 25 ppm to 700 ppm or more, and often with a range of 50-200 ppm. Friction modifiers of all types may be used alone or in mixtures with the materials of this disclosure. Often mixtures of two or more friction modifiers, or mixtures of friction modifier(s) with alternate surface active material(s), are also desirable.

When lubricating oil compositions contain one or more of the additives discussed above, the additive(s) are blended into the composition in an amount sufficient for it to perform its intended function. Typical amounts of such additives useful in the present disclosure are shown in Table A below.

It is noted that many of the additives are shipped from the additive manufacturer as a concentrate, containing one or more additives together, with a certain amount of base oil diluents. Accordingly, the weight amounts in Table A below, as well as other amounts mentioned herein, are directed to the amount of active ingredient (that is the non-diluent portion of the ingredient). The weight percent (wt %) indicated below is based on the total weight of the lubricating oil composition.

TABLE A

Typical Amounts of Other Lubricating Oil Components

| Compound | Approximate wt % (Useful) | Approximate wt % (Specific) |
|---|---|---|
| Dispersant | 0.1-20 | 0.1-8 |
| Detergent | 0.1-20 | 0.1-8 |
| Friction Modifier | 0.01-5 | 0.01-1.5 |
| Antioxidant | 0.1-5 | 0.1-1.5 |
| Pour Point Depressant (PPD) | 0.0-5 | 0.01-1.5 |
| Anti-foam Agent | 0.001-3 | 0.001-0.15 |
| Viscosity Modifier (solid polymer basis) | 0.1-2 | 0.1-1 |
| Anti-wear | 0.2-3 | 0.5-1 |
| Inhibitor and Antirust | 0.01-5 | 0.01-1.5 |

The foregoing additives are all commercially available materials. These additives may be added independently but are usually precombined in packages which can be obtained from suppliers of lubricant oil additives. Additive packages with a variety of ingredients, proportions and characteristics are available and selection of the appropriate package will take the requisite use of the ultimate composition into account.

Certain Embodiments of Compounds of Formula (I)

Certain embodiments of the invention provide a compound of formula (I):

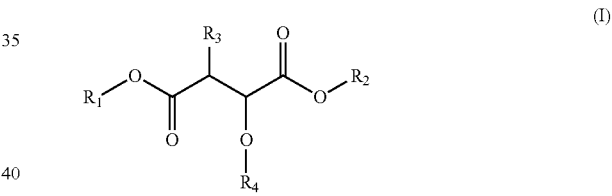

wherein, $R_1$ and $R_2$ are each independently H, $(C_1$-$C_{12})$alkyl, benzyl or phenethyl; $R_3$ is H or $OR^a$, wherein $R^a$ is $(C_1$-$C_{20})$alkyl, $(C_1$-$C_{20})$alkanoyl, $(C_2$-$C_{20})$alkenyl or $(C_3$-$C_{20})$alkenoyl; and $R_4$ is $(C_1$-$C_{20})$alkyl, $(C_1$-$C_{20})$alkanoyl, $(C_2$-$C_{20})$alkenyl or $(C_3$-$C_{20})$alkenoyl; or a salt thereof, wherein the compound of formula (I) is not:

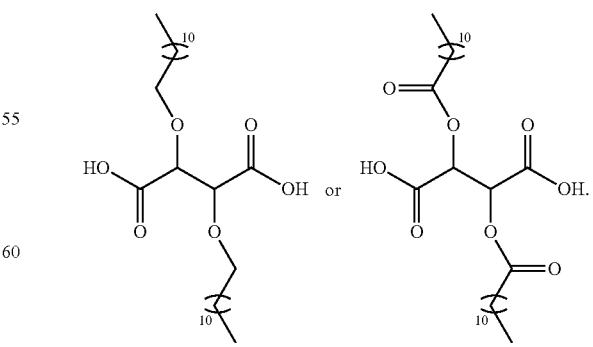

Certain embodiments of the invention also provide a compound of formula (I):

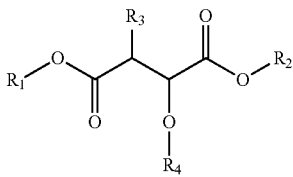

(I)

wherein, $R_1$ and $R_2$ are each independently H, $(C_1-C_{12})$alkyl, benzyl or phenethyl; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_1-C_{20})$alkyl, $(C_1-C_{20})$alkanoyl, $(C_2-C_{20})$alkenyl or $(C_3-C_{20})$alkenoyl; or a salt thereof, wherein $R^a$ and $R_4$ are not $(C_{12})$alkyl or $(C_{12})$alkanoyl.

Certain embodiments of the invention provide a compound of formula (Ia):

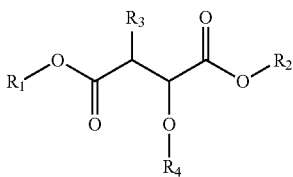

(Ia)

wherein, $R_1$ and $R_2$ are each independently H, $(C_1-C_{12})$alkyl, benzyl or phenethyl; $R_3$ is H; and $R_4$ is $(C_1-C_{20})$alkyl, $(C_1-C_{20})$alkanoyl, $(C_2-C_{20})$alkenyl or $(C_3-C_{20})$alkenoyl; or a salt thereof.

Certain embodiments of the invention provide a compound of formula (Ib):

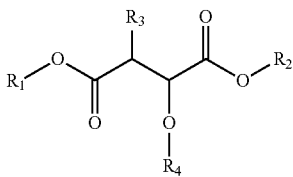

(Ib)

wherein, $R_1$ and $R_2$ are each independently H, $(C_1-C_{12})$alkyl, benzyl or phenethyl; $R_3$ is H or $OR^a$, wherein $R^a$ is $(C_1-C_8)$alkyl, $(C_1-C_8)$alkanoyl, $(C_2-C_8)$alkenyl or $(C_3-C_8)$alkenoyl; and $R_4$ is $(C_1-C_{20})$alkyl, $(C_1-C_{20})$alkanoyl, $(C_2-C_{20})$alkenyl or $(C_3-C_{20})$alkenoyl; or a salt thereof.

Certain embodiments of the invention provide a compound of formula (Ic):

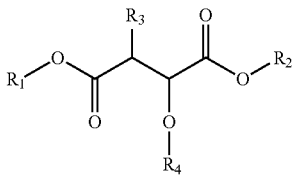

(Ic)

wherein, $R_1$ and $R_2$ are each independently H, $(C_1-C_{12})$alkyl, benzyl or phenethyl; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_{14}-C_{20})$alkyl, $(C_{14}-C_{20})$alkanoyl, $(C_{14}-C_{20})$alkenyl or $(C_{14}-C_{20})$alkenoyl; or a salt thereof.

Certain embodiments of the invention also provide a compound of formula (Id):

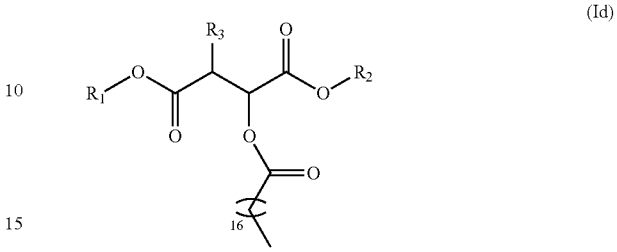

(Id)

wherein, $R_1$ and $R_2$ are each independently H, $(C_1-C_{12})$alkyl, benzyl or phenethyl; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; or a salt thereof.

Certain embodiments of the invention also provide a compound of formula (Ie):

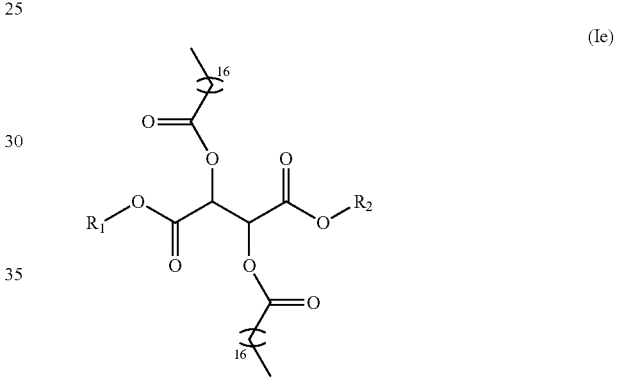

(Ie)

wherein, $R_1$ and $R_2$ are each independently H, $(C_1-C_{12})$alkyl, benzyl or phenethyl; or a salt thereof.

In certain embodiments of the compounds of formula (I), (Ia), (Ib), (Ic), (Id) and (Ie), $R_3$ and $R_4$ may be a value as described herein. For example, in certain embodiments, $R_3$ is H. In certain embodiments, $R_3$ is $OR^a$, wherein $R^a$ is $(C_{14})$alkanoyl. In certain embodiments, $R_3$ is $OR^a$, wherein $R^a$ is $(C_{16})$alkanoyl. In certain embodiments, $R_3$ is $OR^a$, wherein $R^a$ is $(C_1)$alkyl. In certain embodiments, $R_3$ is $OR^a$, wherein $R^a$ is $(C_{18})$alkenyl. In certain embodiments, $R_4$ is $(C_{14})$alkanoyl. In certain embodiments, $R_4$ is $(C_{16})$alkanoyl. In certain embodiments, $R_4$ is $(C_{18})$alkanoyl.

Similarly, in certain embodiments of the compounds of formula (I), (Ia), (Ib), (Ic), (Id) and (Ie), $R_1$ and $R_2$ may be a value as described herein.

For example, in certain embodiments, $R^1$ is H.

In certain embodiments, $R^1$ is $(C_1-C_{12})$alkyl. In certain embodiments, $R^1$ is $(C_1-C_6)$alkyl.

In certain embodiments, $R^1$ is methyl, ethyl, propyl, isopropyl, butyl, isobutyl, sec-butyl or tert-butyl. In certain embodiments, $R^1$ is ethyl. In certain embodiments, $R^1$ is tert-butyl.

In certain embodiments, $R^1$ is benzyl.

In certain embodiments, $R^2$ is H.

In certain embodiments, $R^2$ is $(C_1-C_{12})$alkyl. In certain embodiments, $R^2$ is $(C_1-C_6)$alkyl. In certain embodiments, $R^2$ is methyl, ethyl, propyl, isopropyl, butyl, isobutyl, sec-butyl or tert-butyl. In certain embodiments, $R^2$ is ethyl. In certain embodiments, $R^2$ is tert-butyl.

In certain embodiments, $R^2$ is benzyl.

In certain embodiments, $R^1$ and $R^2$ are each H.

In certain embodiments, $R^1$ and $R^2$ are each independently $(C_1-C_{12})$alkyl. In certain embodiments, $R^1$ and $R^2$ are each independently $(C_1-C_6)$alkyl. In certain embodiments, $R^1$ and $R^2$ are each ethyl. In certain embodiments, $R^1$ and $R^2$ are each tert-butyl.

In certain embodiments, $R^1$ and $R^2$ are each benzyl.

In certain embodiments, a compound of the invention is selected from the group consisting of:

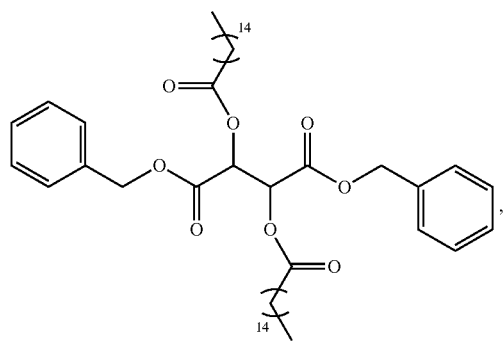

,

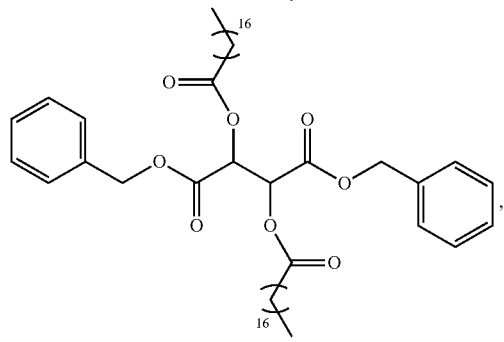

,

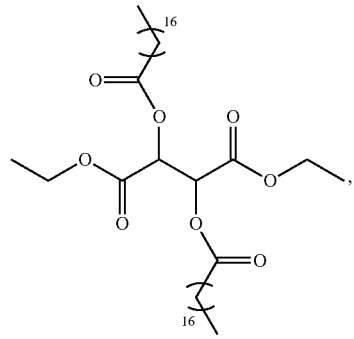

,

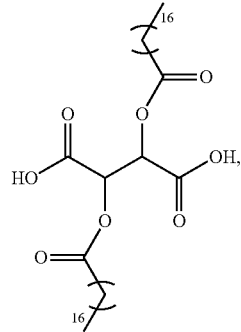

-continued

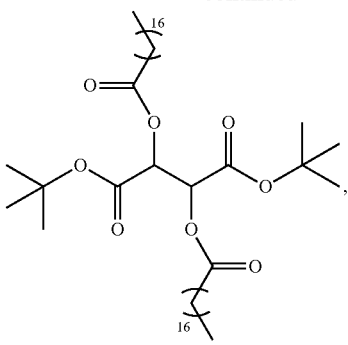

,

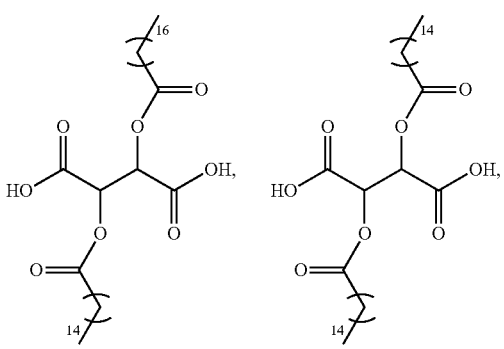

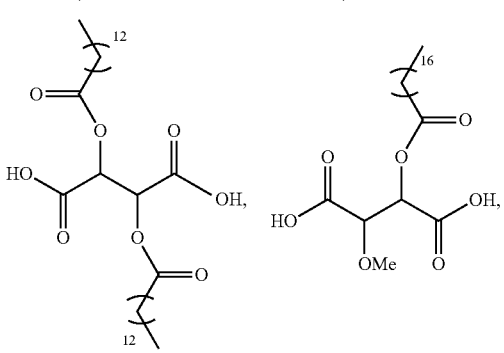

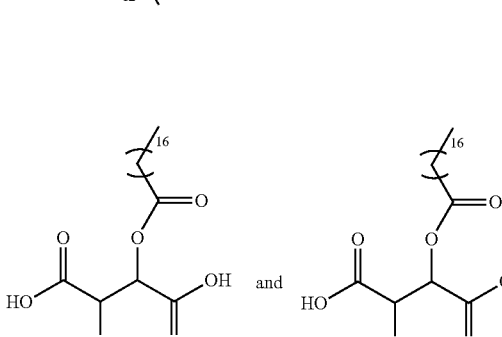

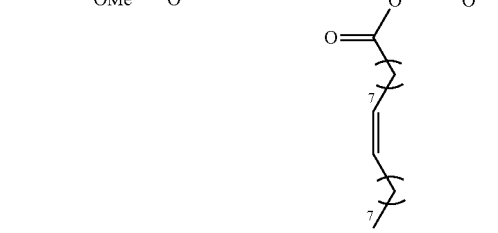

and salts thereof.

In certain embodiments, a compound of the invention is selected from the group consisting of:

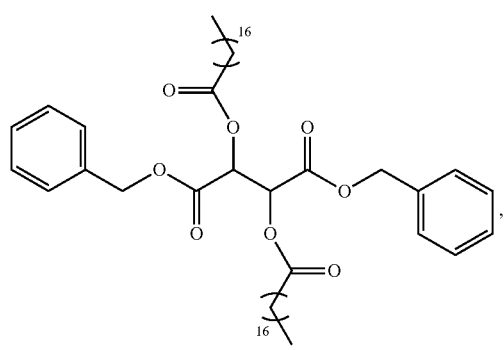
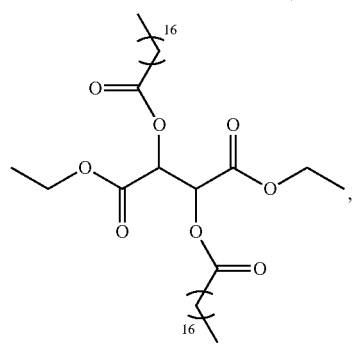
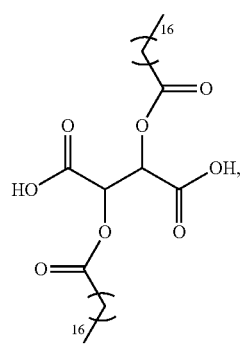
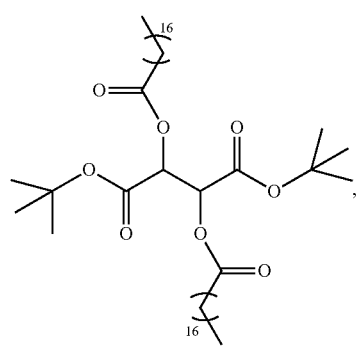
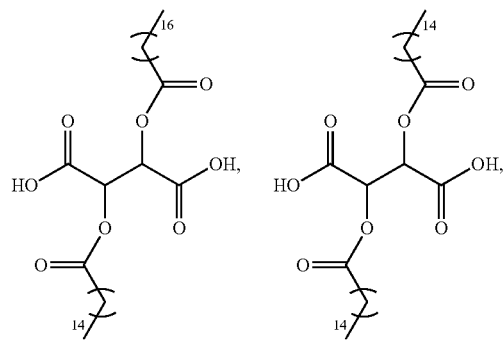
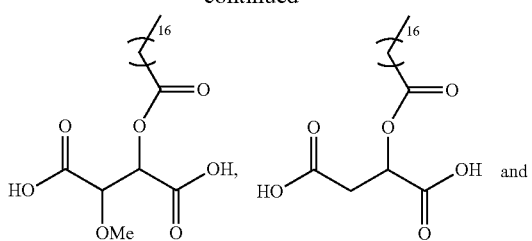
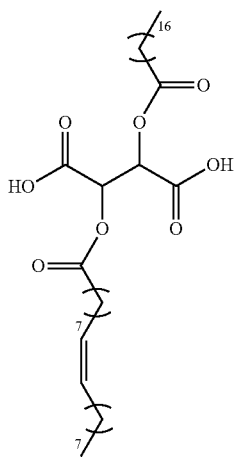
and salts thereof.
In certain embodiments, a compound of the invention is selected from the group consisting of:
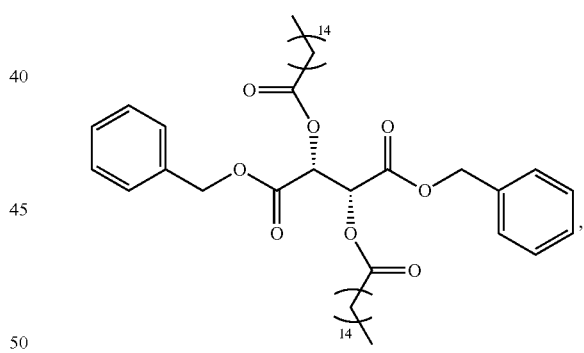
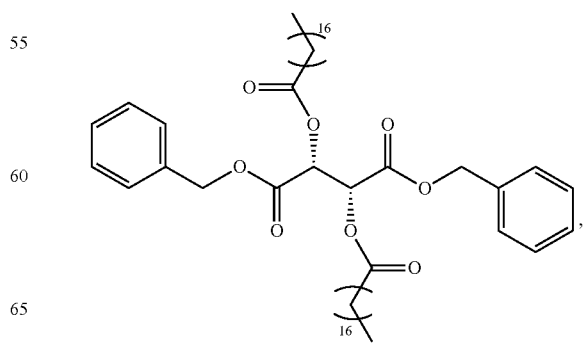

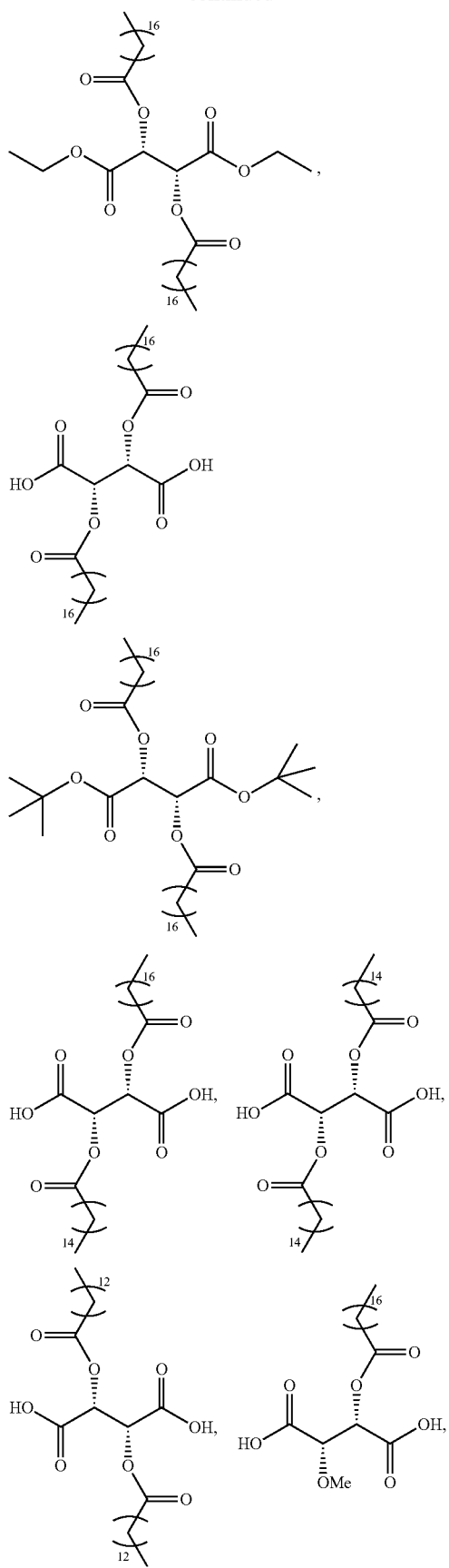
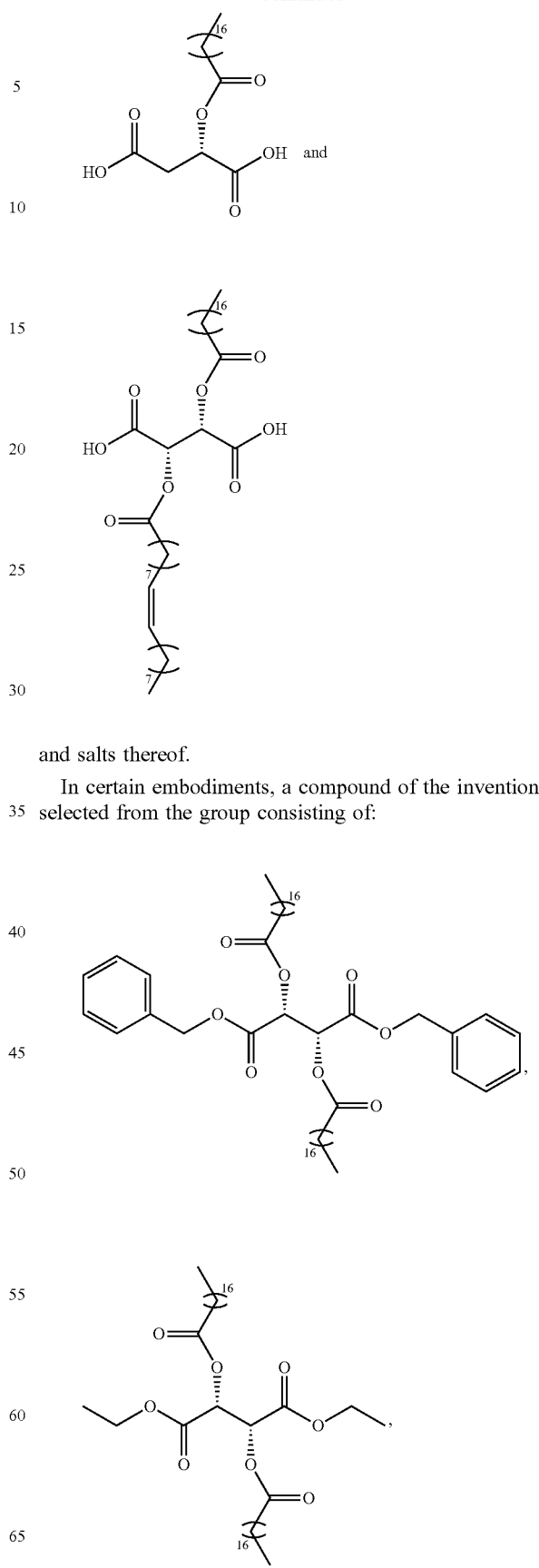
and salts thereof.
In certain embodiments, a compound of the invention is selected from the group consisting of:
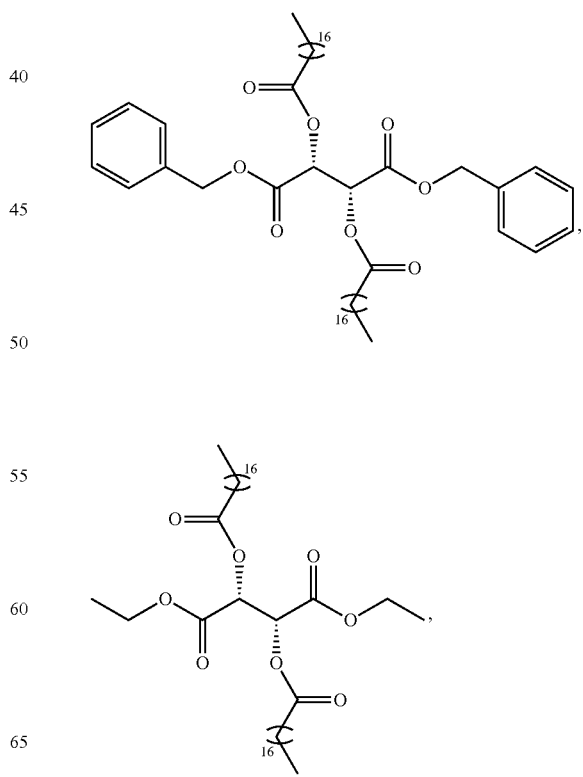

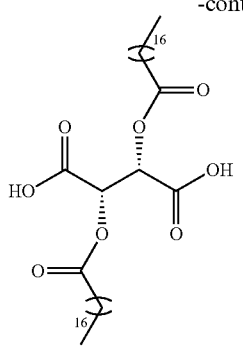
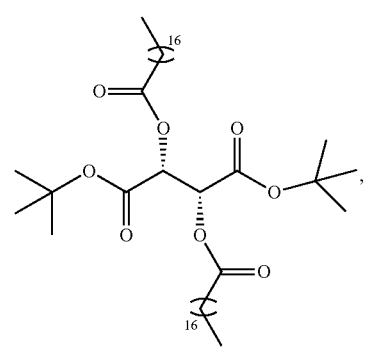
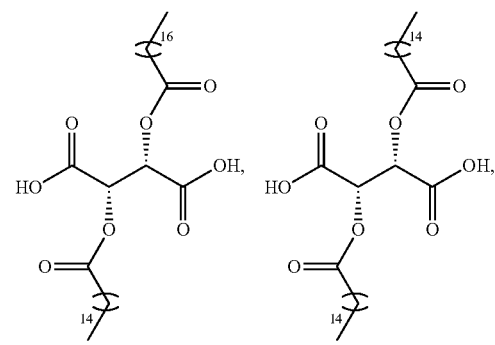
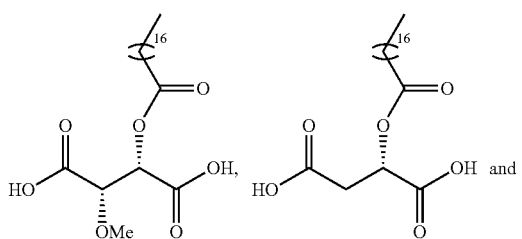
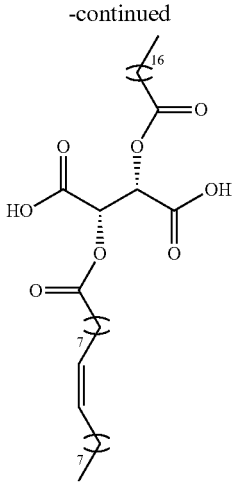
and salts thereof
In certain embodiments, a compound of the invention is:
[structure]
or a salt thereof.
In certain embodiments, a compound of the invention is:
[structure]
Synthetic Methods
Certain embodiments of the invention provide a method for preparing a final compound of formula (I):

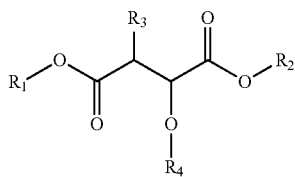

(I)

wherein, $R_1$ and $R_2$ are each independently $(C_1$-$C_{12})$alkyl, benzyl or phenethyl; $R_3$ is H or $OR^a$, wherein $R^a$ is $(C_1$-$C_{20})$alkyl, $(C_1$-$C_{20})$alkanoyl, $(C_2$-$C_{20})$alkenyl or $(C_3$-$C_{20})$alkenoyl; and $R_4$ is $(C_1$-$C_{20})$alkyl, $(C_1$-$C_{20})$alkanoyl, $(C_2$-$C_{20})$alkenyl or $(C_3$-$C_{20})$alkenoyl; comprising converting a corresponding compound, wherein $R_1$ and $R_2$ are each H, to the final compound of formula (I).

In certain embodiments, $R_1$ and $R_2$ are each independently $(C_1$-$C_{12})$alkyl. In certain embodiments, $R_1$ and $R_2$ are each independently $(C_1$-$C_6)$alkyl. In certain embodiments, $R_1$ and $R_2$ are each ethyl. In certain embodiments, $R_1$ and $R_2$ are each tert-butyl.

In certain embodiments, $R_1$ and $R_2$ are each benzyl.

In certain embodiments, $R_3$ and $R_4$ are each independently any value as described herein.

In certain embodiments, the final compound of formula (I) is selected from the group consisting of:

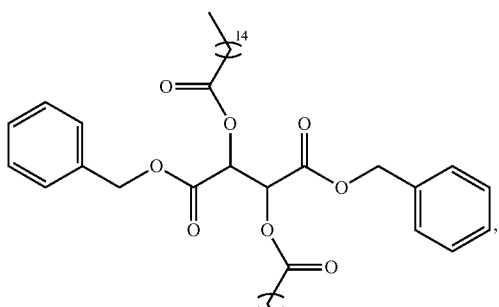

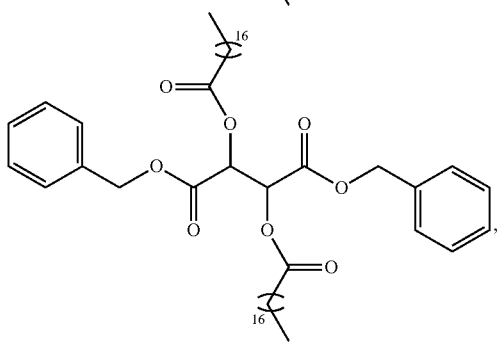

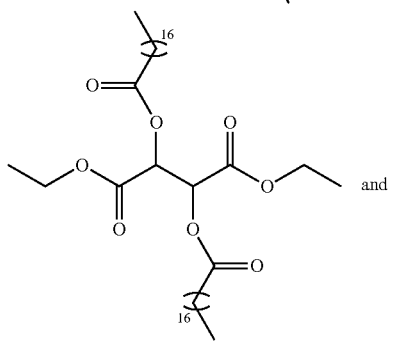

and

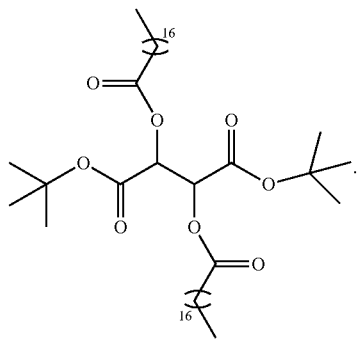

In certain embodiments, the final compound of formula (I) is selected from the group consisting of:

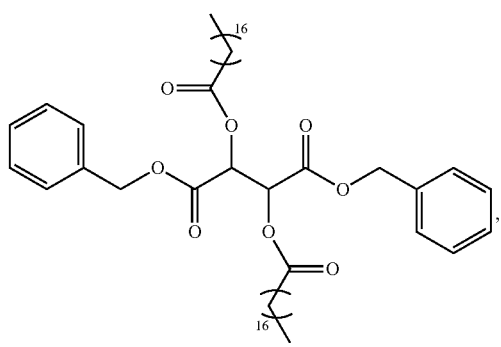

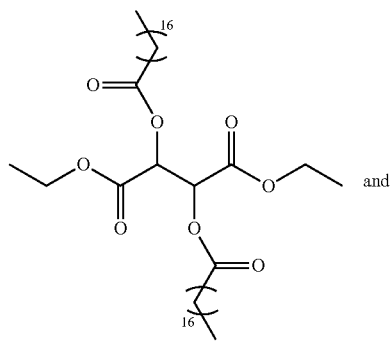

and

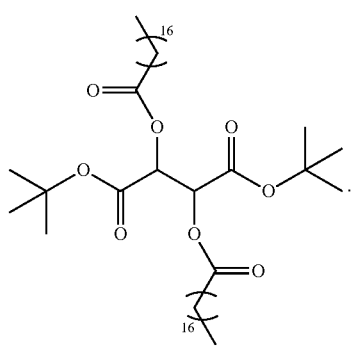

In certain embodiments, the final compound of formula (I) is:

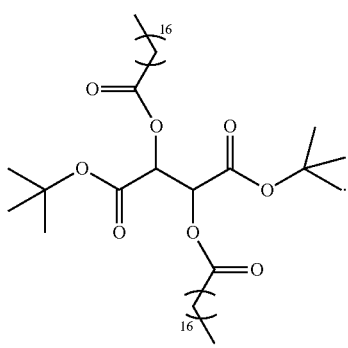
In certain embodiments, the method further comprises saponifying the final compound of formula (I) to provide a corresponding diacid, or a salt thereof.
In certain embodiments, the corresponding diacid is selected from the group consisting of:
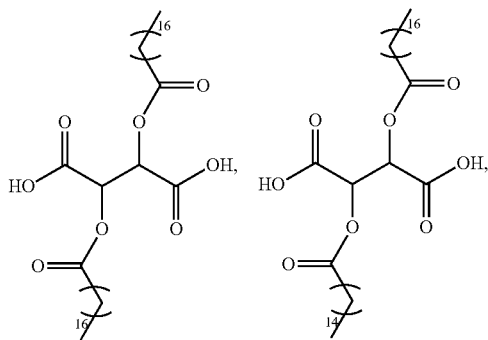
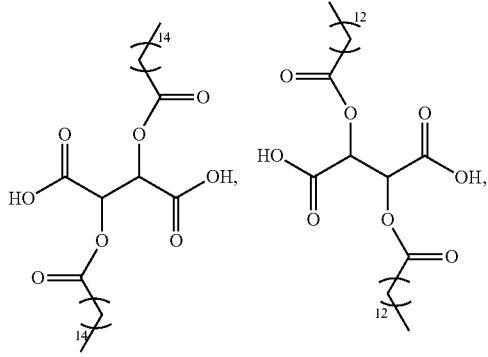
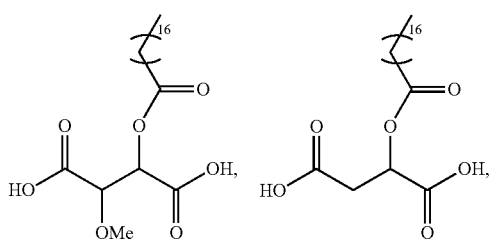
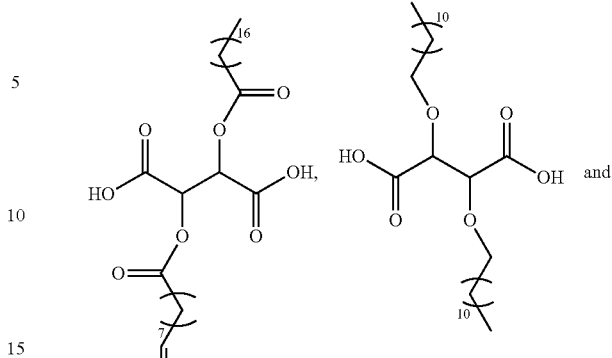
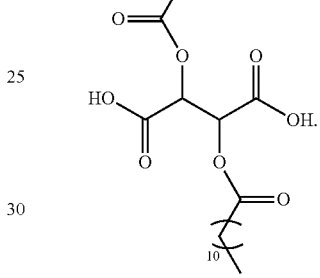
In certain embodiments, the corresponding diacid is selected from the group consisting of:
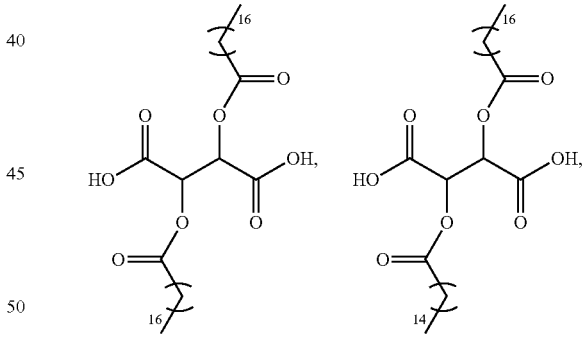
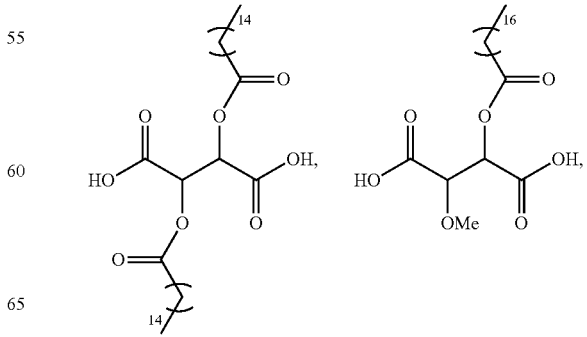

-continued

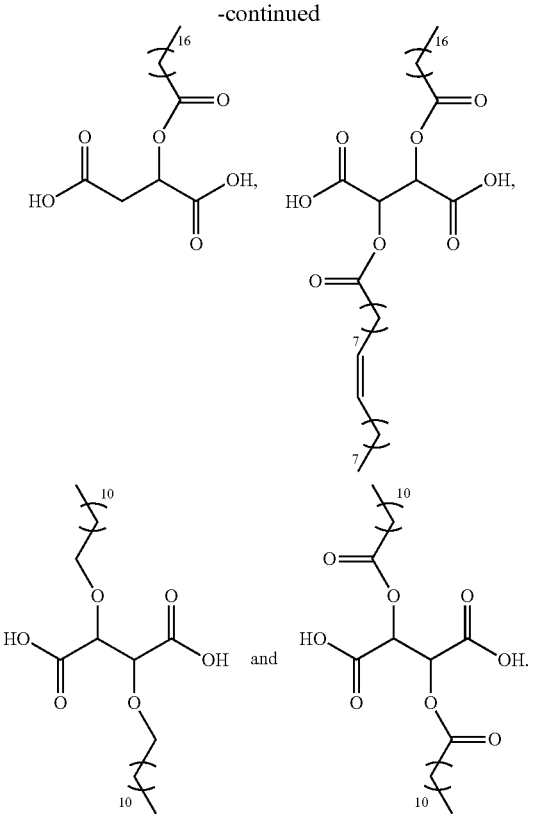

In certain embodiments, the corresponding diacid is:

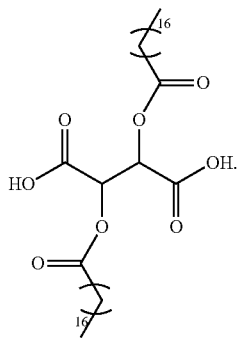

Certain embodiments of the invention also provide a method for preparing a final compound of formula (I):

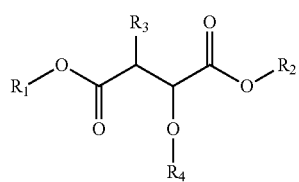

wherein $R_1$ and $R_2$ are each H; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_1-C_{20})$alkyl, $(C_1-C_{20})$alkanoyl, $(C_2-C_{20})$alkenyl or $(C_3-C_{20})$alkenoyl; or a salt thereof comprising acylating or alkylating tartaric acid to provide the final compound of formula (I), or a salt thereof.

Certain embodiments of the invention also provide a method for preparing a final compound of formula (I),

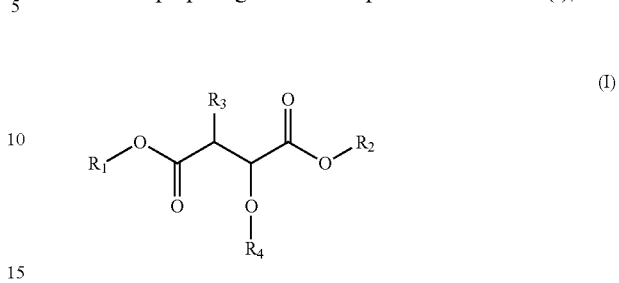

wherein $R_1$ and $R_2$ are each H; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_1-C_{20})$alkyl, $(C_1-C_{20})$alkanoyl, $(C_2-C_{20})$alkenyl or $(C_3-C_{20})$alkenoyl; or a salt thereof, comprising saponifying a corresponding compound of formula (I), wherein $R_1$ and $R_2$ are each other than H, to provide the final compound of formula (I), or a salt thereof.

In certain embodiments, the final compound of formula (I) is selected from the group consisting of:

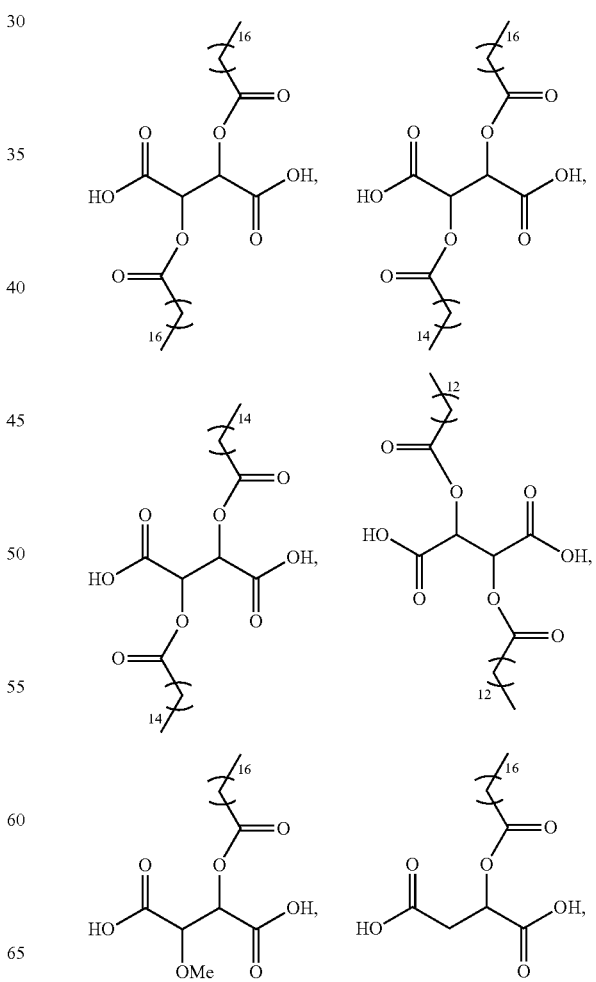

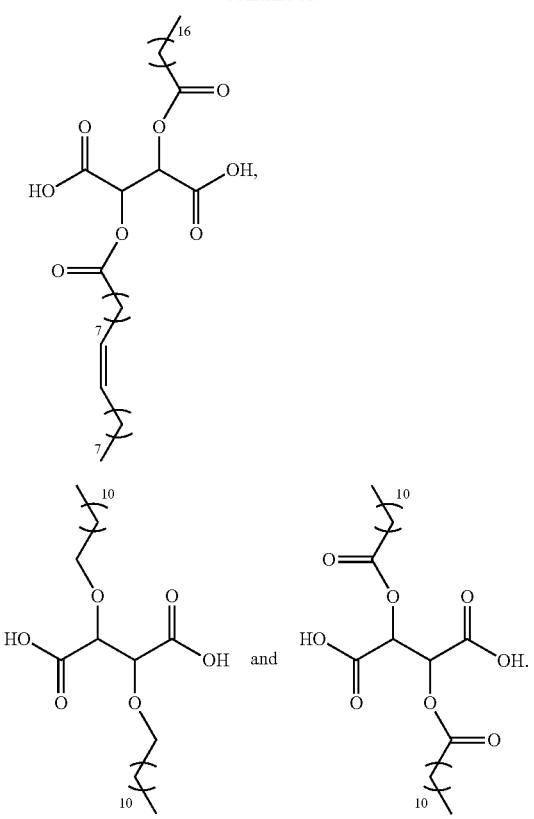

In certain embodiments, the final compound of formula (I) is selected from the group consisting of:

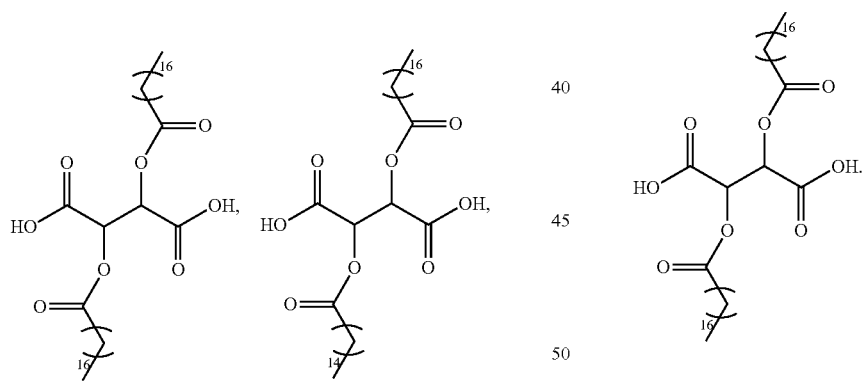

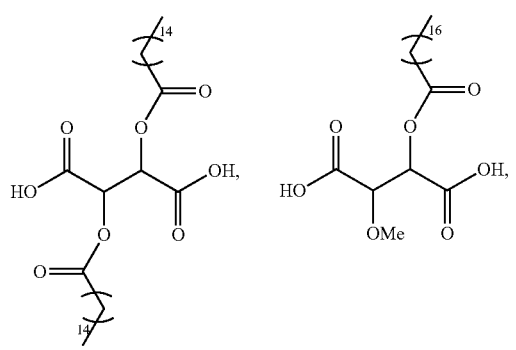

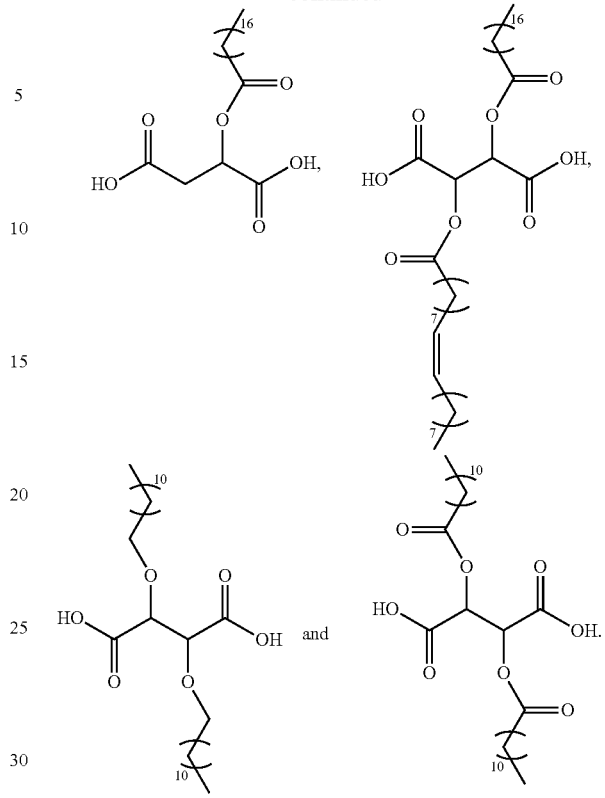

In certain embodiments, the final compound of formula (I) is:

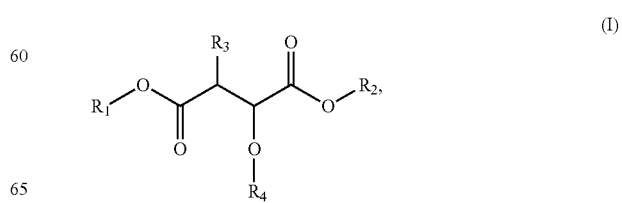

Methods of Use

Certain embodiments of the invention provide a method for improving the frictional properties of a lubricating oil composition, comprising adding to the lubricating oil composition a compound of formula (I):

$$\text{(I)}$$

wherein, $R_1$ and $R_2$ are each independently H, $(C_1-C_{12})$ alkyl, benzyl or phenethyl; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_1-C_{20})$alkyl, $(C_1-C_{20})$alkanoyl, $(C_2-C_{20})$alkenyl or $(C_3-C_{20})$alkenoyl; or a salt thereof.

In certain embodiments, the lubricating oil composition further comprises a lubricating oil base stock. In certain embodiments, the lubricating oil composition comprises a lubricating oil base stock as a major component and a compound of formula (I) as a minor component.

Certain embodiments of the invention also provide a method for improving friction control in an engine or other mechanical component lubricated with a lubricating oil, by using as the lubricating oil a formulated oil. The formulated oil has a composition comprising a lubricating oil base stock as a major component, and one or more lubricating oil additives as a minor component, wherein at least one lubricating oil additive is a compound of formula (I):

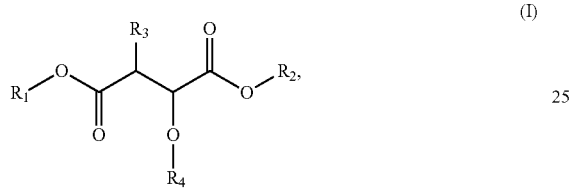

wherein, $R_1$ and $R_2$ are each independently H, $(C_1-C_{12})$ alkyl, benzyl or phenethyl; $R_3$ is H or $OR^a$, wherein $R^a$ is $(C_1-C_{20})$alkyl, $(C_1-C_{20})$alkanoyl, $(C_2-C_{20})$alkenyl or $(C_3-C_{20})$alkenoyl; and $R_4$ is $(C_1-C_{20})$alkyl, $(C_1-C_{20})$alkanoyl, $(C_2-C_{20})$alkenyl or $(C_3-C_{20})$alkenoyl; or a salt thereof.

In yet another embodiment, friction control in an engine is improved as compared to friction control in an engine using a lubricating oil composition containing a minor component other than the lubricating oil additive comprising a compound of formula (I), or a salt thereof.

By "major component" is meant that at least about 70 weight percent or more of the total weight of the lubricating oil composition or formulated oil will comprise the lubricating oil base stock. By "minor component" is meant that less than about 30 weight percent of the total weight of the lubricating oil composition or formulated oil will comprise one or more lubricating oil additives.

In certain embodiments, $R_1$, $R_2$, $R_3$ and $R_4$ are any value as described herein.

In certain embodiments, the compound of formula (I) is selected from the group consisting of:

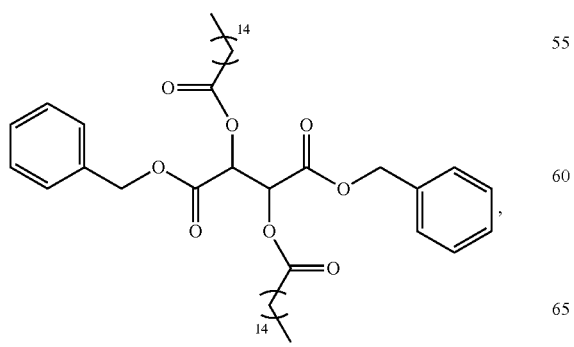

-continued

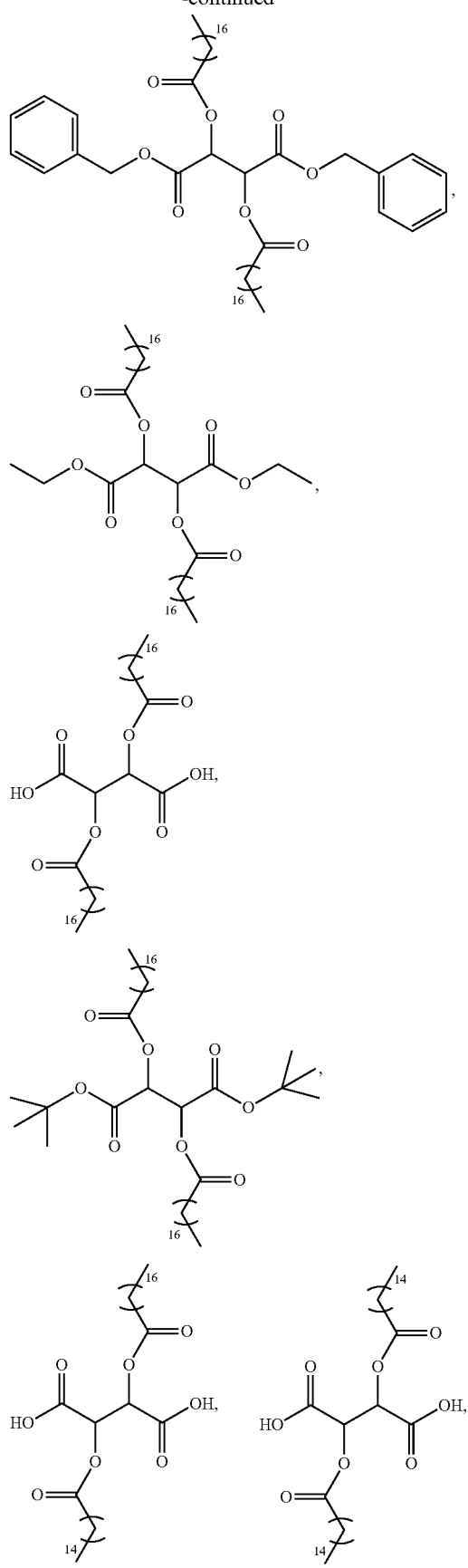

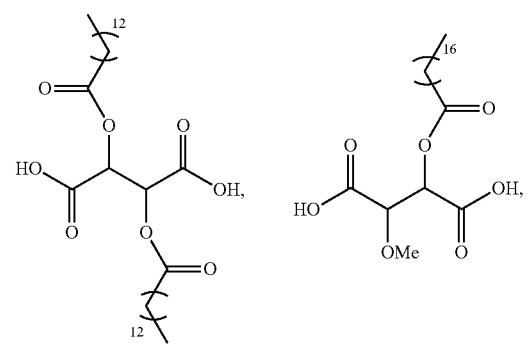
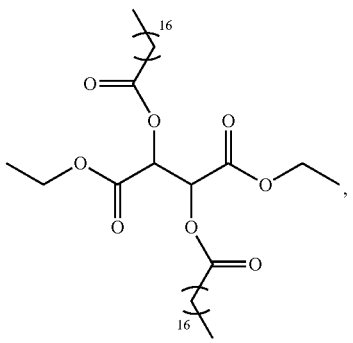
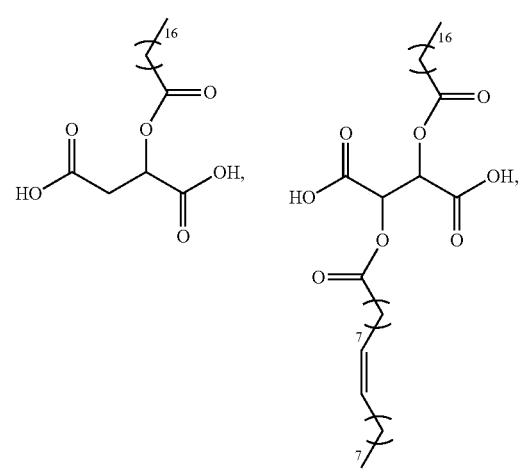
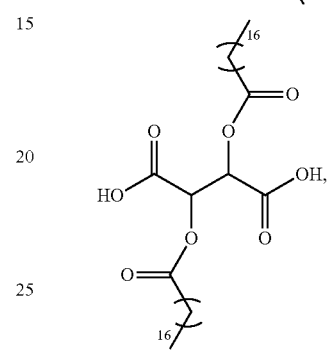
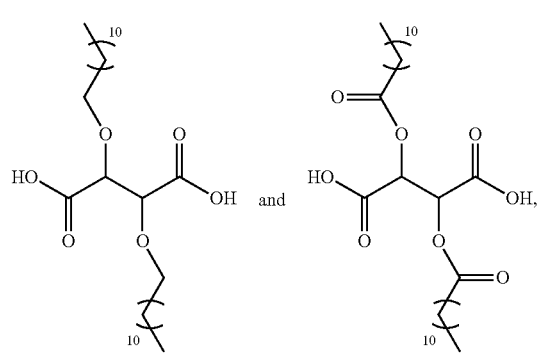
and salts thereof.
In certain embodiments, the compound of formula (I) is selected from the group consisting of:
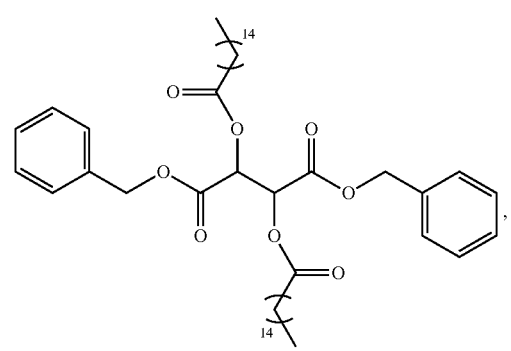
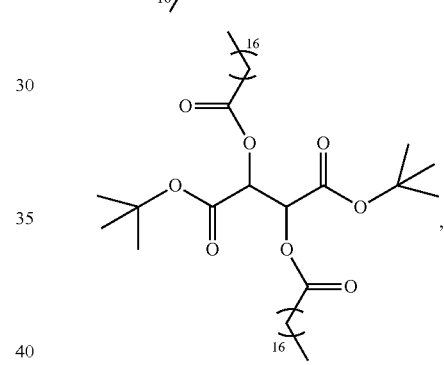
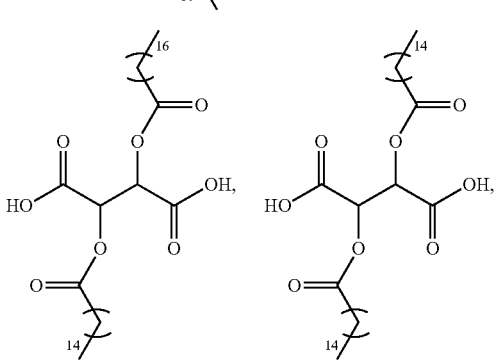
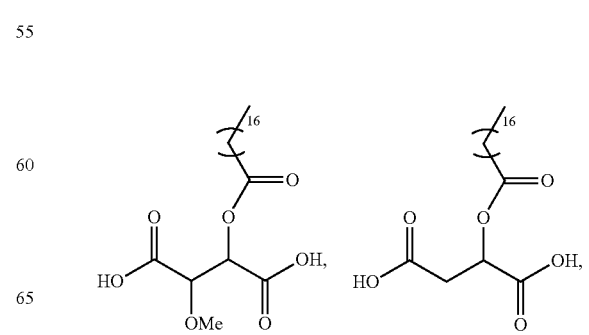

-continued

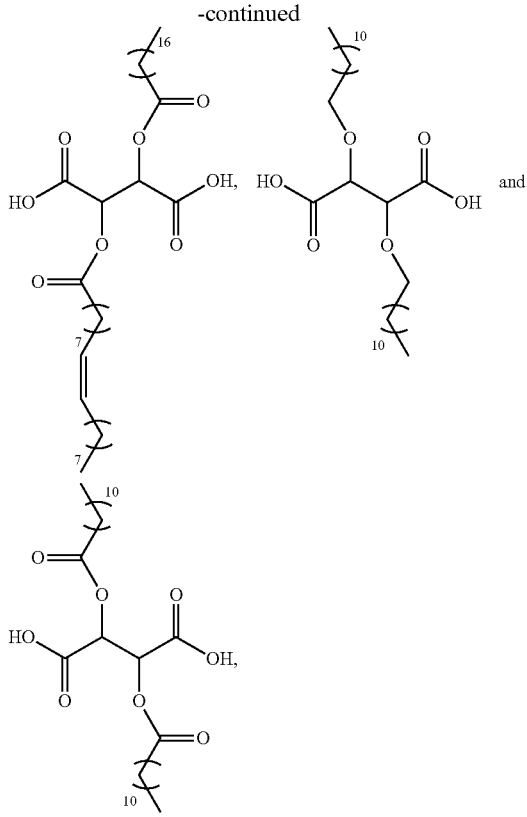

and salts thereof.

In certain embodiments, the compound of formula (I) is:

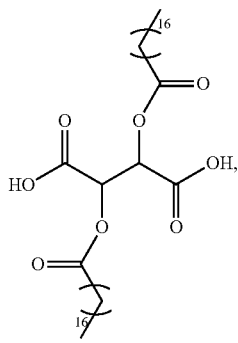

or a salt thereof.

In certain embodiments, the compound of formula (I) is:

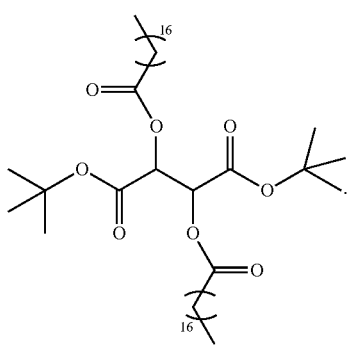

In certain embodiments, the lubricating oil base stock comprises a Group I, Group II, Group III, Group IV or Group V base oil.

In certain embodiments of the invention, the lubricating oil composition or formulated oil, comprises a mixture of compounds of formula (I) (e.g., two or more compounds of formula (I)), or a salts thereof. In certain embodiments of the invention, a lubricating oil composition or formulated oil as described herein, comprises a mixture of compounds of formula (I), or a salts thereof, wherein the compounds of formula (I) have different thermal release temperatures.

In certain embodiments, the compound of formula (I), or a salt thereof, is present in an amount of from about 0.01 weight percent to about 5 weight percent, based on the total weight of the lubricating oil composition or formulated oil.

In certain embodiments, the compound of formula (I), or a salt thereof, is present in an amount of from about 0.1 weight percent to about 1.5 weight percent, based on the total weight of the lubricating oil composition or formulated oil.

In certain embodiments, the oil base stock is present in an amount of from about 70 weight percent to about 95 weight percent, based on the total weight of the lubricating oil composition or formulated oil.

In certain embodiments, the lubricating oil composition further comprises one or more lubricating performance additives.

In certain embodiments, the lubricating performance additive is selected from the group consisting of an anti-wear additive, viscosity modifier, antioxidant, detergent, dispersant, pour point depressant, corrosion inhibitor, metal deactivator, seal compatibility additive, anti-foam agent, other friction modifier and anti-rust additive/inhibitor.

Certain embodiments of the invention provide a method of reducing friction in an engine or other mechanical component lubricated with a lubricating oil, comprising providing a lubricating oil composition as described herein to the engine or mechanical component.

Certain embodiments of the invention provide a method of providing friction reducing properties in a lubricant system, comprising adding a lubricating oil composition as described herein to the lubricant system.

In certain embodiments, the average friction coefficient at 100° C. of the lubricating oil composition, as measured using a High Frequency Reciprocating Rig (HFRR) test, is less than or equal to about 0.12, or less than or equal to 0.1, or less than or equal to 0.08. In certain embodiments, the HFRR test is performed using conditions as described in Example 12.

In certain embodiments, the average friction coefficient at 200° C. of the lubricating oil composition, as measured using a High Frequency Reciprocating Rig (HFRR) test, is less than or equal to about 0.12, or less than or equal to 0.1, or less than or equal to 0.08. In certain embodiments, the HFRR test is performed using conditions as described in Example 12.

Certain embodiments of the invention also provide a method for improving the solubility of a compound of formula (I):

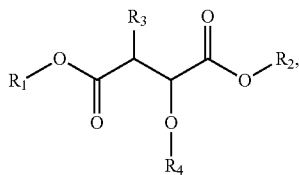

(I)

wherein, $R_1$ and $R_2$ are each H; comprising converting the compound to a corresponding compound of formula (I), wherein at least one of $R_1$ and $R_2$ is $(C_1-C_{12})$alkyl.

Certain Definitions

The following definitions are used, unless otherwise described: halo is fluoro, chloro, bromo, or iodo. Alkyl, alkanoyl, alkenyl, alkenoyl, etc. denote both straight and branched groups; but reference to an individual radical such as propyl embraces only the straight chain radical, a branched chain isomer such as isopropyl being specifically referred to.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase. When a bond in a compound formula herein is drawn in a non-stereochemical manner (e.g. flat), the atom to which the bond is attached includes all stereochemical possibilities.

When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

In one embodiment, the compound is not enriched in a single stereoisomer (e.g., a diastereomer or enantiomer) more than about 60%. In one embodiment, the compound is not enriched in a single stereoisomer (e.g., a diastereomer or enantiomer) more than about 51%.

Specific values listed below for radicals, substituents, and ranges, are for illustration only; they do not exclude other defined values or other values within defined ranges for the radicals and substituents.

Specifically, $(C_1-C_{20})$alkyl can be methyl, ethyl, propyl, isopropyl, butyl, iso-butyl, sec-butyl, tert-butyl, pentyl, 3-pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl. $(C_1-C_{12})$alkyl can be methyl, ethyl, propyl, isopropyl, butyl, iso-butyl, sec-butyl, tert-butyl, pentyl, 3-pentyl, hexyl, heptyl, octyl, nonyl, decyl, undecyl or dodecyl. $(C_1-C_6)$alkyl can be methyl, ethyl, propyl, isopropyl, butyl, iso-butyl, sec-butyl, tert-butyl, pentyl, 3-pentyl, or hexyl.

As described herein, $(C_1-C_{20})$alkanoyl is $((C_1-C_{19})$alkyl$)$-$C(=O)$—. For example, $(C_1-C_6)$alkanoyl can be acetyl, propanoyl or butanoyl.

As described herein, $(C_2-C_{20})$alkenyl is a $C_2$ to $C_{20}$ branched or unbranched carbon chain that has 1 or more (e.g., 1, 2, 3 or 4) double bonds. For example, $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl.

As described herein, $(C_3-C_{20})$alkenoyl is $(C_2-C_{19})$alkenyl$)$-$C(=O)$—, wherein the $(C_2-C_{19})$alkenyl is a $C_2$ to $C_{19}$ branched or unbranched carbon chain that has 1 or more (e.g., 1, 2, 3 or 4) double bonds.

As used herein the term "salt" includes base addition, acid addition and quaternary salts. Compounds of the invention which are acidic can form salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like.

In cases where compounds are sufficiently acidic, a salt of a compound of formula I can be useful as an intermediate for isolating or purifying a compound of formula I.

All numerical values within the detailed description and the claims herein are modified by "about" or "approximately" the indicated value, and take into account experimental error and variations that would be expected by a person having ordinary skill in the art.

As discussed herein, the lubricating oil compositions of this disclosure may be used to reduce friction in engines or any other mechanical component, which may be lubricated with a lubricating oil. Mechanical components are known in the art and include, but are not limited to, bearings, gears, pistons, rods, pins, rings, pumps, valves, shafts, assemblies, valvetrains, camshafts, crankshafts, balance shafts, cylinders, sumps and housings.

Certain Methods for Preparing Compounds of Formula (I)

Generally, compounds of formula (I), as well as synthetic intermediates that can be used for preparing compounds of formula (I), can be prepared as illustrated in the following Schemes and Examples. It is understood that variable groups shown in the Schemes below (e.g., $Pg_1$, $Pg_2$, $R_1$, $R_2$, $R_3$, and $R_4$) can represent the final corresponding groups present in a compound of formula (I) or that these groups can represent groups that can be converted to the final corresponding groups present in a compound of formula (I) at a convenient point in a synthetic sequence. For example, in the Schemes below, the variable groups can contain one or more protecting groups (i.e., $Pg_1$ and $Pg_2$) that can be removed at a convenient point in a synthetic sequence to provide the final corresponding groups in the compound of formula (I). As used herein, $Pg_1$ and $Pg_2$ may be any suitable protecting group. Processes for preparing compounds of formula (I) are provided as further embodiments.

Scheme 1.

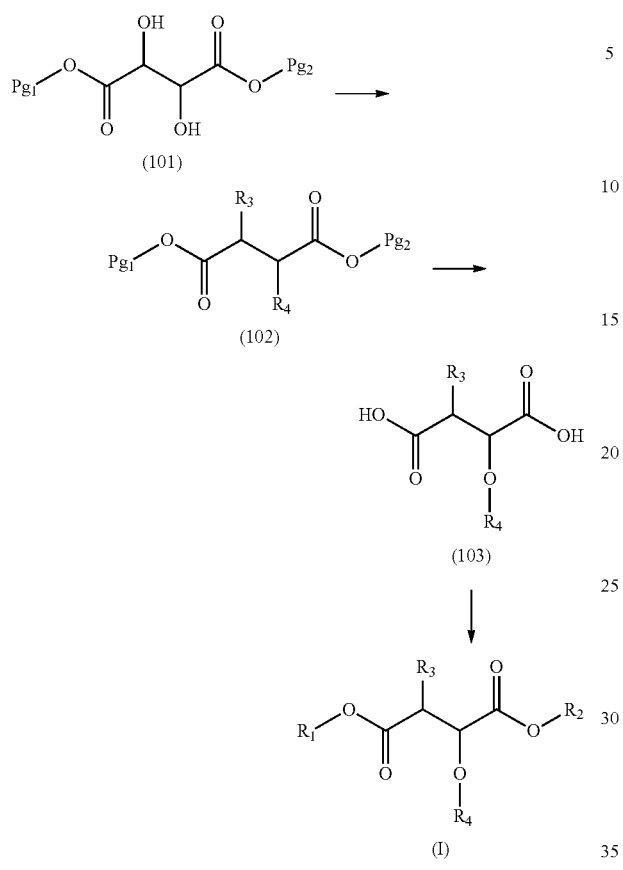

Scheme 3.

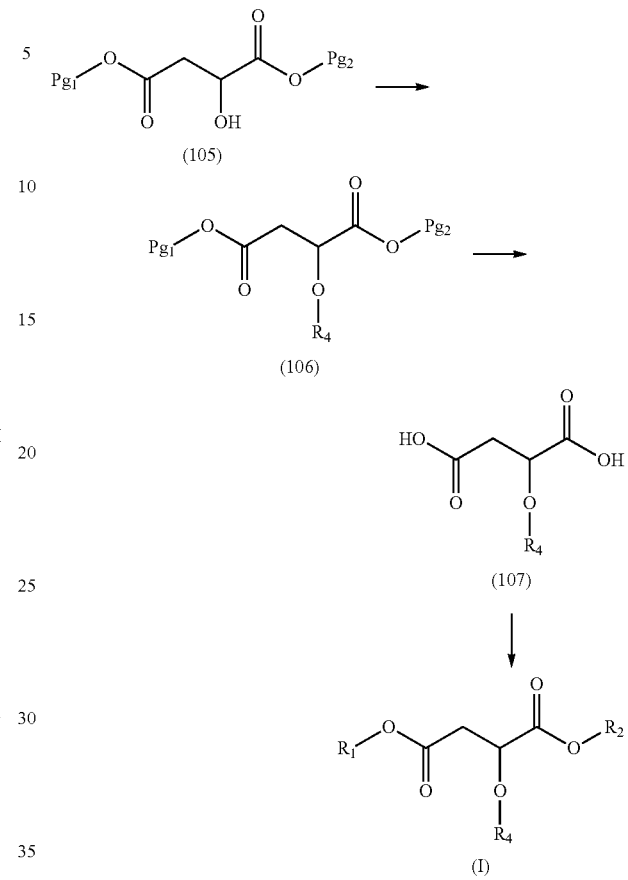

As shown in Scheme 1, the protected diacid (101) can be alkylated or acylated to provide compound (102). Deprotection (i.e., removal of $Pg_1$ and $Pg_2$) of compound (102) provides diacid (103), which is a compound of formula (I), wherein $R_1$ and $R_2$ are each hydrogen. Diacid (103) can then be converted to a compound of formula (I), wherein $R_1$ and $R_2$ are each independently other than hydrogen, by standard means.

As shown in Scheme 3, the protected diacid (105) can be alkylated or acylated to provide compound (106). Deprotection (i.e., removal of $Pg_1$ and $Pg_2$) of compound (106) provides diacid (107), which is a compound of formula (I), wherein $R_1$ and $R_2$ are each hydrogen. Diacid (107) can then be converted to a compound of formula (I), wherein $R_1$ and $R_2$ are each independently other than hydrogen, by standard means.

Scheme 2.

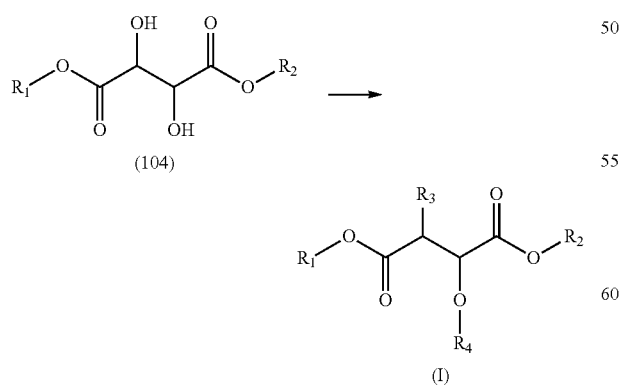

Scheme 4.

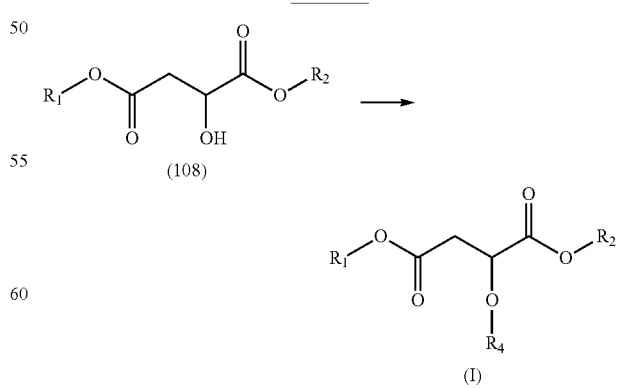

As shown in Scheme 2, diol (104) can be converted to a compound of formula (I) by alkylation or acylation.

As shown in Scheme 4, diol (108) can be converted to a compound of formula (I) by alkylation or acylation.

The invention will now be illustrated by the following non-limiting Examples.

EXAMPLES

Motivated by growing environmental concerns regarding climate change and greenhouse emissions, many industries have sought to reduce $CO_2$ emissions. This interest has resulted in increased research efforts to improve energy efficiency, particularly in the petrochemical and automobile industries, as an increase in fuel economy correlates to a decrease in vehicle emissions (Remmert, et al., SAE International Journal of Fuels and Lubricants 2013, 6, (3), 677-690). Extensive research has focused on improving fuel economy through the use of friction modifiers (FMs) as both a cost-effective and robust means to curtail vehicle emissions (Tang, Z.; Li, S., Current Opinion in Solid State and Materials Science 2014, 18, (3), 119-139).

FMs are lubricant additives that improve lubricity of base oil friction profiles to enhance fuel economy (Tang, Z.; Li, S., Current Opinion in Solid State and Materials Science 2014, 18, (3), 119-139). These additives are commonly used when boundary and mixed lubrication regimes exist (e.g., engines, gears). Boundary lubrication describes a system in which fluid films are unable to form between metal surfaces resulting in high friction, wear, and energy efficiency losses. These losses in efficiency increase both fuel consumption and emissions (Remmert, et al., SAE International Journal of Fuels and Lubricants 2013, 6, (3), 677-690). Low viscosity lubricants have been shown to improve fuel efficiency through reduced fluid friction, but detrimentally impact both boundary and mixed lubrication regimes. The debits from low viscosity basestocks can be offset through the use of more efficacious FMs (Phillips, et al., SAE Technical Paper 2007-01-4143 2007).

FMs are divided into two classes, organo-molybdenum and organic molecules, the latter receiving considerable attention due to their more environmentally friendly nature (e.g., sulfur-free, ashless) (Tang, Z.; Li, S., Current Opinion in Solid State and Materials Science 2014, 18, (3), 119-139). Organic FMs are typically surface-active molecules, possessing long-chain aliphatic tails with a polar head group (e.g., carboxylic acid, alcohol, amine, and phosphate) that physically adsorb or chemically interact with a metallic surface. Upon interacting with a metal surface, the aliphatic chains can orient themselves to maximize van der Waals interactions between adjacent hydrocarbons. While different modes of action for organic FMs boundary lubrication have been suggested (i.e., thick film model (Allen, C. M.; Drauglis, E., Wear 1969, 14, 363), liquid slip (Hersey, M. D., Journal of American Society of Mechanical Engineers 1933, 55, 561)), the most commonly described mechanism is the monolayer model (FIG. 1). FMs interact with a metal substrate, physically and/or chemically, to provide effective lubricity and prevent direct metal/metal contact. Extensive research has demonstrated that systems with organic FM monolayers have a lower coefficient of friction (COF) and are sufficient to prevent direct metal/metal contact. Research has also established that the extent of friction reduction may be influenced by both the polar head group and aliphatic chain length (Jahanmir, S., Wear 1985, 102, (4), 331; Jahanmir, S.; Beltzer, M., Journal Of Tribology 1986, 108, 109-116). The former impacts the method of interaction (physical vs. chemical) and adsorption strength onto the metal surface, whereas the increasing carbon chain length of the latter improves lubricity through increased cohesive energy between adjacent aliphatic chains.

Figure 2:
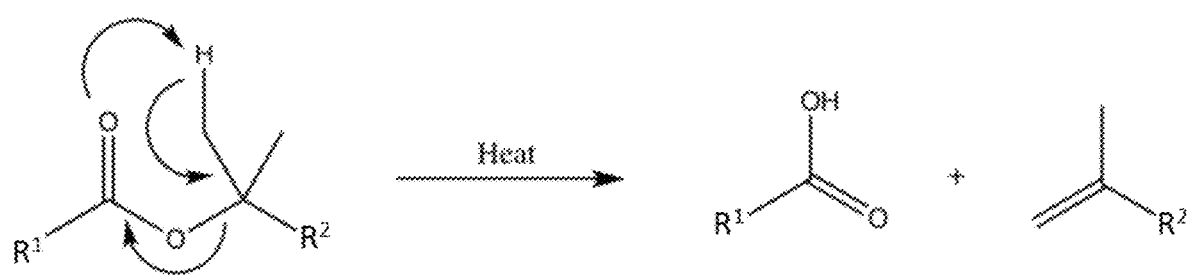
FIG. 2. Mechanism of β-ester pyrolysis of a tertiary-alkyl ester releasing a carboxylic acid capable of reducing friction and olefin by-product.

Although straight-chained fatty acids offer the advantage of being biorenewable (Tang, Z.; Li, S., Current Opinion in Solid State and Materials Science 2014, 18, (3), 119-139) and their mechanism-of-action has been well-established in boundary film models (Bowden, et al., Nature 1945, 156, 97-101), notable disadvantages hinder their efficacy. Fatty acids such as stearic acid are particularly effective in reducing the COF, but exhibit poor solubility in common synthetic oils. Furthermore, Minami et al. noted that while linear fatty acids are effective in reducing friction in mineral oil, this effect is not consistent in more polar synthetic oils (e.g., polyesters and polyethers) (Minami, I.; Mori, S., Lubrication Science 2007, 19, (2), 127-149). Lastly, while only monolayers are needed to reduce friction, it is necessary to replenish organic FMs as their degradation reduces the friction performance with time. To enhance efficacy, overcome poor solubility, and provide sustained release of organic FMs, thermocleavable esters that undergo a β-ester pyrolysis to generate carboxylic acids were investigated (FIG. 2) (Helgesen, M.; Krebs, F. C., Macromolecules 2010, 43, (3), 1253-1260; Peterson, et al., Macromolecules 2008, 41, 8986-8994), which improved upon traditional FMs.

As described herein, to replenish organic friction modifier stocks in base oil lubricants, tertiary ester derivatives of fatty acid-containing dicarboxylic acids were investigated. Specifically, as described in Examples 1-14 below, a series of fatty acid containing dicarboxylic acids and diesters were synthesized and characterized (see, FIG. 12 showing processes and intermediates for preparing compounds of the invention). A series of fatty acid-containing dicarboxylic acids were first developed based on a tartaric acid backbone and their friction modifying capabilities assessed. Coefficient of friction studies illustrated that friction-modifying capabilities were heavily influenced by polar head group type (i.e., carboxylic acid, ester) and chemical bond to tartaric acid (i.e., ester, ether). Thermogravimetric analysis coupled gasphase Fourier transform infrared spectroscopy revealed that fatty acid-containing dicarboxylic acids degraded into their respective fatty acids at elevated temperatures. Controlled release studies were conducted on a compound modified with thermocleavable esters, and showed sustained friction modifying activity through the course of the entire study. These systems are ideal candidates for the controlled delivery of friction modifiers, which can increase engine efficiency and reduce fuel consumption, effectively reducing vehicle emissions.

Materials. Stearic acid was acquired from Acros Organics (Morris Plains, N.J.) and subsequently recrystallized with dichloromethane (DCM) and ethanol. 1-Ethyl-3-(3-dimethylaminopropyl)carbodiimide (EDCI) was purchased from AK Scientific (Union City, Calif.). Diacetyl L-tartaric acid and dibenzyl L-tartrate were obtained from TCI (Portland, Oreg.). Di-tert-butyl L-tartrate was prepared as previously published (Uray, et al., Tetrahedron 1988, 44, (14), 4357-4362). Standard ball and disk specimens for High Frequency Reciprocating Rig (HFRR) experiments were purchased from PCS Instruments (London, UK). All other reagents, solvents, and fine chemicals were purchased from Aldrich (Milwaukee, Wis.) and used as received.

$^1$H and $^{13}$C NMR and FT-IR Spectroscopies. Proton ($^1$H) and carbon ($^{13}$C) nuclear magnetic resonance spectra were obtained with Varian 400 or 500 MHz using deuterated dimethyl sulfoxide (DMSO-$_{d6}$) as an internal reference and solvent or deuterated chloroform ($CDCl_3$) with tetramethylsilane as an internal reference. A Thermo Nicolet/Avatar 360 spectrometer was used to obtain Fourier transform infrared (FT-IR) spectra. Samples were prepared by either grinding sample (1-3 wt %) with potassium bromide (KBr) and pressing into a disc using an IR pellet die (International Crystal Laboratories, Garfield, N.J.) or solvent casting via dichloromethane (DCM) or chloroform ($CHCl_3$) to acquire a thin film on sodium chloride (NaCl) plates. Each spectrum was an average of 32 scans.

Molecular Weight. Small molecule molecular weights were analyzed via mass spectrometry (MS). A Finnigan LCQ-DUO running on Xcalibur software and an adjustable atmospheric pressure ionization electrospray ion source (API-ESI Ion Source) was used with a pressure of $0.8 \times 10^{-5}$ Torr and 150° C. API temperature. Samples dissolved in methanol (MeOH) (<10 μg/mL) were injected via a glass syringe.

Thermal Properties. Melting ($T_m$) temperatures were obtained using differential scanning calorimetry (DSC). DSC measurements were conducted on a TA Instrument Q200 and analyzed via TA Instruments Universal Analysis 2000 version 4.5A software. Samples (4-6 mg) were heated under nitrogen atmosphere from ambient to 200° C. at a heating rate of 10° C./min. Thermal stability at 200° C. was determined using Perkin-Elmer Pyris 1 TGA system equipped with TAC 7/DX instrument controller and Perkin-Elmer Pyris software for data collection. Samples (5-10 mg) were heated under air (20 mL/min) at 200° C. isothermally for 2 hours and the mass loss was monitored.

Example 1

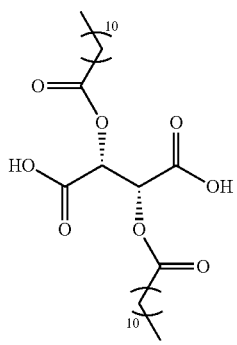

(1)

Synthesis of Compound (1) (i.e., T12; 2,3-bis(lauroyl) tartaric acid). Following established methods (Faig, et al., *Biomacromolecules* 2014, 15, (9), 3328-37), tartaric acid ((151) 4.05 g, 27 mmol) was acylated at the vicinal hydroxyl groups by refluxing neat in lauroyl chloride (45.9 mL, 119 mmol) with zinc chloride ($ZnCl_2$, 1.15 g, 8 mmol) as a catalyst to provide compound (1), as confirmed by the presence of laurate ester peaks in $^1H$ NMR and ester appearance in $^{13}C$ NMR and FTIR. Yield: 11.57 g, 89% (white solid). $^1$H-NMR (400 MHz, $CDCl_3$): δ 5.77 (s, 2H), 2.43 (q, 4H), 1.64 (m, 4H), 1.26 (m, 32H), 0.88 (t, 6H). $^{13}$C-NMR (MHz, $CDCl_3$): δ 172.53, 171.21, 70.04, 33.57, 31.92, 29.63, 29.47, 29.36, 29.22, 28.96, 27.62, 24.64, 22.69, 14.12. IR ($cm^{-1}$, $CHCl_3$): ESI-MS m/z: 513.1 $[M-1]^-$. $T_m$=74-76° C.

Example 2

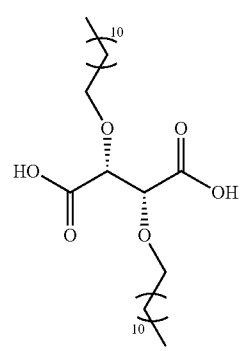

(2)

Synthesis of Compound (2) (i.e., T(12-O); 2,3-bis(dodecyl) tartaric acid). Compound (2) was prepared using a two-step approach (Zhang, et al., *Biomaterials* 2016, 84, 230-240). Di-t-butyl L-tartrate ((152), 200 mg, 0.76 mmol), synthesized following literature protocols (Uray, et al., *Tetrahedron* 1988, 44, (14), 4357-4362), was alkylated with 1-bromododecane (0.42 mL, 1.68 mmol) in the presence of sodium hydride (64 mg, 1.6 mmol) to provide di-t-butyl 2, 3-bis(dodecyloxyl) tartrate. di-t-butyl 2, 3-bis(dodecyloxyl) tartrate was deprotected with trifluoroacetic acid (TFA) (1.4 mL, 18.37 mmol) in anhydrous DCM to provide compound (2), which was confirmed by the disappearance of the t-butyl peaks in $^1H$ NMR. Two-step yield: 200 mg, 54% (white solid). $^1$H-NMR (400 MHz, $CDCl_3$): 4.38 (s, 2H), 3.69 (m, 2H), 3.47 (m, 2H), 1.59 (m, 4H), 1.24 (br, 36H), 0.88 (t, 6H). $^{13}$C-NMR ($CDCl_3$): 172.49, 79.40, 73.64, 34.20, 31.91, 29.63, 29.61, 29.57, 29.49, 29.35, 29.33, 29.27, 25.72, 22.67, 14.10. IR ($cm^{-1}$, $CHCl_3$): 3100-3600 (COOH), 1744 (C=O). ESI-MS m/z: 485.7 $[M-1]^-$.

Example 3

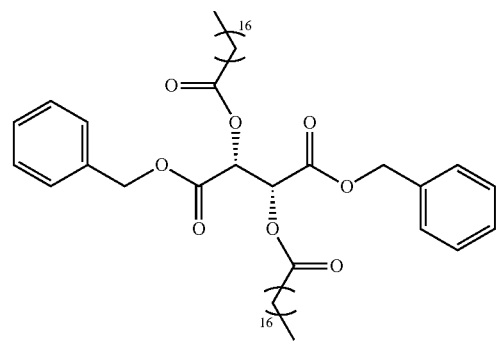

(3)

Synthesis of Compound (3) (i.e., Dibenzyl 2,3-bis (stearoyl) tartrate; Dibenzyl T18 (DBT18)). Dibenzyl L-tartrate (150) was esterified with stearic acid using carbodiimide coupling with EDCI and DMAP to provide compound (3). Specifically, dibenzyl L-tartrate ((150) 1.00 g, 3.03 mmol), stearic acid (1.89 g, 6.67 mmol), 4-dimethylaminopyridine (DMAP, 0.81 g, 6.67 mmol) and EDCI (1.73 g, 9.08 mmol) were dissolved in 20 mL anhydrous dichloromethane (DCM) under Argon. Thin layer chromatography (TLC, 4:1 hexanes:ethyl acetate) was used to monitor the reaction. Upon dibenzyl L-tartrate consumption, the reaction mixture was diluted with DCM (80 mL), transferred to a separatory funnel, and washed 3×100 mL 10% potassium bisulfate (KHSO$_4$). The organic layer was collected, dried over MgSO$_4$, isolated and concentrated in vacuo. Crude product was purified on silica gel via column chromatography using 4:1 hexanes:ethyl acetate eluent to provide compound (3). Successful product formation was evident through $^1$H NMR by the downfield shift in the tartaric acid methine peak (5.76 ppm) and the splitting of the methylene protons adjacent of stearic acid's carbonyl group (2.28 and 2.13 ppm). Compound (3) synthesis was further corroborated by the ester appearance in $^{13}$C NMR and FTIR spectrums. Yield: 2.40 g, 92% (white powder). $^1$H NMR (400 MHz, CDCl$_3$): δ 7.33 (m, 10H), 5.76 (s, 2H), 5.23 (d, 2H), 5.17 (d, 2H), 2.28 (m, 2H), 2.13 (m, 2H), 1.53 (m, 4H), 1.26 (bm, 56H), 0.89 (t, 6H). $^{13}$C NMR (CDCl$_3$): δ 172.41, 165.73, 134.77, 128.64, 128.53, 70.54, 67.68, 33.42, 31.96, 29.75, 29.70, 29.67, 29.49, 29.41, 29.27, 28.98, 24.59, 22.73, 14.18. IR (cm$^{-1}$, DCM): 1758 (C=O). ESI-MS m/z: 885.2 [M+Na]$^+$. T$_m$=75° C.

Example 4

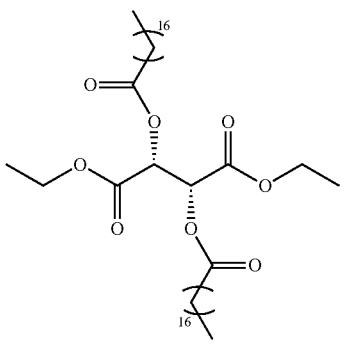

(4)

Synthesis of Compound (4) (i.e., Di-ethyl 2,3-bis (stearoyl) tartaric acid; Diethyl T18 (DET18)). Compound (4) was synthesized similarly to compound (3) using diethyl L-tartrate ((154), 0.50 mL, 2.92 mmol), stearic acid (1.83 g, 6.42 mmol), DMAP (0.79 g, 6.42 mmol) and EDCI (1.67 g, 8.76 mmol). Yield: 2.05 g, 95% (white powder). $^1$H NMR (500 MHz, CDCl$_3$): δ 5.71 (s, 2H), 4.22 (m, 4H), 2.41 (m, 4H), 1.64 (m, 4H), 1.25 (bm, 56H), 0.88 (t, 6H). $^{13}$C NMR (CDCl$_3$): δ 172.54, 165.94, 70.62, 62.15, 33.67, 31.93, 29.71, 29.70, 29.67, 29.62, 29.46, 29.38, 29.25, 28.99, 24.78, 22.71, 14.14, 14.07. IR (cm$^{-1}$, DCM): 1763 (C=O). ESI-MS m/z: 761.5 [M+Na]$^+$. T$_m$=58° C.

Example 5

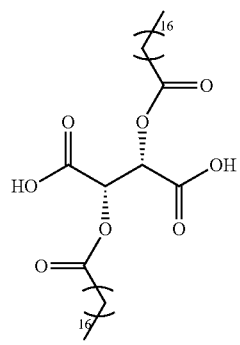

(5)

Synthesis of Compound (5) (i.e., 2,3-bis(stearoyl) tartaric acid; T18). Compound (3, 1.00 g, 1.16 mmol) was dissolved in 20 mL anhydrous DCM under Argon. Palladium on carbon (Pd/C, 10 wt. %) was added and the atmosphere subsequently evacuated and charged with hydrogen. TLC was used to monitor the reaction (4:1 hexanes:ethyl acetate). Following consumption of compound (3), the reaction was filtered through a celite-packed fritted funnel and concentrated in vacuo. The resulting white powder was triturated in methanol and compound (5) was isolated via vacuum filtration. The absence of aromatic and benzyl protons in $^1$H NMR, disappearance of aromatic traces, and emergence of carboxylic acid functionalities in $^{13}$C NMR and FTIR confirmed the final product. Yield: 736 mg, 93% (white powder). $^1$H-NMR (400 MHz, CDCl$_3$ with DMSO): δ 5.51 (s, 2H), 2.26 (m, 4H), 1.47 (m, 4H), 1.09 (br, 56H), 0.72 (t, 6H). $^{13}$C-NMR (CDCl$_3$): δ 172.45, 70.67, 33.64, 31.78, 29.57, 29.55, 29.52, 29.35, 29.23, 29.15, 28.90, 24.59, 22.55, 14.05. IR (cm$^{-1}$, DCM): 1751 (C=O, ester), 1735 (C=O, acid). ESI-MS m/z: 681.4 [M-H]. T$_m$=94-96° C.

Example 6

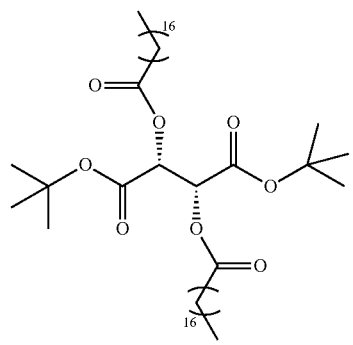

(6)

Synthesis of Compound (6) (i.e., Di-t-butyl 2,3-bis (stearoyl) tartaric acid; Di-t-butyl T18). Carbodiimide coupling of di-t-butyl tartrate with stearic acid provided compound (6). Specifically, following a modified procedure (Faig, et al., *Biomacromolecules* 2014, 15, (9), 3328-37), di-tert-butyl L-tartrate (100 mg, 0.38 mmol), stearic acid (239 mg, 0.84 mmol), EDCI (219 mg, 1.14 mmol), and DMAP (100 mg, 0.84 mmol) were dissolved in 4 mL anhydrous DCM under argon. The reaction stirred overnight at room temperature. The reaction mixture was washed with 10% $KHSO_4$ (2×15 mL) and brine (1×15 mL). The crude mixture was dried over $MgSO_4$, filtered, and concentrated in vacuo. The crude product was precipitated in chilled hexane and isolated via vacuum filtration. The final product was substantiated by the emergence stearate protons in $^1H$ NMR and appearance of the stearate ester in $^{13}C$ NMR and FTIR. Yield: 230 mg, 76% (white solid). $^1$H-NMR (400 MHz, $CDCl_3$): δ 5.61 (s, 2H), 2.40 (m, 4H), 1.62 (m, 4H), 1.43 (s, 18H), 1.24 (br, 56H), 0.87 (t, 6H). $^{13}$C-NMR (500 MHz, $CDCl_3$): δ 172.54, 164.89, 83.24, 70.98, 33.65, 31.92, 29.76, 29.70, 29.68, 29.66, 29, 60, 29.44, 29.37, 29.23, 29.10, 27.86, 24.71, 22.69, 14.12. IR ($cm^{-1}$, $CHCl_3$): 1757 (C=O). ESI-MS m/z: 817.2 $[M+Na]^+$. $T_m$=44-45° C.

Example 7

(7)

Synthesis of Compound (7) (i.e., 2,3-bis(palmitoyl) tartaric acid; T16). Compound (7) was synthesized through a two-step method, similar to compound (5) using DBT (1.00 g, 3.03 mmol), palmitic acid (1.70 g, 6.67 mmol), EDCI (1.74 g, 9.09 mmol) and DMAP (813 mg, 6.67 mmol) to acquire DBT16. Yield: 2.10 g, 86% (white powder). $^1$H-NMR (400 MHz, $CDCl_3$): δ 7.32 (m, 10H), 5.75 (s, 2H), 5.16 (q, 4H), 2.21 (m, 4H), 1.53 (m, 4H), 1.25 (br, 48H), 0.88 (t, 6H). $^{13}$C-NMR ($CDCl_3$): δ 172.38, 165.73, 134.78, 128.62, 128.60, 128.47, 70.55, 67.67, 33.43, 31.92, 29.70, 29.66, 29.62, 29.46, 29.36, 29.23, 28.96, 24.58, 22.69, 14.11.

DBT16 (2.10 g, 2.60 mmol) was then deprotected using Pd/C (10 wt %) to acquire T16. Yield: 1.50 g, 94% (white powder). $^1$H-NMR (400 MHz, $CDCl_3$): δ $^1$H-NMR (400 MHz, $CDCl_3$ with DMSO): δ 5.56 (s, 2H), 2.30 (m, 4H), 1.51 (m, 4H), 1.32 (br, 48H), 0.76 (t, 6H). $^{13}$C-NMR ($CDCl_3$): δ 172.49, 70.76, 33.69, 31.86, 29.57, 29.53, 29.40, 29.24, 29.17, 28.96, 28.93, 24.64, 22.58, 14.05. IR ($cm^{-1}$, DCM): 1751 (C=O, ester) ESI-MS m/z: 625.3 [M-H]-. Tm=84-86° C.

Example 8

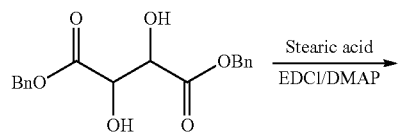

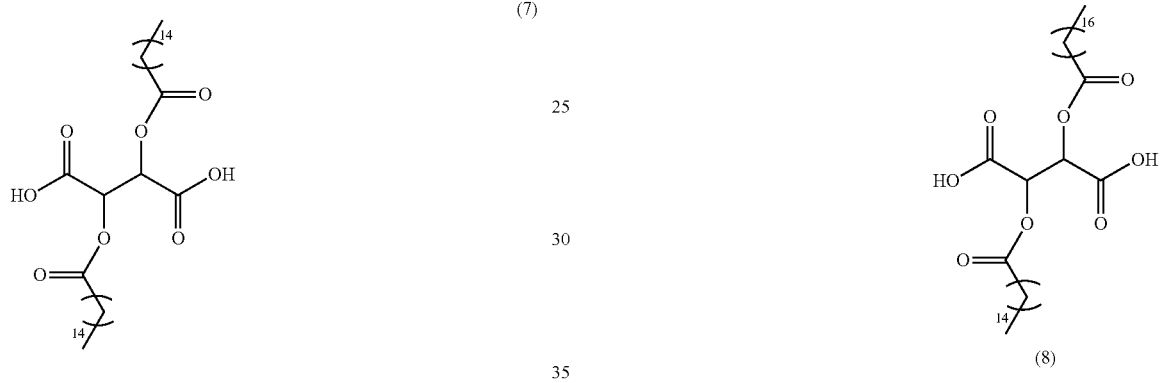

Synthesis of Compound (8, T16-co-T18). Compound 7 was synthesized by first mono-conjugating stearic acid to DBT. In brief, DBT (5.00 g, 15.14 mmol), EDCI (867 mg, 4.54 mmol) and DMAP (407 mg, 3.33 mol) were dissolved in 40 mL anhydrous DCM under nitrogen. Stearic acid (861 mg, 3.03 mmol), dissolved in 12 mL 5:1 anhydrous DCM:DMF, was added drop-wise over 6 h. After stirring overnight, the reaction was washed 3×50 mL 10% $KHSO_4$ and once with 50 mL brine. The organic layer was dried over $MgSO_4$, isolated via vacuum filtration, and concentrated in vacuo Crude product was purified on silica gel via column chromatography using 9:1 hexanes:ethyl acetate to acquire mono-stearic DBT intermediate. Yield: 1.21 g, 67% (white powder). $^1$H-NMR (500 MHz, $CDCl_3$): 7.32 (m, 10H), 5.51 (s, 1H), 5.22 (m, 4H), 4.80 (d, 1H), 3.10 (d, 1H) 2.19 (split m, 2H), 1.51 (quint, 2H), 1.26 (br, 28H), 0.88 (t, 3H).

The secondary alcohol of mono-stearic DBT was then conjugated to palmitic acid via carbodiimide coupling. Mono-stearic DBT (215 mg, 0.360 mmol), palmitic acid (102 mg, 0.396 mmol), EDCI (103 mg, 0.540 mmol), and DMAP (48 mg, 0.396 mmol) were dissolved in 10 mL anhydrous DCM under argon. Upon mono-stearic DBT consumption, as indicated by TLC (4:1 hexanes:ethyl acetate eluent) the reaction was stopped and organic layer washed 3×25 mL 10% $KHSO_4$ and once with 25 mL brine. The organic layer was dried over $MgSO_4$, isolated via vacuum filtration, and concentrated in vacuo. Pure DBT(16-co-T18) was obtained via silica gel column chromatography using 9:1 hexanes:ethyl acetate eluent. Yield: 261 mg, 87% (white powder). $^1$H-NMR (400 MHz, $CDCl_3$): δ 7.30 (m, 10H), 5.72 (s, 2H), 5.18 (q, 4H), 2.24 (m, 4H), 1.51 (m, 4H), 1.27 (br, 52H), 0.88 (t, 6H).

DBT(T16-co-T18) (875 mg, 1.04 mmol) was dissolved in 15 mL anhydrous DCM. Pd/C (10 wt %) was added and the atmosphere evacuated and subsequently charged with hydrogen. The reaction progress was monitored via TLC (4:1 hexanes:ethyl acetate eluent). Upon DBT(T16-co-T18) consumption, the reaction was filtered through a celite-packed fritted funnel and concentrated in vacuo. The resulting white powder was triturated in methanol and compound (8) was isolated via vacuum filtration. Yield: 631 mg, 91% (white powder). $^1$H-NMR (400 MHz, CDCl$_3$): δ 5.56 (s, 2H), 2.30 (m, 4H), 1.51 (m, 4H), 1.32 (br, 48H), 0.76 (t, 6H). $^{13}$C-NMR (CDCl$_3$): δ 172.49, 70.76, 33.69, 31.86, 29.57, 29.53, 29.40, 29.24, 29.17, 28.96, 28.93, 24.64, 22.58, 14.05.

Example 9

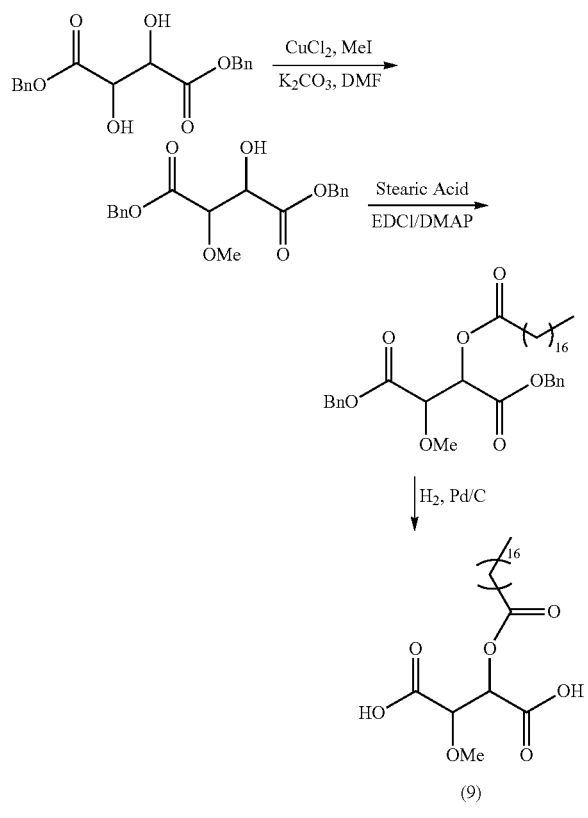

Synthesis of Compound (9, Mono-Methyl T18). Following a published procedure (Maki et al., *Tetrahedron Letters* 2009, 50, 1466-1468), dibenzyl L-tartrate (1.00 g, 3.00 mmol), methyl iodide (MeI, 1.87 mL, 30.00 mmol), copper (II) chloride (CuCl$_2$, 40 mg, 0.30 mmol), and potassium carbonate (K$_2$CO$_3$, 622 mg, 4.50 mmol) were weighed and dissolved in 25 mL DMF. The reaction was stirred for 36 h. The solvent was removed in vacuo and resuspended in 50 mL DCM. The organic layer was washed with 0.1 N HCl (1×100 mL) and extracted with ethyl acetate (3×50 mL). The combined organic layer was dried over MgSO4, filtered, and concentrated in vacuo. The crude product was purified on silica gel via column chromatography using a hexane: ethyl acetate gradient (95:5 to 90:10). Yield: 797 mg, 80% (white solid). $^1$H-NMR (400 MHz, CDCl$_3$): δ 7.36 (m, 10H), 5.23 (m, 4H), 4.64 (d, 2H), 4.18 (s, 1H), 3.32 (s, 3H).

Mono-methoxy dibenzyl T18 was prepared in a manner similar to dibenzyl T16. In brief, mono-methoxy dibenzyl L-tartrate (797 mg, 2.31 mmol), stearic acid (724 mg, 2.55 mmol), EDC•HCl (663 mg, 3.47 mmol), and DMAP (311 mg, 2.55 mmol) were dissolved in 20 mL anhydrous DCM under argon and the reaction stirred overnight at room temperature. Yield: 1.4 g, quantitative yield (white solid). $^1$H-NMR (400 MHz, CDCl$_3$): δ 7.33 (m, 10H), 5.62 (d, 1H), 5.20 (m, 4H), 4.39 (d, 1H), 3.38 (s, 3H), 2.22 (m, 2H), 1.52 (m, 2H), 1.26 (br, 28H), 0.88 (t, 3H). ESI-MS m/z: 633.8 [M+Na]$^+$.

Mono-methoxy T18 was prepared in a similar manner to T16. In brief, mono-methoxy dibenzyl T18 (1.40 g, 2.29 mmol) was dissolved in 20 mL DCM followed by addition of 0.14 g palladium on carbon (Pd/C, 10 wt %). The reaction stirred under H$_2$ gas for 24 h. Yield: 937 mg, 95% (off-white solid). $^1$H-NMR (400 MHz, CDCl$_3$): δ 5.57 (s, 1H), 4.37 (s, 1H), 3.51 (s, 3H), 2.40 (q, 4H), 1.61 (m, 4H), 1.24 (br, 28H), 0.86 (t, 3H). $^{13}$C-NMR (CDCl$_3$): δ 172.77, 79.31, 72.25, 59.90, 33.79, 31.90, 29.68, 29.65, 29.63, 29.62, 29.46, 29.33, 29.25, 29.05, 24.73, 22.66, 14.10.

Example 10

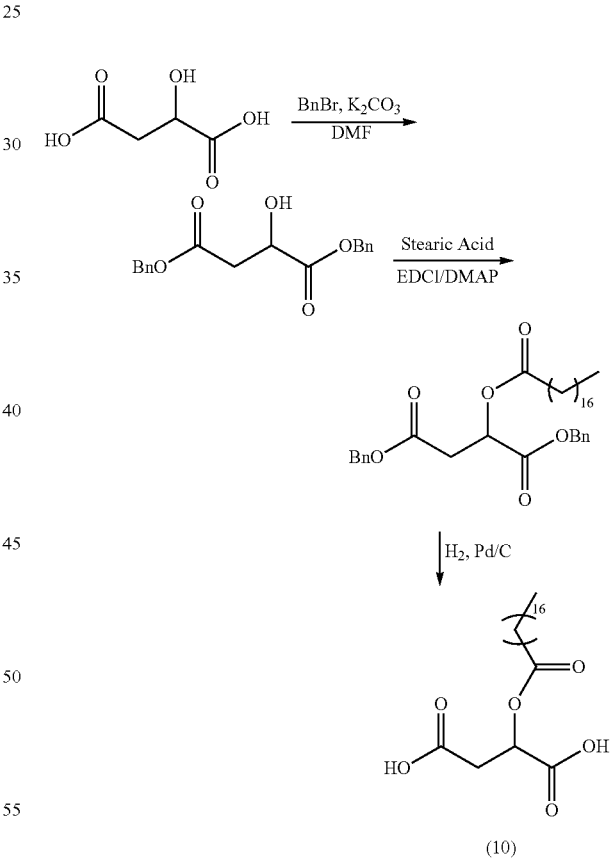

Synthesis of Compound (10, M18). Compound 10 was synthesized using a three-step method. First, malic acid (3.00 g, 22.37 mmol) and anhydrous potassium carbonate (K$_2$CO$_3$, 7.42 g, 53.70 mmol), combined in a round bottom flask and 25 mL anhydrous DMF added under argon. Benzyl bromide (BnBr, 7.97 mL, 67.12 mmol) was then added and the reaction heated to 45° C. After stirring overnight, excess DMF was removed using a rotary evaporator and the resulting white paste dissolved in 200 mL 1:1 ethyl acteate:

saturated aquoues NaHCO₃. The organic layer was washed 3×100 mL sat. aq. NaHCO₃, dried over Na₂SO₄, isolated via vacuum filtration and concentration in vacuo. The resulting oil was redissolved in acetonitrile (100 mL) and washed 3×50 mL hexanes. The acetonitrile layer was then concentrated in vacuo to acquire pure dibenzyl malate (DBM). Yield: 6.33 g 90% (clear oil). ¹H-NMR (400 MHz, CDCl₃): δ 7.32 (m, 10H), 5.16 (split, 4H), 4.52 (s, 1H), 3.21 (s, 1H), 2.87 (split, 2H).

Stearic acid was then coupled to dibenzyl malate using previously developed methods. In short, Dibenzyl malate (2.00 g, 6.37 mmol), stearic acid (1.99 g, 7.00 mmol), EDCI (1.84 g, 9.55 mmol), and DMAP (856 mg, 7.00 mmol) were dissolved in 20 mL anhydrous DCM under argon. Following Dibenzyl malate consumption, as indicated by TLC (4:1 hexanes:ethyl acetate), the reaction was stopped and washed 3×100 mL 10% KHSO₄. The organic layer was dried over Na₂SO₄, isolated via vacuum filtration, and concentrated in vacuo. Crude DBM18 was then purified via silica gel column chromatography using 4:1 hexanes:ethyl acetate eluent to acquire pure product. Yield: 2.68 g, 72% (white powder). ¹H-NMR (400 MHz, CDCl₃): δ 7.29 (m, 10H), 5.54 (t, 1H), 5.14 (m, 4H), 2.93 (d, 2H), 2.30 (m, 2H), 1.58 (quint, 2H), 1.26 (br, 28H), 0.88 (t, 3H).

Finally, DBM18 was selectively deprotected at its benzyl position. To do so, DBM18 (2.68 g, 4.62 mmol) was dissolved in 20 mL, 9:1 anhydrous DCM:methanol and Pd/C (10 wt %) was added. The atmosphere was evacuated and charged with hydrogen. Following DBM18 consumption, as indicated by TLC (4:1 hexanes:ethyl acetate eluent), the reaction was filtered through a celite-packed fritted funnel and wash 3×100 mL 95:5 DCM:methanol. The filtrate was then concentrated in vacuo and the resulting pale yellow solid subsequently triturated in 100 mL DCM. Pure 10 was isolated via vacuum filtration and dried under vacuum overnight. Yield: 1.80 g, 67% (white powder). ¹H-NMR (400 MHz, CDCl₃): δ 5.57 (t, 1H), 2.95 (d, 2H), 2.31 (m, 2H), 1.56 (quint, 2H), 1.26 (br, 28H), 0.88 (t, 3H).

Example 11

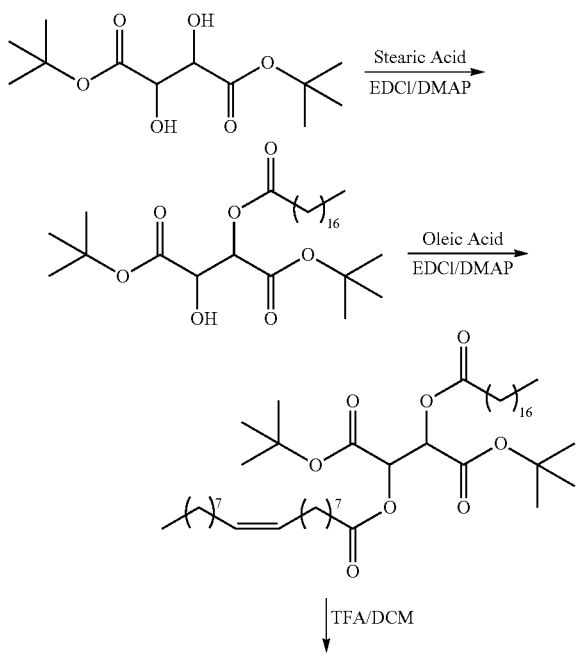

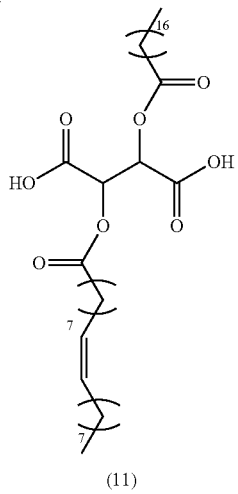

(11)

Synthesis of Compound (11, Mono-Oleic T18). Compound 11 was synthesized following a three-step approach. First, mono-conjugation of Di-t-butyl tartrate with stearic acid occurred using carbodiimide-coupling. To do so, Di-t-butyl tartrate (2.68 g, 10.2 mmol), EDCI (586 mg, 3.07 mmol), and DMAP (275 mg, 2.25 mmol) were dissolved in 35 mL anhydrous DCM under argon. Stearic acid, dissolved in 12 mL, 5:1 anhydrous DCM:DMF, was added drop-wise over 6 h. After stirring overnight, the reaction was washed 3×50 mL 10% KHSO₄. The organic layer was dried over MgSO₄, isolated via vacuum filtration, and concentrated in vacuo. Silica gel column chromatography with a 9:1 hexanes:ethyl acetate eluent was used to acquire pure mono-stearic di-t-butyl tartrate. Yield: 486 mg, 45% (white powder). ¹H-NMR (400 MHz, CDCl₃): δ 5.52 (s, 1H), 4.78 (d, 1H), 3.08 (d, 1H) 2.21 (split m, 2H), 1.52 (quint, 2H), 1.44 (s, 18H), 1.26 (br, 28H), 0.88 (t, 3H).

Oleic acid (270 μL, 0.823 mmol) was then conjugated to mono-stearic di-t-butyl tartrate (400 mg, 0.757 mmol) by dissolving in 20 mL anhydrous DCM under argon in the presence of EDCI (217 mg, 1.14 mmol) and DMAP (102 mg, 0.833 mmol). Upon mono-stearic di-t-butyl tartrate consumption, as indicated by TLC (9:1 hexanes:ethyl acetate), the reaction was washed 3×50 mL 10% KHSO₄ and 2×50 mL brine. The organic layer was dried over Na₂SO₄, isolated via vacuum filtration, and concentrated in vacuo. Crude product was further purified by silica gel column chromatography using 95:5 hexanes:ethyl acetate eluent to acquire mono-oleic-mono-stearic di-t-butyl tartrate. Yield: 522 mg, 87% (white powder). ¹H-NMR (400 MHz, CDCl₃): δ 5.61 (s, 2H), 5.34 (br, 2H), 2.41 (m, 4H), 2.00 (m, 4H), 1.65 (quint, 4H), 1.44 (s, 18H), 1.26 (br, 48H), 0.88 (t, 6H).

Mono-oleic-mono-stearic di-t-butyl tartrate (522 mg, 0.659 mmol) was then dissolved in 10 mL anhydrous DCM and TFA (2.32 mL, 26.34 mmol) added drop-wise over 15 minutes. The reaction was stirred overnight and the following morning concentrated in vacuo to acquire a brown paste. The paste was dissolved in 50 mL acetonitrile and washed 3×50 mL hexanes. The acetonitrile layer was concentrated in vacuo to acquire a beige paste. The beige paste was purified using chilled hexanes (40 mL, −20° C.) and centrifuged at 4,000 rpm for 3 minutes to acquire pure 11. Yield: 401 mg, 89% (off-white powder). ¹H-NMR (400 MHz, CDCl₃): δ 5.63 (s, 2H), 5.33 (br, 2H), 2.40 (m, 4H), 2.05 (m, 4H), 1.66 (quint, 4H), 1.26 (br, 48H), 0.88 (t, 6H).

Example 12

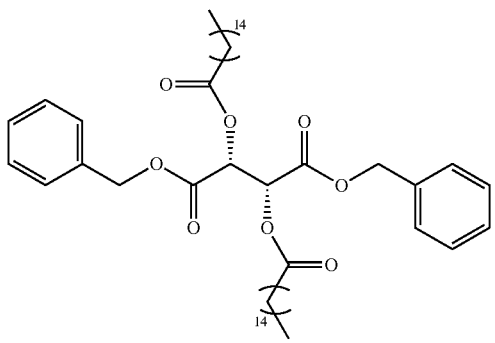

(12)

Synthesis of Compound (12) (i.e., Dibenzyl 2,3-Bis (Palmitoyl) Tartrate). Compound 12 was synthesized using a procedure similar to that used to generate compound 3. Yield: 2.10 g, 86.0% (white powder). 1H-NMR (400 MHz, CDCl3): δ 7.32 (m, 10H), 5.75 (s, 2H), 5.16 (q, 4H), 2.21 (m, 4H), 1.53 (m, 4H), 1.25 (br, 48H), 0.88 (t, 6H). 13C-NMR (CDCl3): δ 172.38, 165.73, 134.78, 128.62, 128.60, 128.47, 70.55, 67.67, 33.43, 31.92, 29.70, 29.66, 29.62, 29.46, 29.36, 29.23, 28.96, 24.58, 22.69, 14.11. IR (cm$^{-1}$, DCM): 1756 (C=O). ESI-MS m/z: 845.2 [M+K]$^{+}$.

Example 13

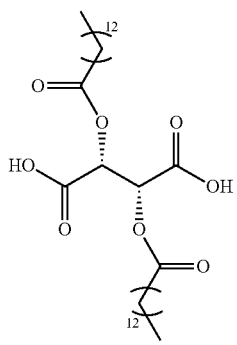

(13)

Synthesis of Compound (13) (i.e., 2,3-bis(myristoyl) tartaric acid). Compound 13 was synthesized using a procedure similar to that used to generate compound 1. Specifically, myristic acid was conjugated directly to tartaric acid from its acid chloride. Yield: 3.5 g, 89% (white solid). $^{1}$H-NMR (400 MHz, CDCl$_{3}$ with DMSO): δ 5.77 (s, 2H), 2.43 (q, 4H), 1.64 (m, 4H), 1.26 (m, 36H), 0.88 (t, 6H). $^{13}$C-NMR (MHz, CDCl$_{3}$): δ 172.53, 171.21, 70.04, 33.57, 31.92, 29.63, 29.47, 29.36, 29.22, 28.96, 27.62, 24.64, 22.69, 14.12. IR (cm$^{-1}$, CHCl$_{3}$): ESI-MS m/z: 569.3 [M−1]$^{-}$. Tm=80-82° C.

The thermal and friction modifying properties of a compound described herein may be evaluated using techniques which are well known in the art, e.g., using techniques described in Example 14.

Example 14

The thermal and friction modifying properties of the representative compounds were evaluated as described below.

Methods

Thermal Stability. Thermal stability at 200° C. was determined using Perkin-Elmer Pyris 1 thermogravimetric analysis (TGA) system equipped with TAC 7/DX instrument controller and Perkin-Elmer Pyris software for data collection. Samples (5-10 mg) were heated under air (20 mL/min) at 200° C. isothermally for 2 hours and monitoring mass loss.

Coefficient of Friction. The friction performance of each test oil, containing 1 wt % additive, was evaluated using a High Frequency Reciprocating Rig (HFRR, PCS Instruments, London, UK) under boundary conditions. A reference oil comprising a polyalphaolefin (PAO) blend without additives unless noted otherwise was subjected to identical test conditions to determine the COF in the absence of FMs. The HFRR testing was conducted with an oscillating ball-on-disk with the ball and disk contact immersed in test oil. The ball and disk hardware were purchased from PCS Instruments, London, UK. The ball was an AISI 52100 steel with a typical hardness of 800 Hv. The disk was an AISI 52100 steel with a typical hardness of 200 Hv. Tests were conducted under isothermal conditions at predetermined temperatures (e.g., 100 or 200° C.) for 2 hours. The HFRR parameters were a 400 g load (translates to a peak Hertzian contact pressure of about 1 GPa), 60 Hz reciprocating frequency, and 1.0 mm stroke length. A load cell was utilized to determine friction and film thickness between the ball and disk surfaces was inferred from electrical resistance measurements.

Thermal Decomposition Studies. Thermogravimetric analysis coupled with FTIR (TGA-FTIR) experiments were conducted using a TA instruments Q5000 with an external TGA Module (TA Instruments, Newcastle, Del.) interfaced with a Nicolet 6700 FT-IR spectrometer. An adjustable-flow chemical metering pump (0.5 inches water, McMaster-Carr, Robbinsville, N.J.) was used to draw evolved gas through the transferline towards the IR gas cell. All samples (20-30 mg) were heated in a platinum HT pan in a flowing atmosphere of air. Sample scans were heated from 25 to 400° C. at a heating rate of 10° C./min. Isothermal experiments were conducted at predetermined temperatures (i.e., 100, 150, and 200° C.). Sample decomposition temperatures (T$_d$) and mass loss were analyzed via TA Instruments Universal Analysis 2000 version 4.5A software, while the IR spectra of evolved gases were examined using Omnic 8.0 software (Thermo-Fisher Scientific, Walthan, Mass.).

FM Controlled Release. The controlled release of 5 from 6 was monitored using a controlled release unit (CRU) with a high temperature flow loop. Test oil was pumped repeatedly through a heated zone for a fixed amount of time. Bulk test oil, PAO-containing 1 wt % of 6 held at 130° C., was passed through a block heater at 215° C. at 4 mL/min. Aliquots of the bulk testing oil were removed at predetermined time points and subjected to HFRR analysis for 2 hours at 100° C.

Results

Synthesis and Characterization. Fatty acid-containing dicarboxylic acids were synthesized to assess the influence of incorporating long-chain aliphatic chains, capable of cohesive interactions between adjacent chains, on dicarboxylic acid motifs. A series of fatty acids (lauric, myristic, palmitic, and stearic) were conjugated to tartaric acid via either direct conjugation or a two-step method (FIGS. 12A-D). Following previously established methods (Faig, et al., *Biomacromolecules* 2014, 15, (9), 3328-37), tartaric acid was acylated at the vicinal hydroxyl groups by refluxing neat in alkanoyl chloride (i.e., lauroyl, myristoyl chloride) with ZnCl$_2$ as a catalyst to acquire 1 and 13 in high yield. Owing to the poor reactivity of longer chain alkanoyl chlorides (i.e., palmitoyl and stearoyl chlorides) towards tartaric acid in the aforementioned methodology, 12 and 3 were synthesized from dibenzyl L-tartrate (150). Compound 150 was first esterified with the respective fatty acid (i.e., palmitic or stearic acid) via carbodiimide coupling using EDCI and DMAP to acquire 12 and 3. The esterified derivative was subsequently selectively deprotected via hydrogenolysis using 10 wt % Pd/C to acquire 7 and 5.

Additional 2,3-bis(alkanoyl) tartaric acid derivatives were synthesized to investigate how structural modifications would influence both thermal stability and friction modifying properties. 2,3-Bis(dodecyl) tartaric acid (2) was synthesized to compare ether vs. ester (1) linkages, as ethers would function as more robust linkages owing to their poor leaving group ability. Thus, di-tert-butyl L-tartrate (152) was first synthesized following previous established methods (Uray, G.; Lindner, W., *Tetrahedron* 1988, 44, (14), 4357-4362), and subsequently alkylated using Williamson ether synthesis with 1-bromododecane in the presence of sodium hydride (NaH) to acquire di-t-butyl 2, 3-bis(dodecyloxyl) tartrate (153). Di-tert-butyl 2,3-bis(dodecyloxyl) tartrate was then selectively deprotected at the t-butyl ester with TFA to acquire 2 (Zhang, et al., *Biomaterials* 2016, 84, 230-40).

Literature has suggested improved thermal stability at higher temperatures of esters when comparing carboxylic acids vs. simple ester (i.e., Me-, Et-) derivatives (Moldovneanu, S. C., *Pyrolysis of Organic Molecules: Applications to Health and Environmental Issues.* 1st ed.; Elsevier: Oxford, U K, 2010; p 744). Two tartrate derivatives, diethyl (4) and di-tert-butyl 2,3-bis(stearoyl) tartrate (6), were also synthesized. The former, diethyl 2,3-bis (stearoyl) tartrate (4), was synthesized using an identical method to the 5 synthesis to elucidate the impact of free carboxylic acids vs. esters on thermal robustness. Since research has demonstrated t-butyl esters to be capable of undergoing β-ester pyrolysis and generating carboxylic acid derivatives, di-tertbutyl 2,3-bis(stearoyl) tartaric acid (6) was investigated as a 2,3-bis(alkanoyl) tartaric acid (5) delivery vehicle (Helgesen, M.; Krebs, F. C., *Macromolecules* 2010, 43, (3), 1253-1260; Peterson, et al., *Macromolecules* 2008, 41, 8986-8994).

Successful synthesis of 2,3-bis(alkanoyl) tartaric acids (1 and 13) and their precursors (12 and 3) in addition to ether (2), ethyl ester (4), and tertiary ester (6) derivatives was evident from $^1$H NMR spectroscopy. Using 3 as an example, successful product formation was evident by the downfield shift in the tartaric acid methine peak (5.76 ppm), the splitting of the methylene protons adjacent to stearic acid's carbonyl group (2.28 and 2.13 ppm), in addition to the introduction of fatty acid peaks. Subsequent 3 deprotection was corroborated by the absence of aromatic and benzyl protons in 5, in conjunction with accurate fatty acid: methine peak integration. Ester analogs (4 and 6) were corroborated by the appearance of fatty acid resonances in conjunction with the maintenance of ethyl (4) and tert-butyl (6) esters.

Coefficient of Friction and Thermal Robustness. The coefficients of friction of 2,3-bis(alkanoyl) tartaric acids and their derivatives were determined using HFRR with oscillating ball-on-disk under boundary conditions at 100 and 200° C. A series of 2,3-bis(alkanoyl) tartaric acids (1, 13, 7 and 5) was investigated, owing to their design incorporating two carboxylic acid moieties in close proximity. Research has suggested nearby carboxylic acids can improve friction modifier capabilities, specifically in more polar base stocks, due to enhanced polarity of the head group (Minami, I.; Mori, S., *Lubrication Science* 2007, 19, (2), 127-149). The enhanced polarity of the head group can help overcome solute-solvent interactions with polar base oils and assist in driving FMs towards metal surfaces. Multiple head groups increase the energetic gain of FM surface adhesion because of multiple favorable attachments to metal. Surface adsorption also increases entropy due to the transfer of multiple solvent molecules at the surface into the bulk solution. Furthermore, two adjacent longchain fatty acids may promote enhanced cohesive energy (van der Waals interactions) between chains when they are close in proximity and chemically conjugated compared to their respective fatty acid (i.e., lauric, myristic, palmitic, or stearic acid) alone.

TABLE 1

Averaged coefficient of friction (COF) for lauric acid, stearic acid, and compounds (1) to (7) and (13) at a concentration of 1 wt. % in SpectraSyn4 base oil (i.e., 4 cSt basestock PAO4). COF was reported as arithmetic average over the last 30 minutes of a two-hour run at 100 or 200° C., 400 g load, 60 Hz reciprocating frequency, and 1.0 mm stroke length.

| Compounds | Averaged COF (100° C.) | Averaged COF (200° C.) |
|---|---|---|
| Lauric acid | 0.067 | 0.085 |
| Stearic acid | 0.069 | 0.088 |
| 1 (T12) | 0.035 | 0.079 |
| 2 (T(12-O)) | 0.115 | 0.107 |
| 3 (DBT18) | 0.116 | 0.098 |
| 4 (DET18) | 0.096 | 0.102 |
| 5 (T18) | 0.025 | 0.080 |
| 6 (Di-t-butyl T18) | 0.091 | 0.068 |
| 7 | 0.036 | 0.100 |
| 13 | 0.040 | 0.096 |

Figure 3:
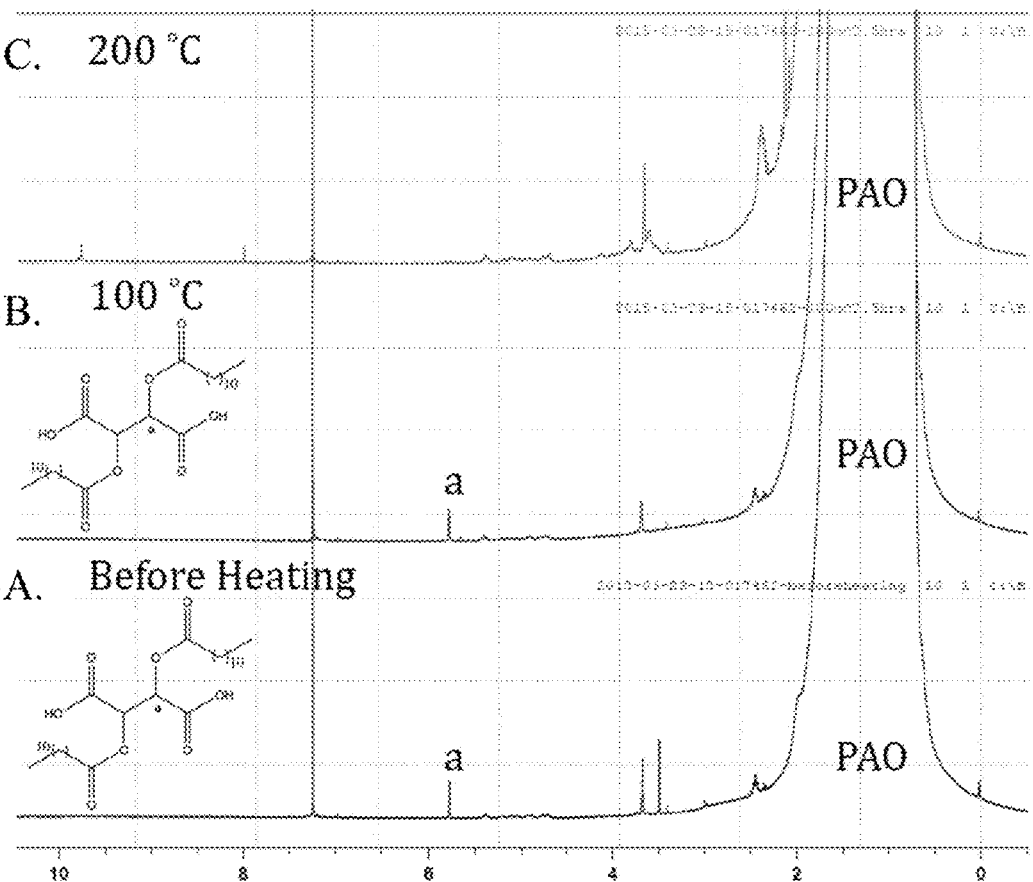
FIGS. 3A-C.

Initial studies focused on 1, a molecule previously synthesized, and its ether-modified derivative (2). At 100° C., 1 displayed superior performance, possessing an average COF of 0.035, approximately half that of the lauric acid (0.067, Table 1). Compound 2 unexpectedly experienced approximately a doubling in the COF (0.115, Table 1) compared to 1 at 100° C. and was appreciably higher than lauric acid itself. These results suggested that 2 either had poor adsorption onto the steel surface and/or weak cohesive energy between the hydrophobic aliphatic ether chains. When testing at 200° C., 2 exhibited similar results, whereas 1 initially reduced friction followed by a drastic increase in the COF to a level comparable to lauric acid. $^1$H NMR analysis following HFRR showed 1 to be stable at 100° C. (FIG. 3B), however, at 200° C. structural changes occurred, with 1's methine peak absent (FIG. 3C).

These results led to speculation that 1 could be undergoing decarboxylate elimination, releasing lauric acid in the process, as such decomposition reactions are common at elevated temperatures (Moldovneanu, S. C., *Pyrolysis of Organic Molecules: Applications to Health and Environmental Issues.* 1st ed.; Elsevier: Oxford, U K, 2010; p 744). To investigate this possibility, thermal stability tests at 200° C. were conducted on 1 and 2. The former compound exhibited weight loss >70% within the first ten minutes, whereas the latter lost ~20 wt. % within the same time frame. While thermal stability at 200° C. increased when transitioning from ester to ether arms, the onset of decomposition remained largely unchanged. Thus, it was speculated that the tartaric acid backbone with free carboxylic acids initiated the thermal decomposition pathway. Moreover, that the decomposition by-product generated with ether side chains, as oppose to ester side chains, was less volatile, accounting for these for the similar onset of decomposition but difference in mass loss under isothermal conditions.

Figure 4:
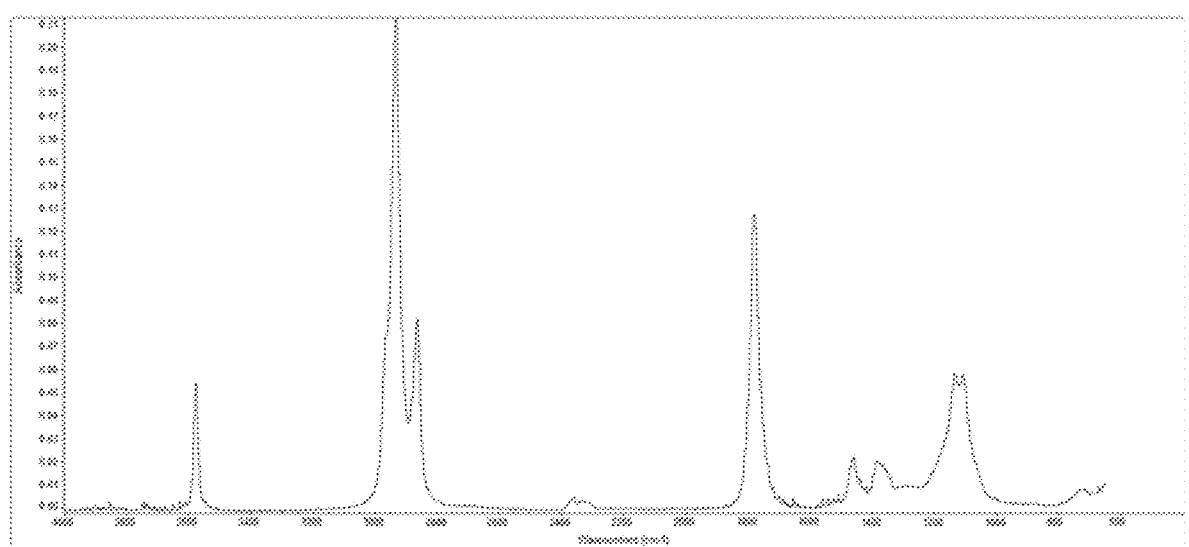
FIG. 4. Gas phase FTIR spectra of volatilized lauric acid displaying characteristic fatty acid aliphatic C—H stretches (2865 and 2933 $cm^{-1}$), carbonyl stretch (1778 $cm^{-1}$) and hydroxyl —O—H stretch (3576 $cm^{-1}$).

TGA-FTIR scans were used to investigate the decomposition pathway, by analyzing the evolved gas with increasing temperatures. 1 and 2 TGA-FTIR scans displayed $T_d$ values at 183 and 193° C., respectively. Moreover, both compounds possessed $T_d$ values above lauric acid, which begins to thermally decompose at 163° C. Further analysis of lauric acid revealed the evolved gas during TGA-FTIR scans to be volatilized lauric acid. Volatilized lauric acid FTIR spectra was dominated by symmetric and asymmetric $sp^3$ C—H stretching modes at 2933 and 2865 $cm^{-1}$, the C=O carbonyl stretching band at 1778 $cm^{-1}$, in addition to —OH stretching at 3576 $cm^{-1}$ (FIG. 4). These features are a signature profile of volatilized fatty acids and consistent with TGA-FTIR spectra of similar molecules (Rudolph, et al., *Colloids and Surfaces A: Physicochemical and Engineering Aspects* 2012, 397, 16-23; Zhang, et al., *Metallurgical and Materials Transactions A* 2009, 41, (2), 532-541). This finding was promising as one of the by-products from 1 decarboxylative elimination was anticipated to be lauric acid, which could be confirmed by TGA-FTIR spectroscopy. More importantly, should 1 release lauric acid at elevated temperatures, this compound would offer a two-pronged system in which both the parent compound and decomposition product could effectively lower friction.

Figure 5A:
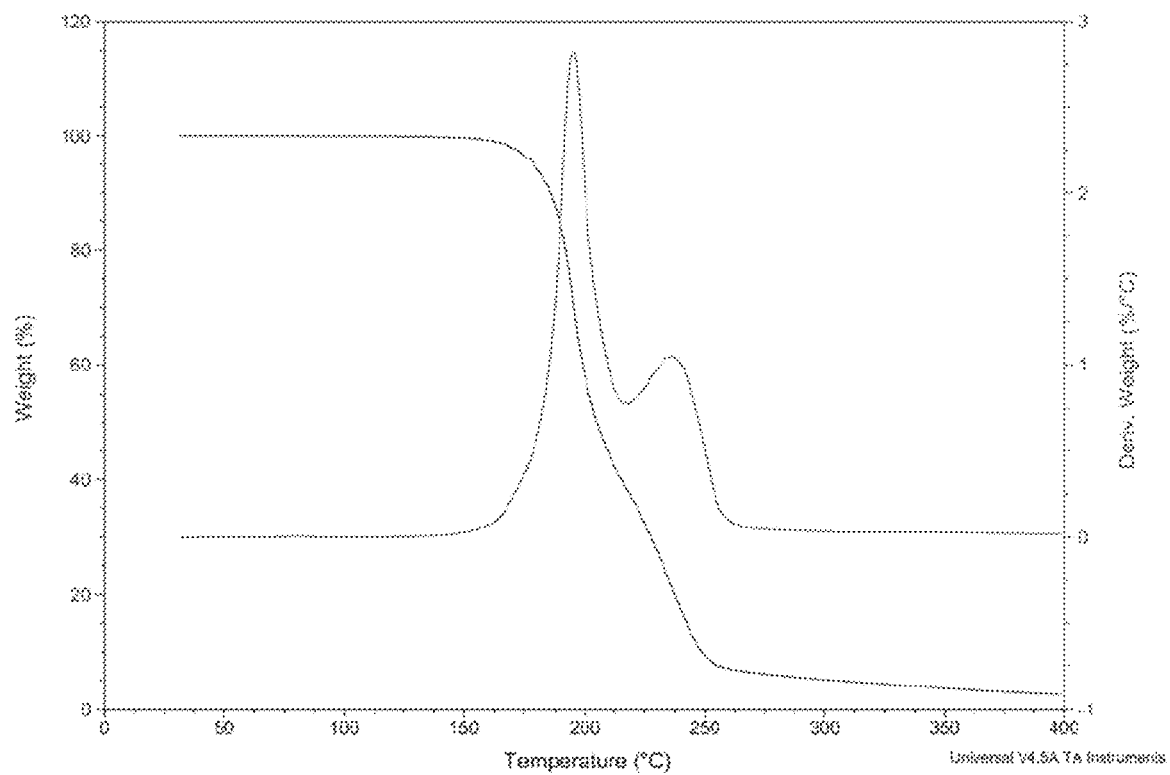
FIGS. 5A-B.
Figure 5B:
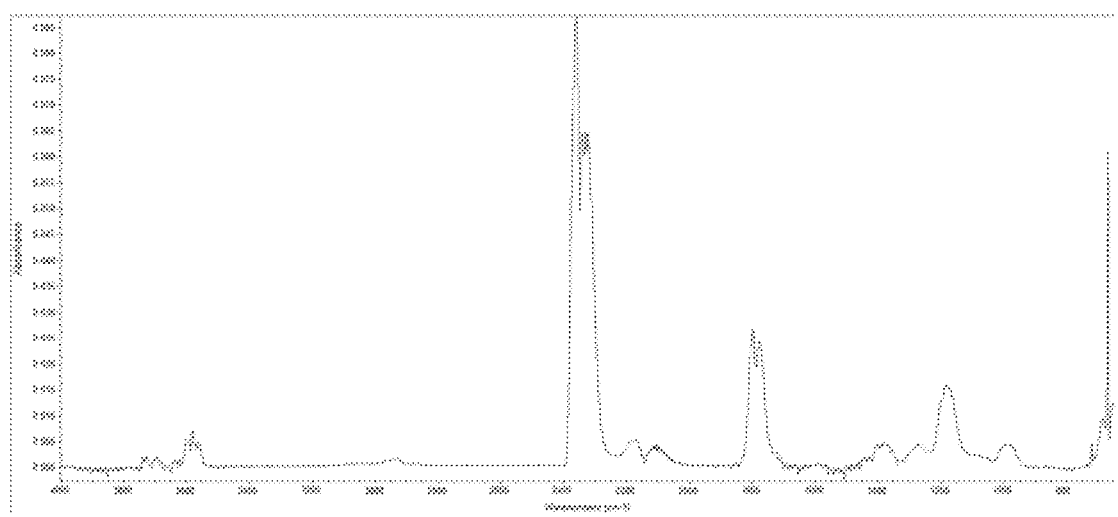
Figure 6:
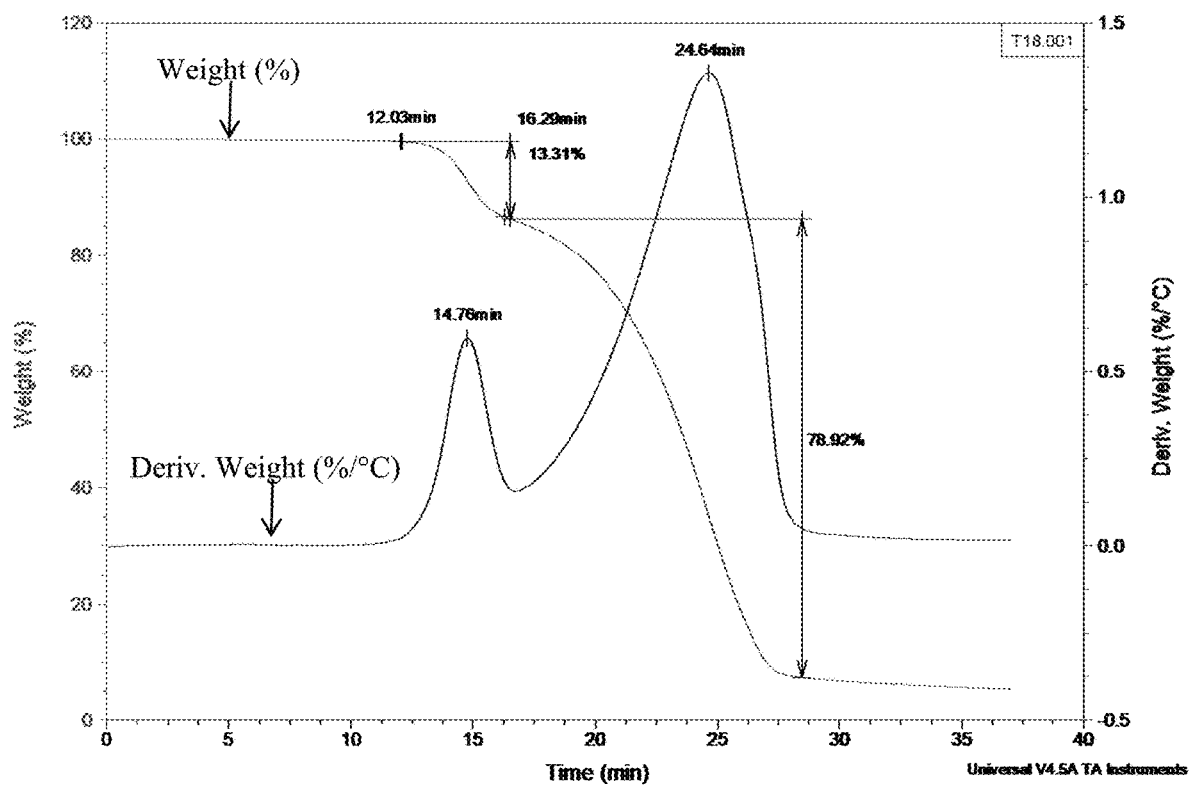
FIG. 6. Thermogram of 5 showing two-step weight loss, the first loss (13 min onset) correlates to tartaric acid backbone degradation (~13 wt. %), whereas the second loss (17 min onset) indicates stearic acid volatilization.

While 1's TGA-FTIR scan possessed a two-step mass loss (FIG. 5A), neither correlated to decarboxylative elimination (i.e., weight loss was greater than that associated with carboxylic acid functionalities ~28 wt. %). The FTIR spectra displayed signature asymmetric stretching and degenerative bending $CO_2$ peaks at 2356 and 666 $cm^{-1}$, correlating to the expected by-product from decarboxylation. 1's FTIR spectra also contained multiple carbonyl stretches (1777 and 1797 $cm^{-1}$), broader hydroxyl stretches (3581 $cm^{-1}$), and a prominent C—O stretch (1183 $cm^{-1}$) indicating a much more complex degradation pathway than initially anticipated (FIG. 5B). While it possessed carbonyl and hydroxyl stretches, suggesting possible formation of a carboxylic acid, it interestingly lacked aliphatic C—H stretching absorbances. Although the mechanism of thermal decomposition was inconclusive, 1 demonstrated promising friction modifying capabilities resulting in the development of additional derivatives to further explore the decomposition pathway and optimize the FM properties of the system.

To determine whether increasing the carbon chain length of the arms in 2,3-bis(alkanoyl) tartaric acid would further improve friction modifier capabilities, dicarboxylic acid derivatives with myristic (13), palmitic (7), and stearic acid (5) were evaluated using HFRR. Whereas 13 and 7 were found to possess a similar COF to 1 (0.038±0.002, Table 1) at 100° C., 5 displayed a considerably lower value (0.025, Table 1) than all other 2,3-bis(alkanoyl) tartaric acids and approximately one-third of stearic acid. The dicarboxylic acid moiety of 5 enabled enhanced surface activity relative to mono-carboxylic acids (i.e., stearic acid), while the longer aliphatic chains of the compound facilitated increased cohesive energy between hydrocarbon chains. Similar to 1, all analogues experienced significant increase in COF at 200° C., presumably due to decomposition.

Figures 7A, 7B:
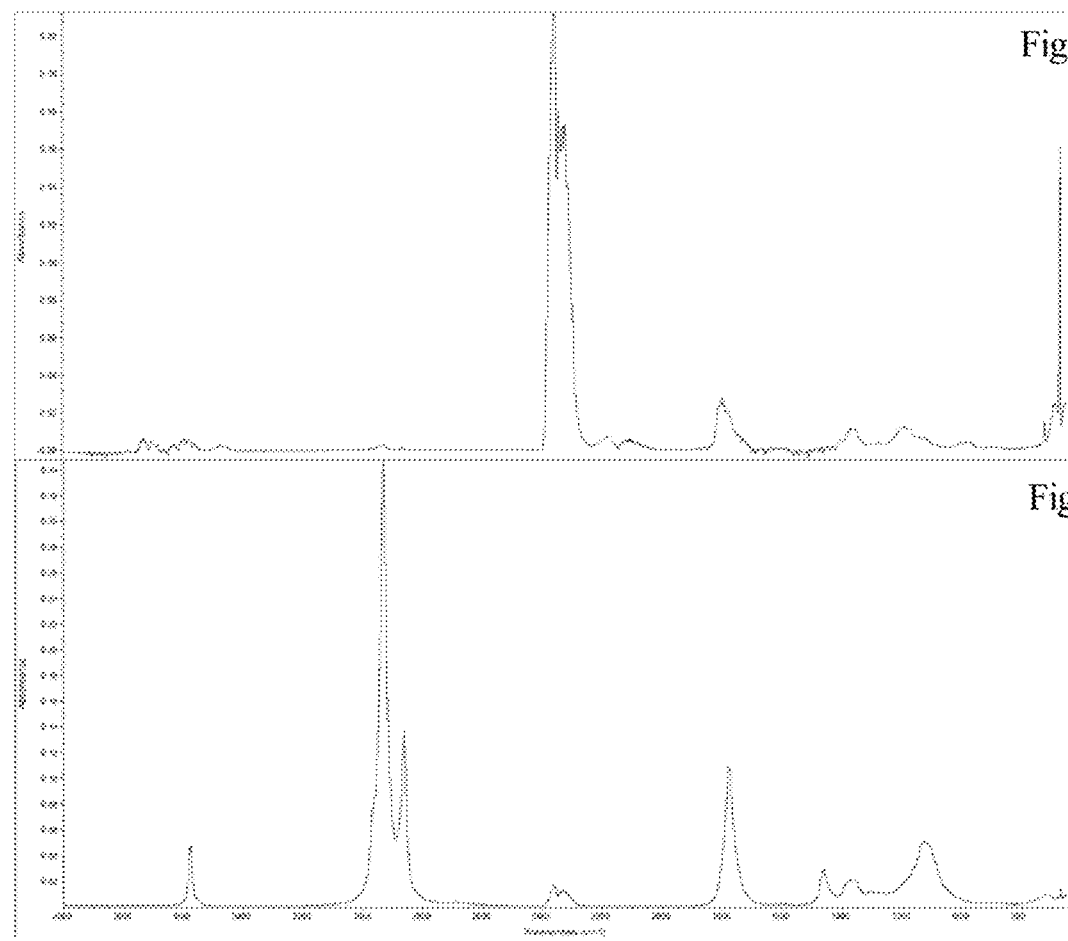
FIGS. 7A-C. The gas phase IR spectra of two phases of thermal decomposition of compound (5) and pure stearic acid volatilization as a reference is shown.
Figure 7C:
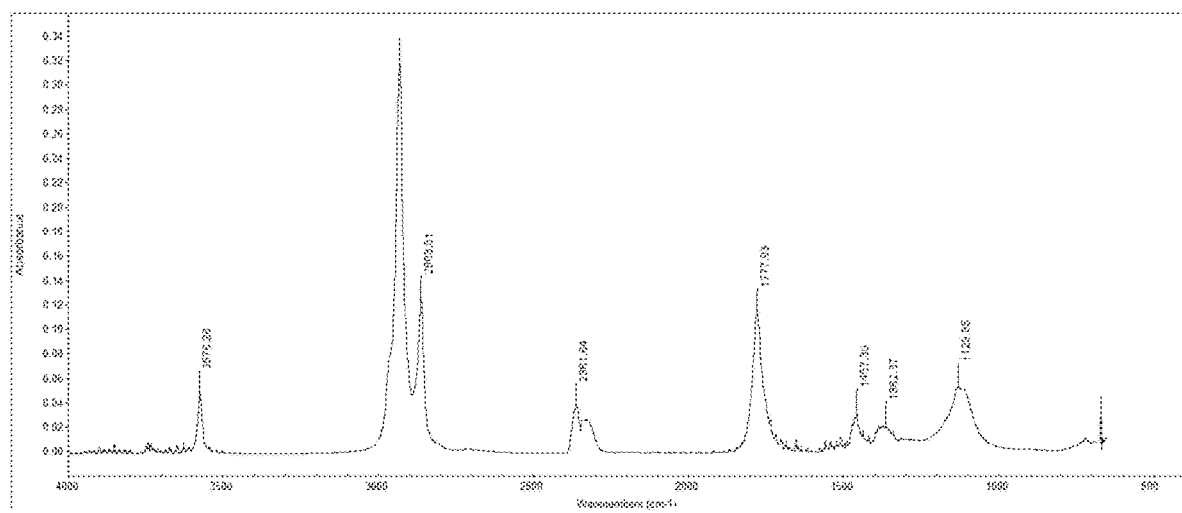

Consistent with 1 and 2, compounds 13, 7 and 5 all exhibited $T_d$ values below 200° C., 185±10° C., suggesting similar degradation pathways. Whereas, 13 and 7 displayed near-identical TGA-FTIR thermograms and gas phase spectra, 5 possessed a distinct, two-step decomposition pathway (FIG. 7). In the first decomposition step, an initial weight loss of ~13% is evident, correlating to the mass of the tartaric acid backbone. This loss is followed by a prolonged weight loss, accounting for ~80 wt. %, with residual mass remaining as organic char. As expected, the FTIR spectra of the first decomposition step contained a significant amount of $CO_2$, evident by the large absorbances at 2354 and 664 $cm^{-1}$ (FIG. 7A). Moreover, peaks at 3850, 1797, 1776, 1386, 1182, and 999 $cm^{-1}$ were also present. These absorbances are consistent with the initial decomposition step of each 2,3-bis(alkanoyl) tartaric acid (1, 13, 7 and 5), corroborating a similar decomposition pathway. Following the initial decomposition cascade, volatilized stearic acid was evident (FIG. 7B) with asymmetric and symmetric C—H $sp^3$ hybridized stretches at 2932 and 2838 $cm^{-1}$, the C=O carbonyl stretch at 1778 $cm^{-1}$, and —O—H gas phase stretch at 3576 $cm^{-1}$ (Zhang, et al., *Metallurgical and Materials Transactions A* 2009, 41, (2), 532-541). These findings coupled with the COF above 5's $T_d$, demonstrate that 5 not only possesses friction modifying capabilities, but also decomposes to release stearic acid, an established FM. Consequently, 5 functions as both a potent FM and a delivery vehicle for stearic acid, offering a means to replenish in situ FM quantities.

The difference in decomposition of 5 when compared to shorter chain fatty acid derivatives (1, 13 and 7) is likely due to the higher volatilization temperature of stearic acid. For example, lauric acid volatilizes at 163° C., whereas stearic acid volatilizes at 208° C. This finding coupled with the similar COF results between 5 and stearic acid at 200° C. confirms that 5 does release stearic acid. The consistent $T_d$ onset of (1, 13, 7 and 5), regardless of the conjugated fatty acids, suggests that the free carboxylic acid of the tartaric acid backbone is likely the driving force for thermal degradation. Given the enhanced potency of 5 relative to its decomposition product (i.e., stearic acid), thermal stability improvement was sought.

Figure 8A:
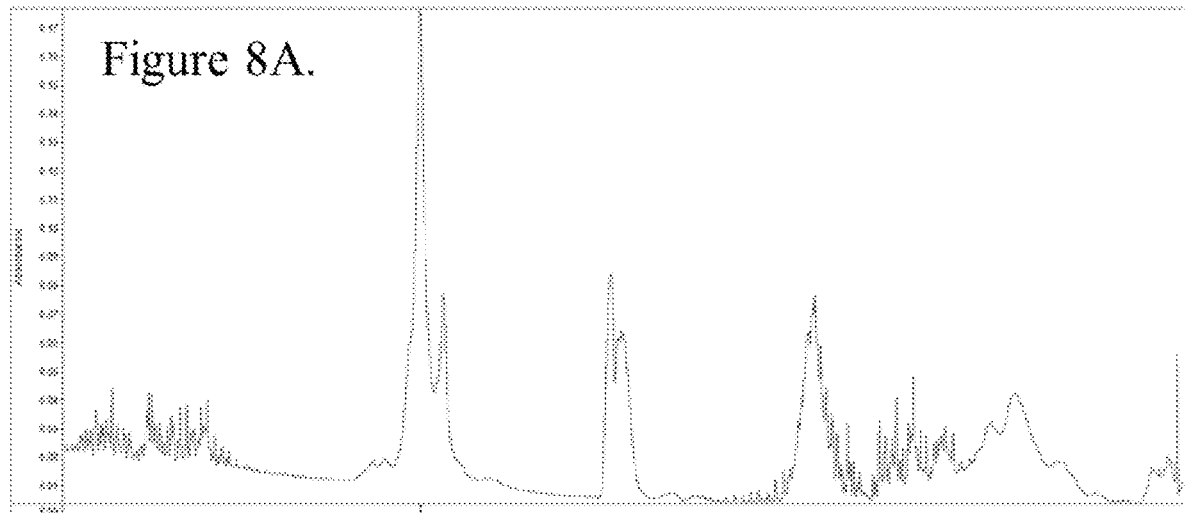
FIGS. 8A-B.
Figure 8B:
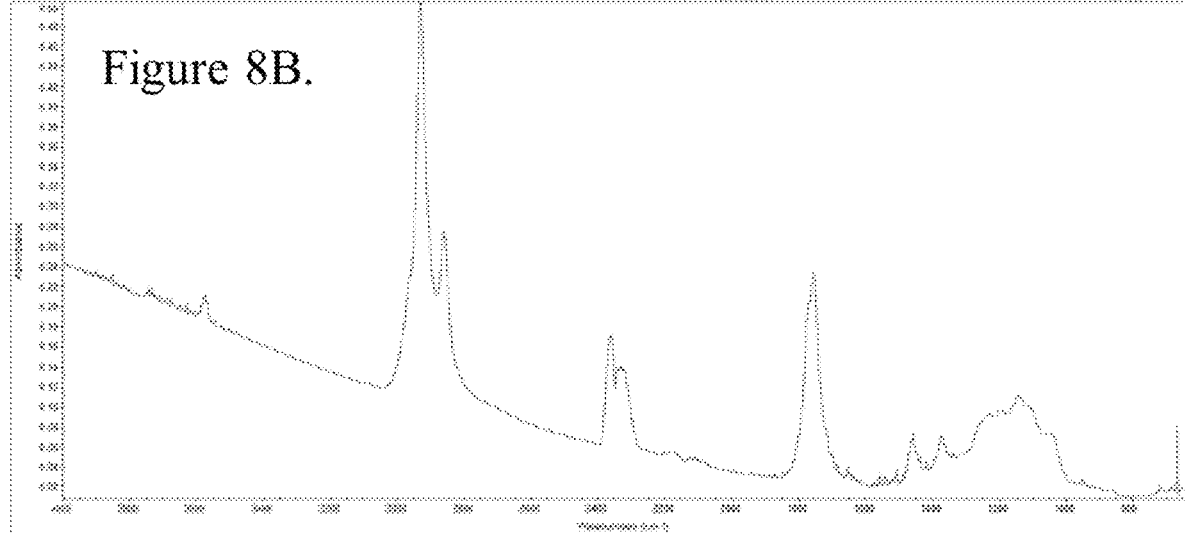

To further test the thermal decomposition hypothesis and enhance small molecule additive thermal robustness, diesters of 5, specifically 3 and 4, were analyzed. 5 and diester derivative $T_d$'s decreased in the order of 4>3>5 (227, 215, and 183° C., respectively) with thermal stability following a similar trend. These findings corroborated that the presence of carboxylic acids in the tartrate backbone were responsible for the initial thermal decomposition of compound 5 and its shorter aliphatic-linked derivatives (1, 13 and 7). Moreover, TGA-FTIR analysis of 3 and 4 displayed broad, mono-modal weight losses with distinctly different evolved gases (FIG. 8). While diester derivatives enhanced thermal stability relative to 5, the COF was considerably higher at 100° C. and lacked improvement at 200° C. (Table 1). This effect is may be due to decreased adsorption to the surface owing to the less polar head group of the ester vs. carboxylic acid (Jahanmir, S.; Beltzer, M., *Journal Of Tribology* 1986, 108, 109-116; Jahanmir, S.; Beltzer, M., et al., *Tribology Transactions* 1986, 29, 423-430).

More importantly, by esterifying the carboxylic acid head groups it altered the degradation pathway, as stearic acid release was not evident. Thus, it became apparent that dicarboxylic acid head groups were necessary for both superior COF properties and releasing desired decomposition product stearic acid. It was hypothesized that the esterification of the carboxylic acid end groups transitioned the initial thermal decomposition pathway from that of decarboxylative elimination, which would release stearic acid. Moreover, that the benzyl (3) and ethyl (4) esters were too thermally robust to undergo β-ester pyrolysis and subsequently generate carboxylic acid end groups. Thus, it is likely that 3 and 4 thermally decomposed via random bond scission, accounting for the worse COF at 200° C. when compared to 5, as stearic acid would not be released.

Controlled FM Release. Owing to the superior COF of 5, additional modifications were explored to both improve oil solubility and develop a system capable of delivering FMs in a sustained manner. Previous research indicated that tertiary esters in low bandgap polymers were utilized to improve solubility, and were subsequently cleaved at higher temperatures (Helgesen, M.; Krebs, F. C., *Macromolecules* 2010, 43, (3), 1253-1260; Peterson, et al., *Macromolecules* 2008, 41, 8986-8994). Therefore, it was hypothesized that di-t-butyl derivatives of 5 (6) could be used to enhance its oil solubility and release the active in a sustained manner when exposed to higher temperature (e.g., an engine piston).

Figure 9A:
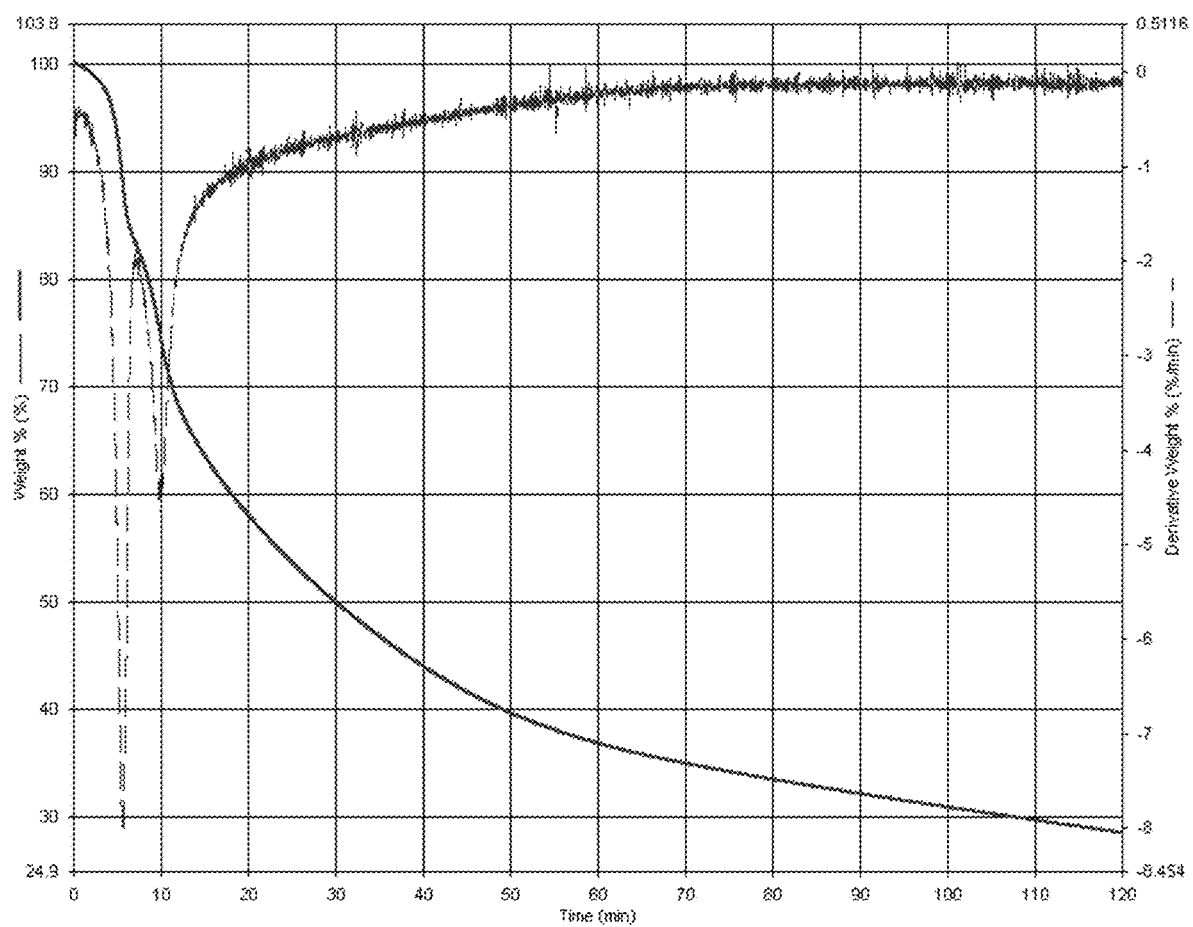
FIGS. 9A-B. Thermal stability study of 6 showing three-step weight loss with initial loss corresponding to the weight of the t-butyl protecting groups (~15%) and second step correlating to the tartaric acid backbone (~11%), followed by stearic acid volatilization.
Figure 9B:
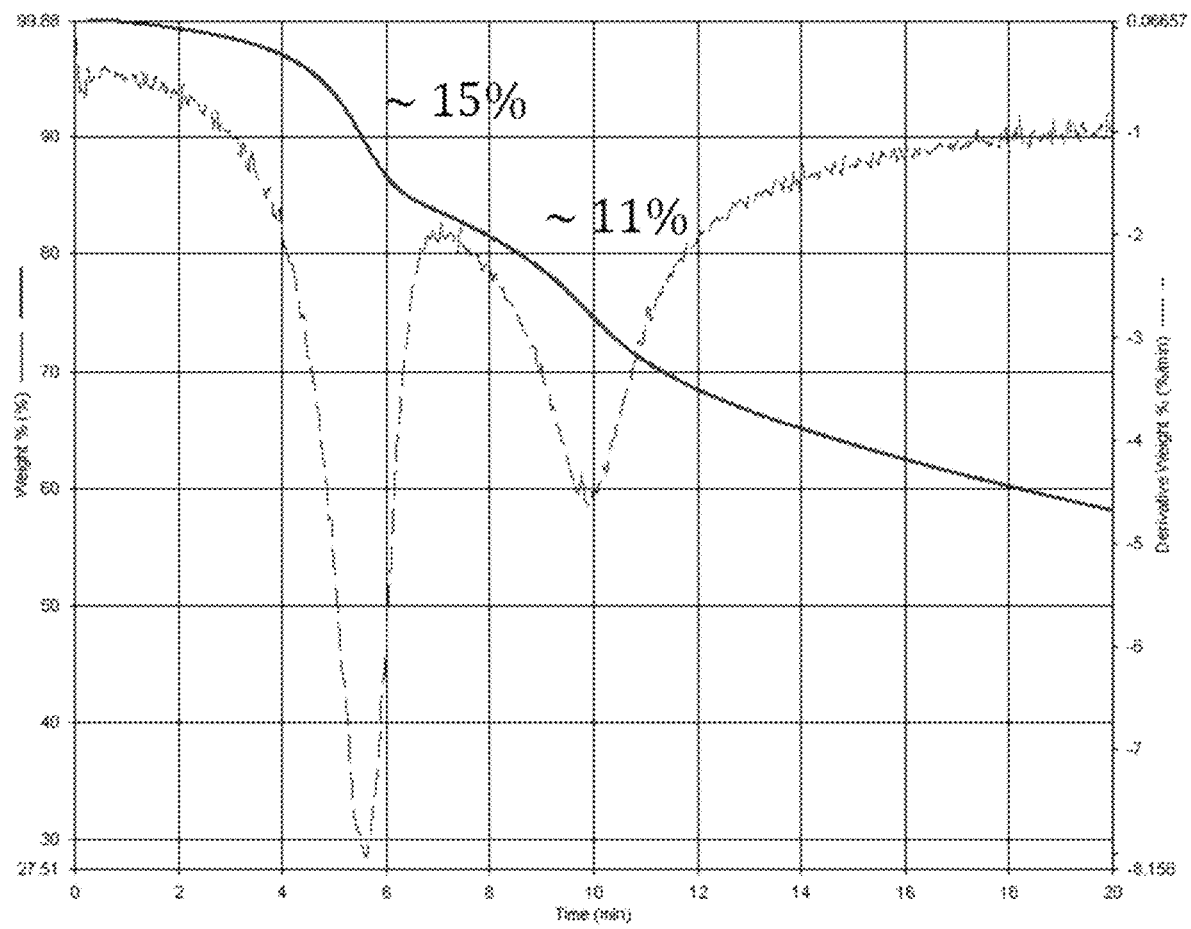
Figures 10A, 10B, 10C:
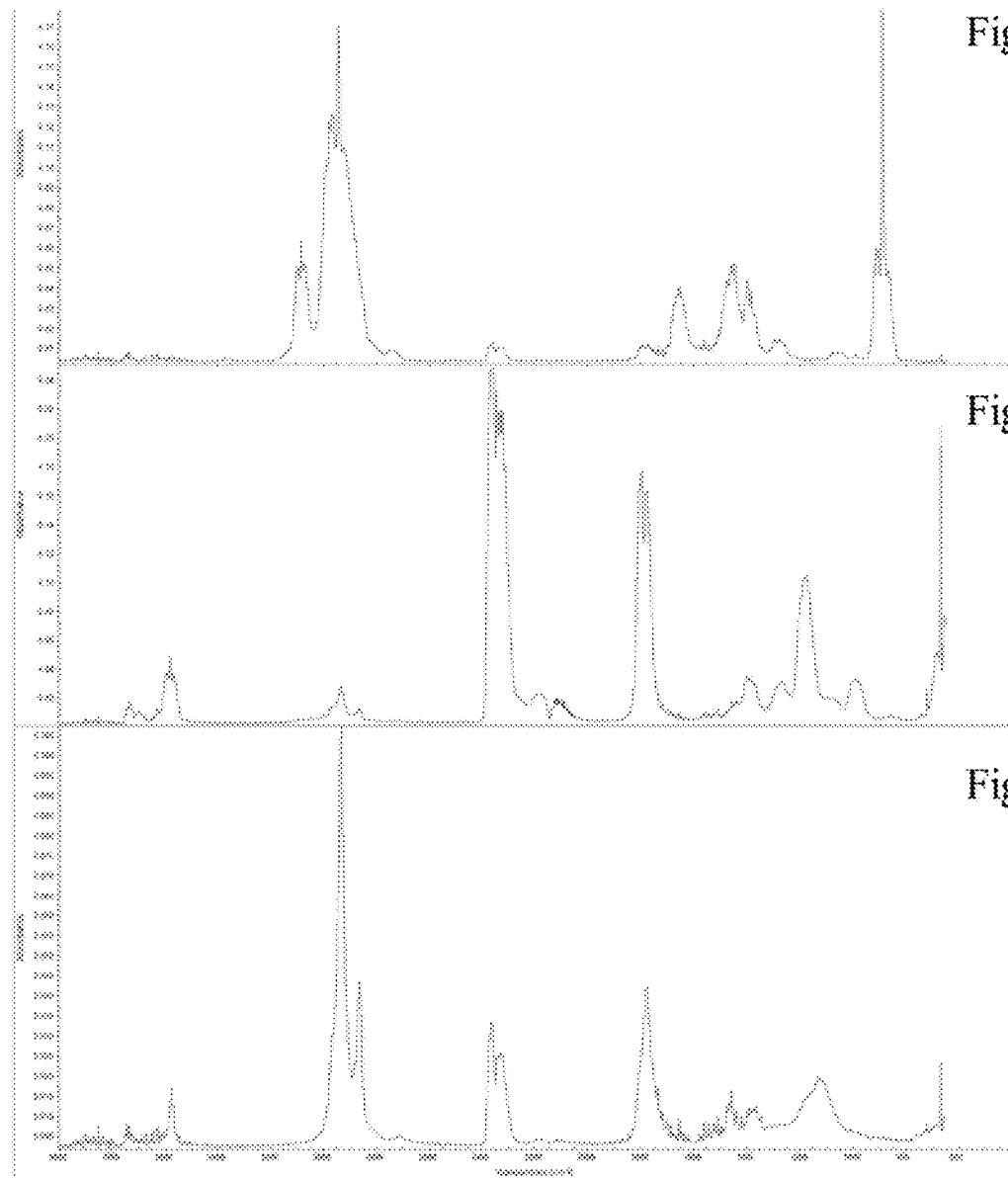
FIGS. 10A-C. The gas phase IR spectra of three phases of thermal decomposition of compound (6) is shown.

Initial thermal stability screening revealed decomposition of 6 was occurring in three distinct steps (FIG. 9B), ~15% weight loss in the first step, followed by ~11 wt. % in the second step, and lastly, sustained weight loss resulting in residual charring. These results were promising as the weight losses in the first and second steps are closely associated with β-ester pyrolysis of 6, releasing isobutylene, followed by subsequent tartaric acid backbone degradation. Further analysis using TGA-FTIR measurements confirmed that the degradation product isobutylene was generated in the initial sequence, as evident by the asymmetric $CH_2$ stretch at 3085 $cm^{-1}$ and $CH_3$ symmetric and asymmetric stretches at 2965 and 2944 $cm^{-1}$ (FIG. 10A). Moreover, the C=C stretch at 1653 $cm^{-1}$, $sp^3$ hybridized C—H stretch at 1395 $cm^{-1}$, and $CH_2$ wag at 888 $cm^{-1}$ are consistent with free isobutylene spectra (Storey, et al., *Macromolecules* 1998, 31, 1523-1526; Dogu, et al., *Ind. Eng. Chem. Res.* 2001, 40, 5044-5051). This finding suggested that 6 was decomposing in a controlled manner to release 5. Following β-ester pyrolysis and ensuing isobutylene release, distinct peaks corresponding to $CO_2$ are apparent, in addition the carbonyl (1797 and 1776 $cm^{-1}$) and hydroxyl stretches (3850 $cm^{-1}$) (FIG. 10B). These latter peaks are consistent with the initial decomposition cascade of 5, again confirming β-ester pyrolysis, and subsequent 5 release. The final degradation sequence is the volatilization of stearic acid, as evident by the near-identical spectra to that of free stearic acid (FIG. 10C). These analyses corroborated that 6 delivers 5, which at elevated temperatures releases stearic acid.

Supporting our hypothesis, HFRR data showed improved COF values with increasing temperature. Initially, at 100° C. friction-modifying capabilities similar to diester 3 and 4 occurred, whereas at 200° C., the COF decreased to a value similar to that of 5 under similar conditions. As demonstrated by TGA-FTIR and thermal stability studies, 6 decomposes around 200° C. to release 5, which is unstable at higher temperatures and exhibits a COF similar to stearic acid. The impact of 6 under engine mimicking conditions was then investigated.

Figure 11:
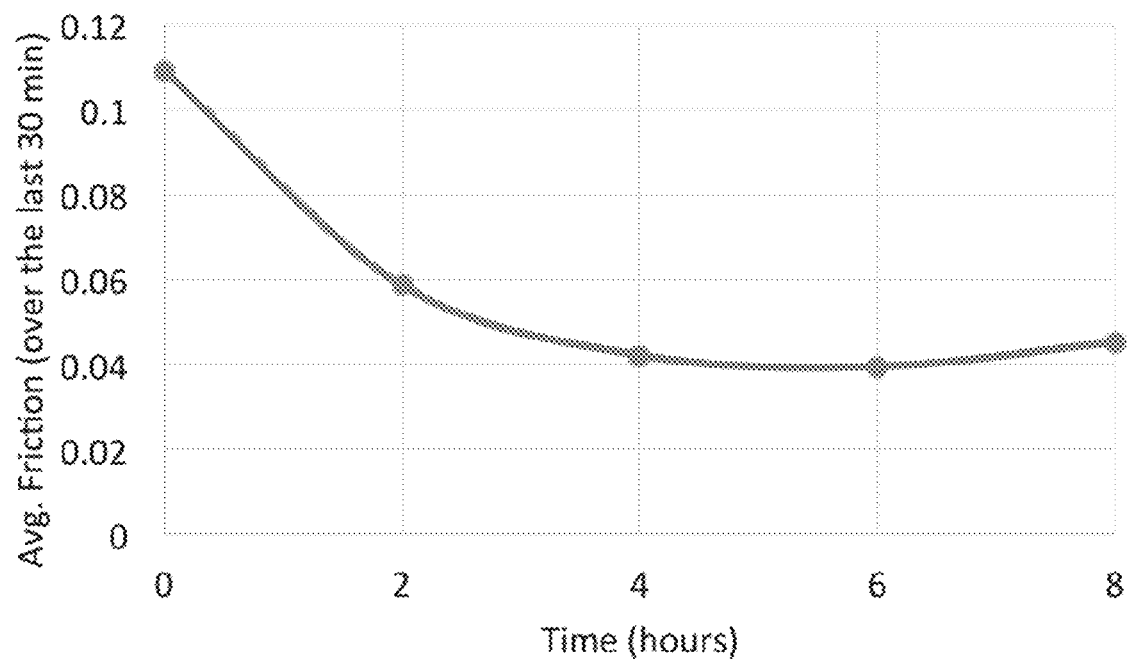
FIG. 11. HFRR results of aliquots removed from CRU at 2, 4, 6, and 8 h. Study reveals that upon exposure to high temperature block, 6 releases 5 in a controlled and sustained manner. Moreover, 5 slightly loses activity over time, decomposing into stearic acid.
Figure 12A:
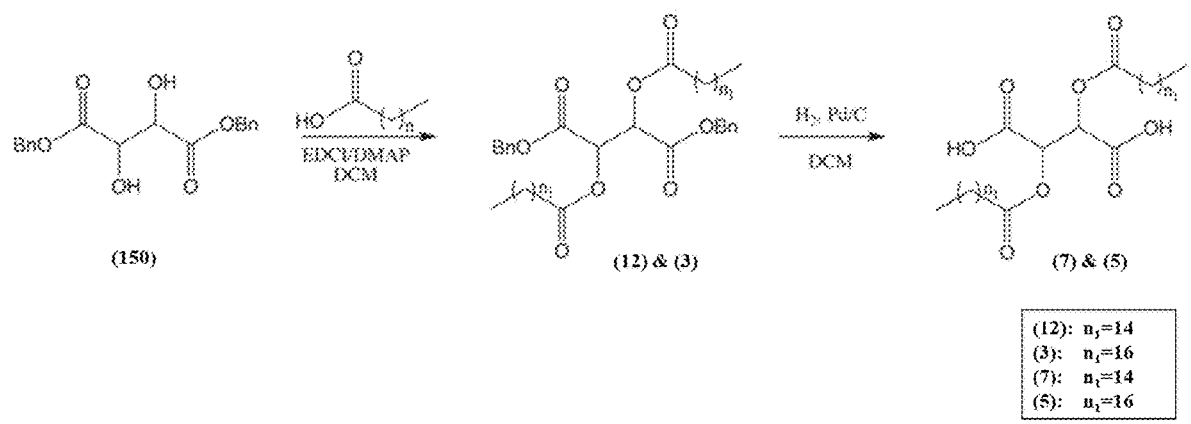
FIGS. 12A-D. Synthetic schemes of 2,3-bis(alkanoyl) tartaric acids derivatives (7 and 5) via two steps (FIG. 12A). 2,3-bis(alkanoyl) tartaric acids derivatives (1 and 13) via direct conjugation (FIG. 12B). 2,3-bis(dodecyl) tartaric acid (2), (FIG. 12C) and 2,3-bis(alkanoyl) tartrate derivatives (4 and 6) (FIG. 12D).
Figure 12B:
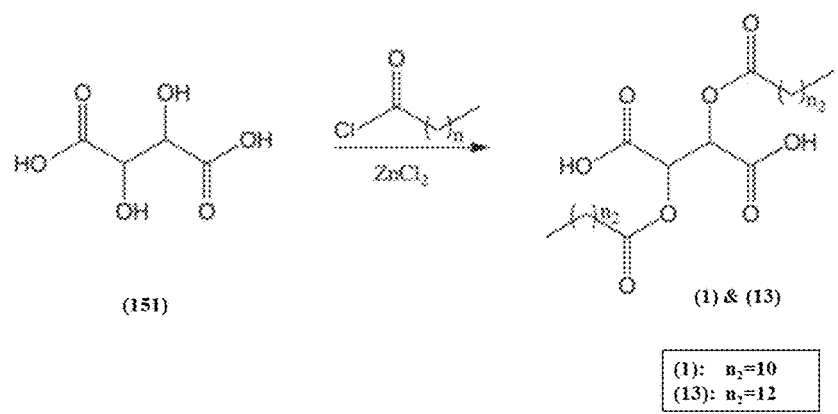
Figure 12C:
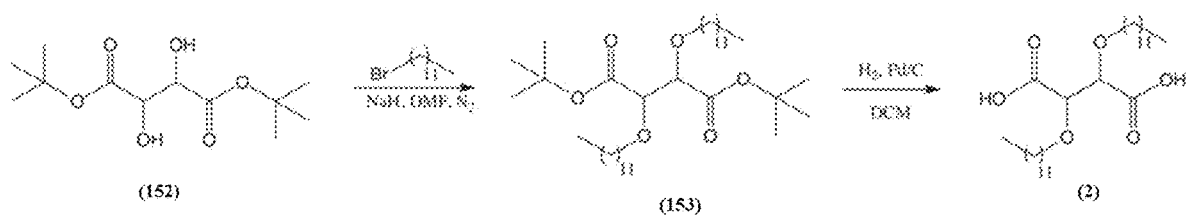
Figure 12D:
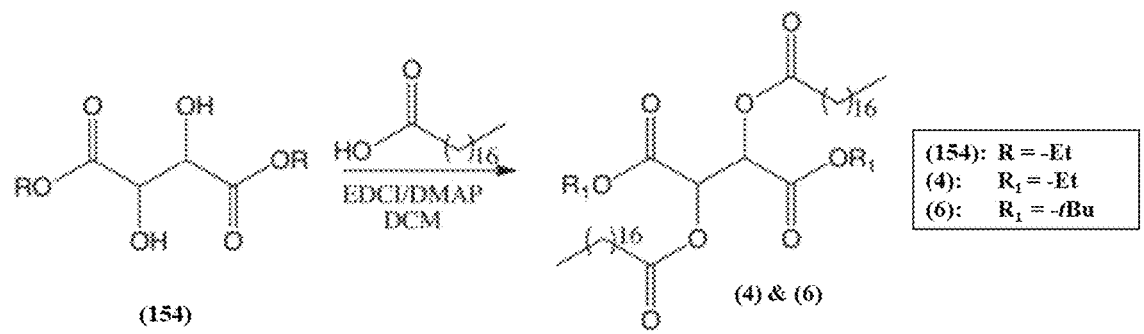

Under engine mimicking conditions, the temperature and pressure are not constant, as is the case in HFRR, and 6 would be exposed to a temperature capable of facilitating β-ester pyrolysis for a shorter period of time. To investigate this aspect, 6 was exposed to a home-built Controlled Release Unit (CRU), in which the bulk oil with additive was held at 130° C. and briefly exposed to a block heater, mimicking an engine piston, at 215° C. It was expected that the initial COF would be comparable to that of 6 prior to decomposition, and later time-points to show sustained COF values similar to that of 5 and stearic acid. As expected, the COF was 0.109 at time zero and decreased over the first four hours to a COF of 0.042, indicating 5 release (FIG. 11). After four hours the COF became relatively constant at 0.040±0.005. It is likely that 6 is undergoing β-ester pyrolysis over the first four hours, generating 5, faster than 5 is decomposing into stearic acid. As the bulk temperature of the oil (130° C.) is well below the $T_d$ of 5 (183° C.) the active is stable and effectively lowers the friction in engine mimicking conditions. Over time, it is possible that more 5 will be exposed to the high temperature block (215° C.), facilitating 5 decomposition into stearic acid.

In summary, a series of fatty acid-containing diacids based on a tartaric acid backbone, in addition to ether and ester analogues, were successfully synthesized and fully characterized. Ether side chains and diester head groups were found to drastically increase the COF, with the former having minimal impact on thermal stability and the latter greatly enhancing it. 5 was identified as a lead compound, effectively reducing friction and releasing stearic acid upon decomposition. Tertiary ester derivatives of 5 (6) were then investigated as a controlled release system to overcome both solubility issues and replenish FMs in solution. TGA-FTIR data demonstrated that 6 underwent a β-ester pyrolysis to release 5, which at elevated temperature degraded further to release stearic acid, allowing for the sustained release of multiple FMs. HFRR corroborated these findings, showing improved COF at higher temperatures. Additionally, CRU analyses, mimicking engine conditions, showed sustained friction reduction over the course of the study, indicating promise for this technology in improving engine efficiency. This novel delivery method, coupled with the potent friction modification of the molecules described here, offer a means to overcome traditional FM consumption.

All publications cited herein are incorporated herein by reference. While in this application certain embodiments of invention have been described, and many details have been set forth for purposes of illustration, it will be apparent to those skilled in the art that certain of the details described herein may be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not pose a limitation on the scope of the invention unless otherwise specifically recited in the claims. No language in the specification should be construed as indicating that any non-claimed element as essential to the practice of the invention.

What is claimed is:

1. A lubricating oil composition comprising a lubricating oil base stock and a compound of formula (I):

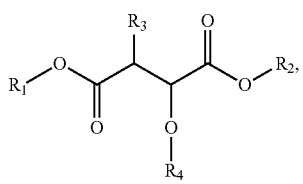

(I)

wherein, $R_1$ and $R_2$ are each independently tertiary ($C_4$-$C_{12}$)alkyl, benzyl or phenethyl; $R_3$ is $OR^a$, wherein $R^a$ is ($C_1$-$C_{20}$)alkyl, ($C_1$-$C_{20}$)alkanoyl, ($C_2$-$C_{20}$)alkenyl or ($C_3$-$C_{20}$)alkenoyl; and $R_4$ is ($C_1$-$C_{20}$)alkyl, ($C_1$-$C_{20}$) alkanoyl, ($C_2$-$C_{20}$)alkenyl or ($C_3$-$C_{20}$)alkenoyl; or a salt thereof.

2. A lubricating oil composition comprising a lubricating oil base stock and a compound of formula (I):

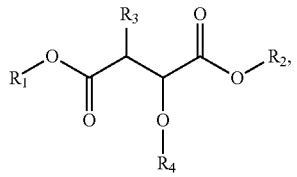

(I)

wherein, $R_1$ and $R_2$ are each H or wherein $R_1$ and $R_2$ are each tert-butyl; $R_3$ is H or $OR^a$, wherein $R^a$ is ($C_1$-$C_{20}$) alkyl, ($C_1$-$C_{20}$)alkanoyl, ($C_2$-$C_{20}$)alkenyl or ($C_3$-$C_{20}$) alkenoyl; and $R_4$ is ($C_1$-$C_{20}$)alkyl, ($C_1$-$C_{20}$)alkanoyl, ($C_2$-$C_{20}$)alkenyl or ($C_3$-$C_{20}$)alkenoyl;
or a salt thereof.

3. The lubricating oil composition of claim 1, wherein $R_3$ is $OR^a$, wherein $R^a$ is ($C_1$-$C_{20}$)alkyl.

4. The lubricating oil composition of claim 1, wherein $R_3$ is $OR^a$, wherein $R^a$ is ($C_1$-$C_{20}$)alkanoyl.

5. A lubricating oil composition comprising a lubricating oil base stock and a compound of formula (I):

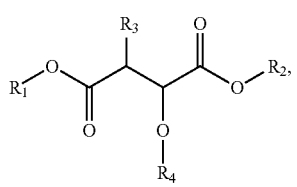

(I)

wherein, $R_1$ and $R_2$ are each independently H, ($C_1$-$C_{12}$) alkyl, benzyl or phenethyl; $R_3$ is H or $OR^a$, wherein $R^a$ is ($C_1$-$C_{20}$)alkyl, ($C_1$-$C_{20}$)alkanoyl, ($C_2$-$C_{20}$)alkenyl or ($C_3$-$C_{20}$)alkenoyl; $R_4$ is ($C_1$-$C_{20}$)alkyl; or a salt thereof.

6. The lubricating oil composition of claim 1, wherein $R_4$ is ($C_1$-$C_{20}$)alkanoyl.

7. A lubricating oil composition comprising, a lubricating oil base stock and a compound of formula (I) selected from the group consisting of:

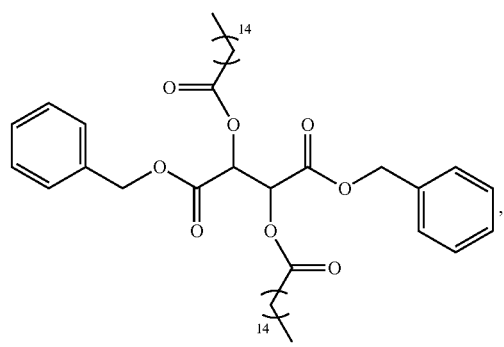

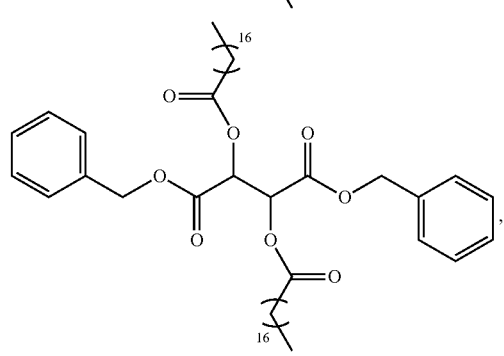

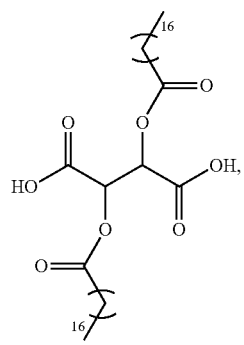

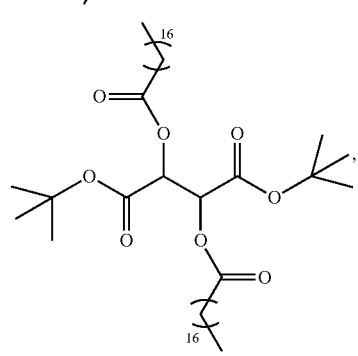

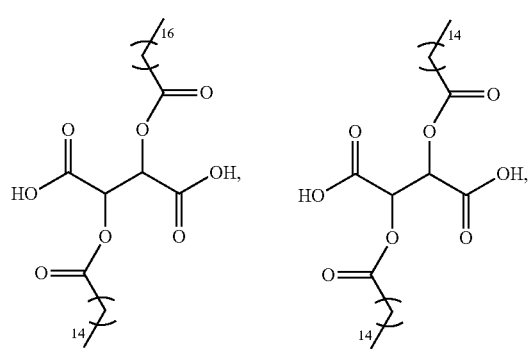

-continued

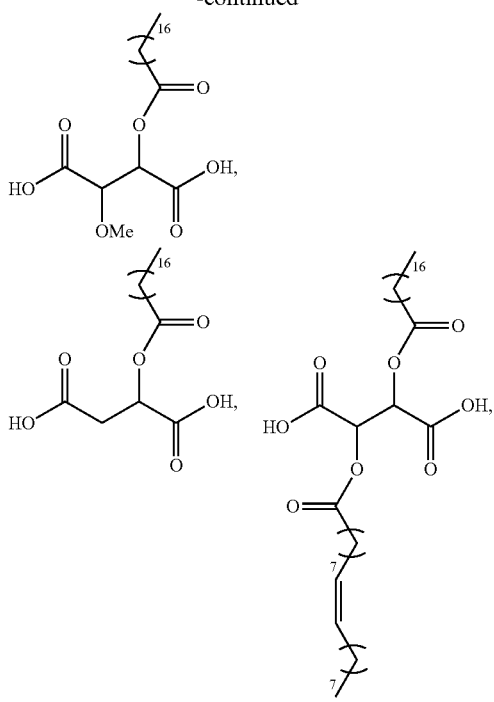

and

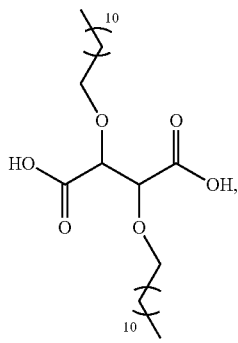

or a salt thereof.

8. The lubricating oil composition of claim 2, wherein the compound of formula (I) is:

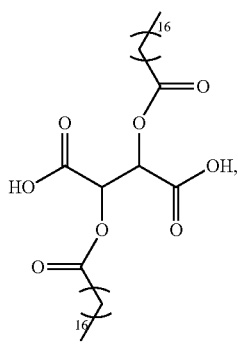

or a salt thereof.

9. The lubricating oil composition of claim 2, wherein the compound of formula (I) is:

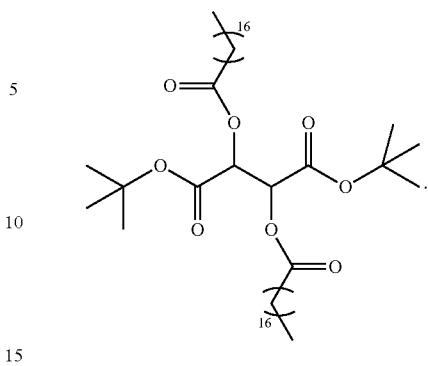

10. The lubricating oil composition of claim 1, wherein the lubricating oil base stock comprises a Group I, Group II, Group III, Group IV or Group V base oil.

11. The lubricating oil composition of claim 1, comprising a mixture of two or more compounds of formula (I), or salts thereof, wherein the two or more compounds of formula (I), or salts thereof, have different thermal release temperatures.

12. The lubricating oil composition of claim 1, further comprising one or more lubricating oil performance additives selected from the group consisting of an anti-wear additive, viscosity modifier, antioxidant, detergent, dispersant, pour point depressant, corrosion inhibitor, metal deactivator, seal compatibility additive, anti-foam agent, other friction modifier and anti-rust additive/inhibitor.

13. A compound of formula (I):

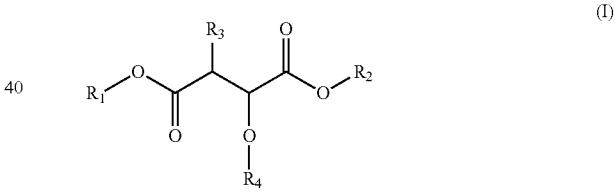

wherein, $R_1$ and $R_2$ are each independently tertiary ($C_4$-$C_{12}$) alkyl; $R_3$ is $OR^a$, wherein $R^a$ is ($C_3$-$C_{20}$)alkanoyl or ($C_3$-$C_{20}$)alkenoyl; and $R_4$ is ($C_1$-$C_{20}$)alkanoyl or ($C_3$-$C_{20}$)alkenoyl; or a salt thereof.

14. The compound of claim 13, which is a compound of formula (Ib):

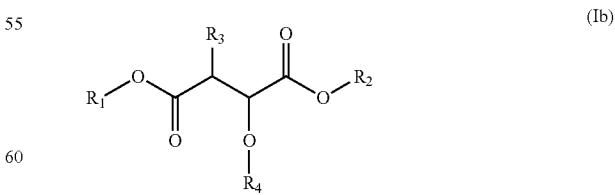

wherein, $R_1$ and $R_2$ are each independently tertiary ($C_4$-$C_{12}$) alkyl; $R_3$ is $OR^a$, wherein $R^a$ is ($C_3$-$C_8$)alkanoyl or ($C_3$-$C_8$) alkenoyl; and $R_4$ is ($C_1$-$C_{20}$)alkanoyl, or ($C_3$-$C_{20}$)alkenoyl; or a salt thereof.

15. A compound of formula (Ic):

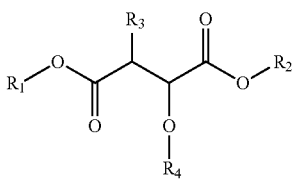

wherein, $R_1$ and $R_2$ are each independently tertiary $(C_4$-$C_{12})$ alkyl, $R_3$ is $OR^a$, wherein $R^a$ is $(C_1$-$C_{20})$alkanoyl or $(C_3$-$C_{20})$alkenoyl; and $R_4$ is $(C_{14}$-$C_{20})$alkanoyl or $(C_{14}$-$C_{20})$alkenoyl; or a salt thereof.

16. The compound of claim 13, which is

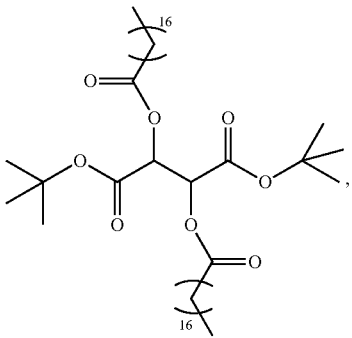

or a salt thereof.

17. A lubricating oil composition prepared by combining a lubricating oil base stock and a compound of formula (I):

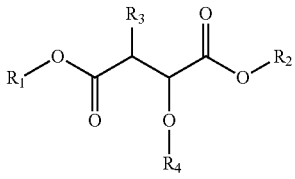

wherein, $R_1$ and $R_2$ are each independently H, tertiary $(C_4$-$C_{12})$alkyl, benzyl or phenethyl; $R_3$ is $OR^a$, wherein $R^a$ is $(C_1$-$C_{20})$alkanoyl, or $(C_3$-$C_{20})$alkenoyl; and $R_4$ is $(C_1$-$C_{20})$alkanoyl or $(C_3$-$C_{20})$alkenoyl; or a salt thereof.

18. A method of reducing friction in an engine or other mechanical component lubricated with a lubricating oil, comprising providing a lubricating oil composition of claim 1 to the engine or other mechanical component.

19. A method of providing friction reducing properties in a lubricant system, comprising adding a lubricating oil composition of claim 1 to the lubricant system.

20. A method of reducing friction in an engine or other mechanical component lubricated with a lubricating oil, comprising providing a lubricating oil composition of claim 2 to the engine or other mechanical component.

21. A method of providing friction reducing properties in a lubricant system, comprising adding a lubricating oil composition of claim 2 to the lubricant system.

22. The lubricating oil composition of claim 2, wherein, $R_1$ and $R_2$ are each H; $R_3$ is H or $OR^a$, wherein $R^a$ is $(C_1$-$C_{20})$alkanoyl or $(C_3$-$C_{20})$alkenoyl; and $R_4$ is $(C_1$-$C_{20})$alkanoyl or $(C_3$-$C_{20})$alkenoyl; or a salt thereof.

23. The lubricating oil composition of claim 22, wherein, $R_1$ and $R_2$ are each H; $R_3$ is $OR^a$, wherein $R^a$ is $(C_{10}$-$C_{20})$alkanoyl or $(C_{10}$-$C_{20})$alkenoyl; and $R_4$ is $(C_{10}$-$C_{20})$alkanoyl or $(C_{10}$-$C_{20})$alkenoyl; or a salt thereof.

24. The lubricating oil composition of claim 2, wherein, $R_1$ and $R_2$ are each tert-butyl; $R_3$ is H or $OR^a$, wherein $R^a$ is $(C_1$-$C_{20})$alkanoyl or $(C_3$-$C_{20})$alkenoyl; and $R_4$ is $(C_1$-$C_{20})$alkanoyl or $(C_3$-$C_{20})$alkenoyl; or a salt thereof.

25. The lubricating oil composition of claim 24, wherein, $R_1$ and $R_2$ are each tert-butyl; $R_3$ is $OR^a$, wherein $R^a$ is $(C_{10}$-$C_{20})$alkanoyl or $(C_{10}$-$C_{20})$alkenoyl; and $R_4$ is $(C_{10}$-$C_{20})$alkanoyl or $(C_{10}$-$C_{20})$alkenoyl; or a salt thereof.

26. The lubricating oil composition of claim 1, wherein, $R_1$ and $R_2$ are each independently tertiary alkyl selected from the group consisting of butyl, pentyl, hexyl, heptyl, octyl, nonyl, decyl, undecyl and dodecyl; $R_3$ is $OR^a$, wherein $R^a$ is $(C_1$-$C_{20})$alkanoyl or $(C_3$-$C_{20})$alkenoyl; and $R_4$ is $(C_1$-$C_{20})$alkanoyl or $(C_3$-$C_{20})$alkenoyl; or a salt thereof.

27. The lubricating oil composition of claim 26, wherein, $R_1$ and $R_2$ are each independently tertiary alkyl selected from the group consisting of butyl, pentyl, hexyl, heptyl, octyl, nonyl, decyl, undecyl and dodecyl; $R_3$ is $OR^a$, wherein $R^a$ is $(C_{10}$-$C_{20})$alkanoyl or $(C_{10}$-$C_{20})$alkenoyl; and $R_4$ is $(C_{10}$-$C_{20})$alkanoyl or $(C_{10}$-$C_{20})$alkenoyl; or a salt thereof.

* * * * *